(12) United States Patent
Wada et al.

(10) Patent No.: US 7,442,788 B2
(45) Date of Patent: *Oct. 28, 2008

(54) ANTISENSE MOLECULES AND METHOD OF CONTROLLING EXPRESSION OF GENE FUNCTION BY USING THE SAME

(75) Inventors: Takehiko Wada, Toyonaka (JP); Yoshihisa Inoue, Toyonaka (JP)

(73) Assignee: Japan Science and Technology Corporation, Kawaguchi-shi, Saitama (JP)

( * ) Notice: Subject to any disclaimer, the term of this patent is extended or adjusted under 35 U.S.C. 154(b) by 438 days.

This patent is subject to a terminal disclaimer.

(21) Appl. No.: 10/311,386

(22) PCT Filed: Jun. 13, 2001

(86) PCT No.: PCT/JP01/05012

§ 371 (c)(1),
(2), (4) Date: Dec. 12, 2002

(87) PCT Pub. No.: WO01/96356

PCT Pub. Date: Dec. 20, 2001

(65) Prior Publication Data

US 2003/0162739 A1    Aug. 28, 2003

(51) Int. Cl.
*C07H 21/04* (2006.01)
*C07K 2/00* (2006.01)
*A61K 38/00* (2006.01)

(52) U.S. Cl. ............... 536/24.5; 536/23.1; 530/300
(58) Field of Classification Search ............... None
See application file for complete search history.

(56) References Cited

OTHER PUBLICATIONS

Wada et al. Nucleic Acids Symposium Series 34, 1995, pp. 189-190.*
Opalinska et al. Nature Reviews Drug Discovery, 2002, vol. 1, p. 503-514.*
Takehiko Wada, et al., "Peptide Ribonucleic Acids (PRNA). 2. A Novel Strategy for Active Control of DNA Recognition through Borate Ester Formation," Journal of the American Chemical Society, 2000, vol. 122, No. 29, pp. 6900-6910.
Takehiko Wada, et al., "Conformational and Orientational Switching of Uridine Derivatives by Borates," Chemistry Letters 1998, pp. 1025-1026.
Takehiko Wada, et al., "Synthesis and properties of oligolysine and oligoglutamic acid derivatives containing nucleosides," Nucleic Acids Symposium Series No. 29, pp. 79-80.
Takehiko Wada, et al., "Synthesis and properties of polyamide derivatives containing nucleosides," Nucleic Acids Symposium Series No. 35, pp. 97-98.
Takehiko Wada, et al., "Synthesis and properties of oligo-ω-amino acids derivatives containing nucleosides," Nucleic Acids Symposium Series No. 34, pp. 189-190.
Hirofumi Sato, et al., "Synthesis and conformation control of peptide ribonucleic acid containing 5'-amino-5'-deoxyribopurinenucleosides," Nucleic Acids Symposium Series No. 44, pp. 211-212.
Isono, et al., "Polyoxin Analogs. I. Synthesis of Aminoacyl Derivatives of 5'-Amino-5'-deoxyuridine," Chemical & Pharmaceutical Bulletin, 19(3), pp. 505-512 1971.
Chang, et al., "Analogues of S-Adenosylhomocysteine as Potential Inhibitors of Biological Transmethylation. Synthesis of Analogues with Modifications at the 5'-Thioether Linkage," Journal of Medicinal Chemistry, vol. 19, No. 5 pp. 684-691 1976.
Herranz, et al., "Synthesis of 5'-N-(α-amino-β-mercaptoacyl)=amino-5'-deoxynucleosides as potential antiviral compounds," Chemical Abstracts, vol. 116, No. 1, Jan. 6, 1992.
Lee, et al., "Methionyl Adenylate Analogues as Inhibitors of Methionyl-tRNA Synthetase," Bioorganic & Medicinal Chemistry Letters 9(10) pp. 1365-1370 1999.

* cited by examiner

*Primary Examiner*—Tracy Vivlemore
(74) *Attorney, Agent, or Firm*—Knobbe, Martens, Olson & Bear LLP

(57) ABSTRACT

An antisense molecule which acts on both directions of the inhibition and expression of a gene function and is capable of on-off switching of a gene function appropriately depending on the external factors (orientation controlling factors); and a method for reversibly controlling the expression of a gene function by using the antisense molecule. Such an antisense molecule, which has at least one sugar-base moiety consisting of sugar and a purine or pyrimidine base bonded thereto via a glucoside bond, can bind to a mRNA/gene and/or dissociate therefrom under the orientation control of the base moiety in the molecule by the orientation controlling factors.

8 Claims, 26 Drawing Sheets

(a) Phosphate buffer

"anti"

(b) Borate buffer

"syn"

"anti"    "syn"

(a) Phosphate buffer $^1$H-NMR (b) Phosphate buffer

NOE

"anti"

(c) Borate buffer

NOE

"syn"

"syn"

" anti "     " syn "

a

+ D-Xylose b

Complex formation        Dissociation

Complex formation        Dissociation

ANTISENSE MOLECULES AND METHOD OF CONTROLLING EXPRESSION OF GENE FUNCTION BY USING THE SAME

This is a national stage application filed under 35 USC 371 based on International Application No. PCT/JP01/05012 filed Jun. 13, 2001, and claims priority under 35 USC 119 of Japanese Patent Application 2000-177525 filed Jun. 13, 2001.

1. Technical Field

The present invention relates to antisense molecules capable of carrying out novel functions in the antisense method. More particularly, the invention relates to antisense molecules having the on-off functions, namely reversibly controlling of the expression of a gene function (inhibition [off] and expression [on]).

The invention also relates to a novel method for controlling the expression of a gene function by utilizing the on-off functions of the antisense molecules mentioned above. More particularly, the invention relates to a method for reversibly controlling the expression of a gene function (inhibiting, expression) and thereby normalizing the gene function, by controlling the on-off functions of the antisense molecules by means of an external factor.

2. Background Art

Nucleic acids are highly functional macromolecules involved in accumulation and transmission of genetic information in living organisms. Specific recognition between nucleic acids or between a nucleic acid and a protein plays an important role in the function expression and regulatory function of the nucleic acid. With the recent rapid advances in genetic engineering and molecular biology, the mechanisms of such function expression have further been understood on a molecular level. A number of genes causative of diseases have been identified and the mechanisms of onset of such diseases have gradually been elucidated. With a background of such results, gene therapy has attracted attention by which therapy a disease is treated on a gene level using, as a therapeutic agent, a molecule capable of specific recognition in a manner mimicking the mode of recognition of a naturally occurring nucleic acid. The techniques of gene therapy which have so far investigated include, among others, the "gene transfer method" comprising artificially introducing a defective or deficient gene sequence into a patient's gene, the "antisense method" comprising binding an antisense molecule to mRNA in a base (nucleotide)-specific manner to thereby inhibit the synthesis of a protein causative of a disease, and the "antigene method" comprising binding an antisense molecule to a DNA region coding for a pathogenic protein to thereby inhibit the stage of transcription.

The so-called antisense molecule to be used in the "antisense method" or "antigene method" among the above-mentioned methods is required to have a number of characteristics, among which the following are important: 1) high-level ability to recognize a nucleic acid base sequence, 2) high stability in the form of complexes, 3) high stability against biological substances, in particular enzymes, 4) high cell membrane permeability, 5) ability to specifically interact with nucleic acids, and 6) nontoxicity to living bodies.

At first, attempts were made to use natural oligonucleotides as antisense molecules. Although these comparatively meet the above requirements 1) and 2), they have a problem in that they cannot meet the requirement 3) but are instantly decomposed enzymatically by means of nuclease occurring in vivo, so that the desired results cannot be attained.

The antisense molecules so far reported include, among others, 1) derivatives resulting from modification around the phosphate bonding, 2) derivatives resulting from modification of the glycosyl bonding or a hydroxyl group(s) in the ribose sugar portion, 3) derivatives resulting from modification of the base portion, and 4) nucleic acid model molecules having a skeletal structure other than the sugar-phosphate skeleton. More specifically, there may be mentioned such derivatives 1) as phosphorothioate type oligonucleotides resulting from substitution of a sulfur atom for an oxygen atom of the phospho-diester bonding and, further, phosphorodithioate type, phosphoroamidate type, methylphosphonate type and methylphosphonothioate type oligonucleotides; such derivatives 2) as α-anomer type oligonucleotides with the base coordinated in the sugar moiety in a manner reverse to the β-glucosyl bonding, oligonucleotides resulting from conversion of the sugar 3'-5' phosphodiester bonding to the 2'-5' bonding using a ribonucleotide, and 2'-methoxy derivatives resulting from methyl etherification at the 2' position of ribose; such derivatives 3) as modified bases, for example 5-fluorouracil (5-FU) resulting from substitution of a fluorine atom at the 5 position of uracil, and fluorescent ethenoadenosine; such derivatives 4) as peptide nucleic acids (PNAs) having a peptide skeleton in place of the sugar-phosphate skeleton (OE. Uhlman, A. Peyman, Chem. Rev., 1990, 90, 544; OE. Uhlman, A, Peyman, G. Breipohl, D. W. Will, Angew. Chem. Int., Ed. Engl., 1998, 37., 2796, etc.).

The peptide nucleic acids (PNAs) so referred to herein are compounds which have attracted attention in view of such advantageous features as their base-specific recognizing ability, resistance to enzymolysis, very high affinity for nucleic acids owing to their having a neutral peptide chain as the main chain, and the possibility of arbitrary sequence being obtained in a simple and easy manner by the amide bond formation reaction. However, their excessively high affinity, for example their binding to targets, including mismatching, is rather disadvantageous, and drawbacks have also been reported, for example 15-mer or higher oligomers, in particular, are nonspecifically adsorbed on intracellular proteins due to their having a hydrophobic peptide chain, or they are scarcely soluble in water.

Thus, there is room for improvement in antisense molecules, inclusive of PNAs.

Furthermore, the antisense methods currently under investigation are mostly intended only to suppressively control the expression of a function. Namely, the antisense molecules mentioned above are mostly used in the treatment of cancer or hereditary diseases through their ability to inhibit the function expression of a specific gene and induce cell death or function disappearance. Thus, the antisense molecules known in the art act, in one direction, to inhibit (suppress) the expression of an undesirable gene function (negative control) but cannot meet the requirement that the desired gene function expression should be restored (positive control).

However, the next-generation antisense molecules will be required to be able to diversified control the genetic information. For example, those antisense molecules will be desired which manifest an inhibitory function only in case of excessive expression of a specific protein and stop the inhibitory function after normalization of the expression level.

3. Disclosure of Invention

It is an object of the present invention to provide antisense molecules capable of controlling reversibly the gene function, namely capable of appropriately inhibiting and expression the gene function in an on/off switching manner according to the external environment. Another object of the invention is to provide a method for reversibly control the expression of a gene function by utilizing such antisense molecule.

The present inventors made intensive investigations to solve the above problems while paying attention to the base moiety orientation of nucleosides involved in mutual recognition and bonding of nucleic acids and, as a result, fount that a change in puckering of the sugar moiety of an antisense molecule having a specific structure can be induced by an external factor and confirmed that the orientation of the base moiety thereof can be controlled by controlling the change in puckering of the sugar moiety using external factor.

The process of recognition in complementary bonding of nucleic acids is greatly associated with the orientation (syn orientation, anti orientation) of the base moieties of nucleosides and, for efficient recognition of the counterpart nucleic acid sequence, the base moiety is required to have an anti orientation; with a syn orientation, such recognition can hardly be attained. The base moiety orientation control based on the above finding is such that the anti orientation and syn orientation of the base moiety of a nucleoside can be changed arbitrarily in either direction from one to the other by means of an external factor. It is thus expected that the ability to form a complex with a complementary nucleic acid can be artificially controlled, hence the expression of a gene function can be reversibly controlled (inhibited or expressed). The present invention has been completed base on such and other findings.

Thus, the invention provides antisense molecules mentioned below under 3-5, 7, 8, 10, 11 and 20-23 whose antisense function can be controlled in the on-off manner by an external factor:

3. An antisense molecule which is an amino acids-nucleoside (monomer) resulting from bonding of an amino acid or a derivative thereof, via a carbonyl or thiocarbonyl group, to the 5'-amino group of a 5'-amino-5'-deoxynucleoside, or a polymer thereof; or is an oligo- or polyamino acids-nucleoside (monomer) resulting from bonding of a polymer of an amino acid or a derivative thereof, either directly or via a carbonyl or thiocarbonyl group, to the 5'-amino group of a 5'-amino-5'-deoxynucleoside, or a polymer thereof; and which is used in its binding to a mRNA/gene and/or dissociation from the mRNA/gene, through the control of the pyrimidine or purine base moiety orientation in said molecule by an orientation controlling factor.

4. The antisense molecule according to 3 which is represented by the general formula (3):

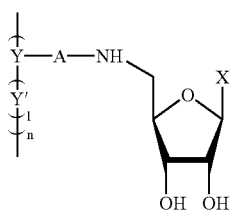

(3)

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid. lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a carbonyl or thiocarbonyl group, 1 is an integer of 0 to 5, and n is an integer of 1 to 100.

5. An antisense molecule which comprises a DNA or RNA or a derivative thereof and an amino acids-nucleoside (monomer) resulting from bonding of an amino acid or a derivative thereof, via a carbonyl or thiocarbonyl group, to the 5'-amino group of a 5'-amino-5'-deoxynucleoside, or a polymer thereof, or is an oligo- or polyamino acids-nucleoside (monomer) resulting from bonding of a polymer of an amino acid or a derivative thereof, either directly or via a carbonyl or thiocarbonyl group, to the 5'-amino group of a 5'-amino-5'-deoxynucleoside, or a polymer thereof as integrated in a part of the base sequence of the DNA, RNA or derivative thereof, and which is used in the binding to a mRNA/gene and/or dissociation from the mRNA/gene through the control of the pyrimidine or purine base moiety orientation in said amino acids-nucleoside or oligo/polyamino acids-nucleoside, or the polymer thereof by an orientation controlling factor.

7. The antisense molecule according to 3, which is to be used in the on-off control of a gene expression function.

8. The antisense molecule according to 5, which is to be used in the on-off control of a gene expression function.

10. The antisense molecule according to 9 for which the orientation controlling factor comprises an orientation regulating factor and an orientation regulation controlling factor.

11. The antisense molecule according to 10 for which the orientation regulating factor comprises at least one member selected from the group consisting of "borates", alkaline earth metals and transition metals, and the orientation regulation controlling factor comprises at least one member selected from the group consisting of pH, light, temperature and sugars.

12. An antisense composition which comprises an antisense molecule as defined in 1 and an orientation regulating factor.

13. The antisense composition according to 12, wherein the orientation regulating factor comprises at least one member selected from the group consisting of "borates", alkaline earth metals and transition metals.

16. A method for controlling the expression of a gene function which comprises controlling, using an orientation controlling factor, the state of orientation of the base relative to the sugar in an antisense molecule as defined in 3, to thereby control the binding of said antisense molecule to a mRNA/gene and/or dissociation of the antisense molecule from the mRNA/gene.

17. The method for controlling the expression of a gene function according to 16, wherein the antisense molecule as defined in 4 is used as the antisense molecule.

18. A method for controlling the expression of gene function which comprises:

(1) using an antisense molecule which is an amino acids-nucleoside (monomer) resulting from bonding of an amino acid or a derivative thereof, either directly or via a carbonyl or thiocarbonyl group, to the 5'-amino group of a 5'-amino-5'-deoxynucleoside, or a polymer thereof; an oligo- or polyamino acids-nucleoside (monomer) resulting from bonding of a polymer of an amino acid or a derivative thereof, either directly or via a carbonyl or thiocarbonyl group, to the 5'-amino group of a 5'-amino-5'-deoxynucleoside, or a polymer thereof; or a chimeric nucleic acid resulting from integration thereof into a part of the base sequence of a DNA or RNA or a derivative thereof;

(2) controlling the state of orientation of base relative to the sugar in said antisense molecule by an orientation regulating factor and an orientation regulation controlling factor;

(3) and thus controlling the binding of said antisense molecule to a mRNA/gene and/or dissociation of the antisense molecule from the mRNA/gene.

19. The method for controlling the expression of a gene function according to 14, wherein the orientation regulating factor comprises at least one member selected from the group consisting of "borates", alkaline earth metals and transition metals and the orientation regulation controlling factor comprises at least one member selected from the group consisting of pH, light, temperature and sugars.

20. The antisense molecule according to 3 which is represented by the general formula (3):

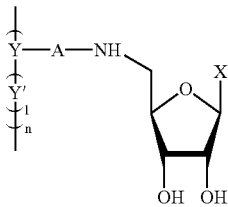

(3)

wherein X is(are) the same or different and each represents a pyrimidine or purine base or a derivative thereof, Y and Y' are the same or different and each represents at least one amino acid or amino acid derivative selected from the group consisting of serine, threonine, aspartic acid, glutamic acid, lysine, arginine, cysteine, methionine, ornithine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond or a carbonyl or thiocarbonyl group, 1 is an integer of 1 to 5, and n is an integer of 1 to 100.

21. (Added) The antisense molecule according to 20, wherein, in general formula (3), Y is represented by the formula (ii):

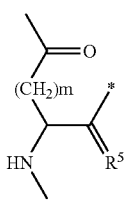

(ii)

wherein m is an integer of 1 to 3, $R^5$ is an oxygen or sulfur atom and * indicates the site of bonding to A in general formula (3).

22. The antisense molecule according to 4. wherein, in general formula (3), Y is represented by the formula (iii):

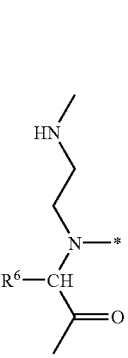

(iii)

wherein $R^6$ is a hydrogen atom or a carboxymethyl, carboxyethyl, hydroxymethyl, aminobutyl, aminopropyl or 4-amino-3-hydroxypropyl group and * indicates the site of bonding to A in general formula (3).

23. An antisense molecule represented by the general formula (3):

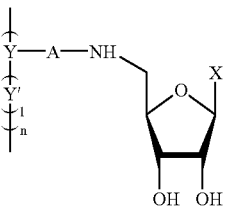

(3)

wherein X is(are) the same or different and each represents a pyrimidine or purine base or a derivative thereof, Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond, 1 is an integer of 0 to 5, n is an integer of 1 to 100, and Y is a group represented by the formula (i):

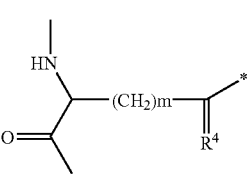

(i)

(in which m is an integer of 1 to 3, $R^4$ is an oxygen or sulfur atom and * indicates the site of bonding to A in general formula (3))

and intended for use in its binding to a mRNA/gene and/or departure from the mRNA/gene by controlling the orientation of the pyrimidine or purine base relative to the sugar in said molecule by an orientation controlling factor.

24. A method for controlling the expression of a gene function which comprises controlling, using an orientation controlling factor, the state of orientation of the base relative to the sugar in an antisense molecule as defined in 23 to thereby control the binding of said antisense molecule to a mRNA/gene and/or dissociation of the antisense molecule from the mRNA/gene.

25. The method for controlling the expression of a gene function according to 18, wherein a molecule represented by the general formula (3):

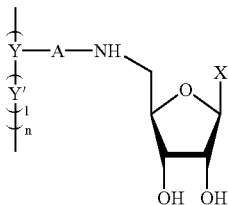

(3)

wherein X is(are) the same or different and each represents a pyrimidine or purine base or a derivative thereof, Y and Y' are the same or different and each represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid. A represents a single bond or a carbonyl or thiocarbonyl group, l is an integer of 0 to 5, and n is an integer of 1 to 100, is used as the antisense molecule.

BEST MODES FOR CARRYING OUT THE INVENTION

Figure 1:
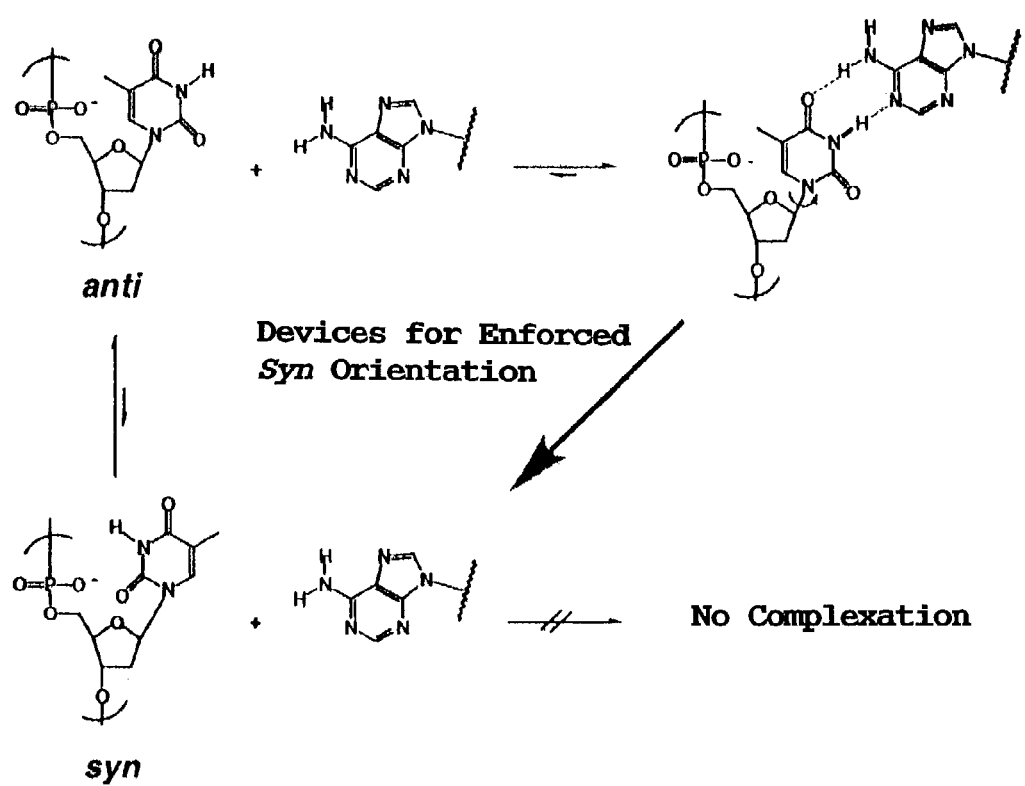
FIG. 1 is an illustration showing that the orientation (anti, syn) of the base moiety of the nucleic acid is involved in the process of nucleic acid recognition.

The antisense molecule to be used in the practice of the present invention is characterized in that it has a sugar-base moiety resulting from glucoside bonding between a sugar moiety and a base moiety such as a pyrimidine or purine base, namely a nucleoside structure.

The purine base so referred to herein is not particularly restricted but may be any one having a purine skeleton, generally including adenine and guanine, and derivatives of these. The pyridimine base is not particularly restricted but may be any one having a pyrimidine skeleton, generally including uracil, cytosine and thymine, and derivatives of these.

The derivatives so referred to herein are not particularly restricted but include, for example, halogenated derivatives, deaminated derivatives, or derivatives having a sulfur atom(s) in lieu of an oxygen atom(s), of uracil, cytosine, thymine, adenine or guanine.

More specifically, compounds represented by the formula (1) may be mentioned as the uracil derivatives.

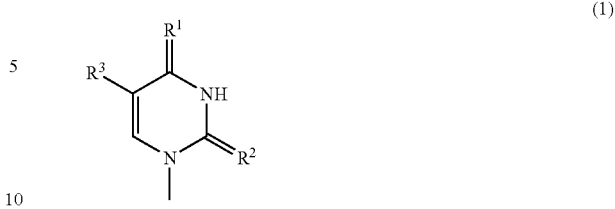

(In the formula, $R^1$ and $R^2$ are the same or different and each represents an oxygen or sulfur atom, and $R^3$ represents a hydrogen or halogen atom or an alkyl, alkenyl or alkynyl group.)

Here, the halogen specifically includes a fluorine atom, a bromine atom, an iodine atom and a chlorine atom. Preferred are a fluorine atom, a bromine atom and an iodine atom.

The alkyl group includes straight or branched lower alkyl groups containing 1 to 6 carbon atoms, such as methyl, ethyl, propyl, isopropyl, butyl, isobutyl, tert-butyl, pentyl and hexyl.

The alkenyl group includes straight or branched lower alkenyl groups containing 1 to 6 carbon atoms, such as vinyl, allyl, propenyl, isopropenyl, 2-methyl-1-propenyl, 2-methylallyl, 3-butenyl, 4-pentenyl, 5-hexenyl, and 1,3-butadienyl.

The alkynyl group includes straight or branched lower alkynyl groups containing 1 to 6 carbon atoms, such as ethynyl, 2-propynyl, 2-butynyl, 2-pentynyl, 2-hexynyl, and 2-penten-4-ynyl.

Thus, more specifically, there may be mentioned halogenated uracil derivatives such as 5-fluorouracil, 5-bromouracil and 5-iodouracil; uracil derivatives having a sulfur atom(s) in lieu of an oxygen atom(s), such as 2-thiouracil, 4-thiouracil and 2,4-dithiouracil; 5-methyluracil, 5-vinyluracil, and 5-ethynyluracil; and the like.

As for the cytosine derivatives, there may specifically be mentioned halogenated cytosine derivatives such as 5-fluorocytosine, 5-bromocytosine and 5-iodocytosine; and alkynyl group-containing cytosine derivatives such as 5-ethynylcytosine. Among them, 5-fluorocytosine is preferred.

As the guanine derivatives, there may specifically be mentioned deaminated guanine derivatives such as hypoxanthine, and halogenated guanine derivatives such as 8-fluoroguanine, 8-bromoguanine and 8-iodoguanine. Preferred are hypoxanthine and 8-bromoguanine.

As the adenine derivatives, there may specifically be mentioned 1,$N^6$-ethenoadenine representable by the formula:

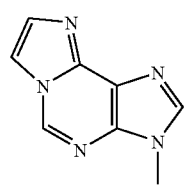

as well as halogenated adenine derivatives such as 8-fluoroadenine, 8-bromoadenine and 8-iodoadenine. Preferred are 1,$N^6$-ethenoadenine and 8-bromoadenine.

As appropriate purine bases to be used in the practice of the invention, there may be mentioned guanine, adenine, and hypoxanthine, which is a derivative thereof, and, as appropriate pyrimidine bases, uracil, thymine, and cytosine.

The sugar moiety to be used in the practice of the invention is preferably such a pentose as β-D-ribose generally used in ribonucleic acids or β-D-2-deoxyribose generally used in deoxyribonucleic acids and further includes, without limitation to these, hexoses such as β-D-glucose, β-D-mannose and α-D-galactose; and sugars having an amino group within the molecule, for example α-D-acetylglucosamine and α-D-acetylgalactosamine, among others.

As specific examples of the sugar-base moiety composed of such a base and a sugar as mentioned above, namely the nucleoside, there may be mentioned halogenated nucleosides such as 5-fluorouridine (5-FU), 5-bromouridine (5-BrU), 5-iodouridine (5-IU), 5-fluorocytidine (5-FC), 8-bromoadenosine (5-BrA) and 8-bromoguanosine (5-BrG); nitrogen-substituted nucleosides such as 2-thiouridine, 4-thiouridine and 2,4-dithiouridine; 5-ethynylcytidine, 5-methyluridine, 5-vinyluridine, 5-ethynyluridine; and, further, inosine, ethenoadenosine, oxalosine, 5-ethynylcytidine, and the like.

The antisense molecule to be used according to the invention preferably has a structure such that all or part of the base moieties in that molecule can be oriented freely in both directions of syn orientation or anti orientation. As specific examples, there may be mentioned antisense molecules having a cis-diol group at positions 2' and 3' (cis-2',3'-diol) in their sugar moiety and/or an amino hydrogen atom at position 5' in their sugar moiety for enabling hydrogen bonding with the oxygen atom of the carbonyl group at position 2 of the base moiety.

The antisense molecule to be used according to the invention includes 5'-amino-5'-deoxypyrimidine nucleosides and 5'-amino-5'-deoxypurine nucleosides, for instance. In other modes of embodiment, it includes the so-called "amino acids-nucleoside", in monomeric (1=0, n=1) or polymeric (1=0, n=2 to 100), resulting from coupling of the above amino acid or a derivative thereof (herein collectively referred to as "amino acids") to the 5'-amino group or 5'-aminonucleosides either directly or via a carbonyl, thiocarbonyl, carbamic acid, thiocarbamic acid, urea or thiourea group or bond, as well as the so-called "oligo- or polyamino acids-nucleoside", in monomeric (1=1 to 5, n=1) or polymeric (1=1 to 5, n=2 to 100) form, resulting from coupling of a polymer of the above "amino acids" (oligoamino acids, polyamino acids) to the 5'-amino group of 5'-aminonucleosides either directly or via a carbonyl, thiocarbonyl, carbamic acid, thiocarbamic acid, urea or thiourea group or bond. Hereinafter, these "amino acids-nucleoside" and "oligo- or polyamino acids-nucleoside" are collectively referred to as "PRNA".

As such PRNA, there may be mentioned those represented by the formula (3):

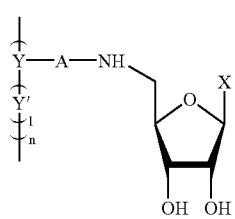

(3)

wherein X is(are) the same or different and each represents uracil, cytosine, thymine, adenine, guanine, or a derivative thereof, Y and Y' are the same or different and each represents at least one amino acid or amino acid derivative selected from the group consisting of serine, threonine, aspartic acid, glutamic acid, lysine, arginine, cysteine, methionine, ornithine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond or a carbonyl or thiocarbonyl group, 1 is an integer of 0 to 5, and n is an integer of 1 to 100.

As preferred examples of the derivative of uracil, cytosine, thymine, adenine or guanine as represented by X, there may be mentioned those mentioned hereinabove. The PRNA to be used in the practice of the invention may have one single base species or two or more different bases as the base(s) X(s) in each molecule.

In the general formula (3), the amino acid or amino acid derivative represented by Y or Y' is not particularly restricted provided that it does not manifest immunogenicity upon polymerization thereof (oligoamino acid, polyamino acid) but may be any of those specifically mentioned hereinabove. Preferred are, however, glutamic acid, aspartic acid, homoglutamic acid, ω-thiocarbonyl amino acids (β-thiocarbonylaspartic acid, γ-thiocarbonylglutamic acid, δ-thiocarbonylhomoglutamic acid, etc.), and N-aminoethylglycine. These amino acids and amino acid derivatives may be in the d-form, 1-form or racemic form. These amino acids and amino acid derivatives are bound to the 5'-carbon of the sugar-base moiety through amide, carbamic acid, thiocarbamic acid, dithiocarbamic acid, urea, thiourea, ester or like bonding. The position in the amino acid or amino acid derivative which is bound to said 5'-carbon is not particularly restricted. For example, an amide bond may be formed between the 5'-amino group of 5'-aminonucleoside and the α- or β-carboxyl group of aspartic acid, which is a dicarboxylic acid, the α- or γ-carboxyl group of glutamic acid, or the α- or δ-carboxyl group of homoglutamic acid, and a thioamide bond may be formed between the 5'-amino group of 5'-aminonucleoside and the α-thiocarboxyl group of β-thiocarbonylaspartic acid or the γ-thiocarboxyl group of γ-thiocarbonylglutamic acid. In the case of lysine, which is a diamine, the above-mentioned bond may be formed between the α-amino group or ε-amino group and the 5'-amino group of the sugar-base moiety and, in the case of serine, between the β-hydroxyl group and the 5'-amino group.

The N-terminal of the amino acid or amino acid derivative represented by —(Y—(Y')$_1$)$_n$—, either in the monomer or polymer form, may be a free amino group or have an arbitrary functional group having an amide, carbamic acid, thiocarbamic acid, urea, or phosphoramide bond, for instance, without any particular restriction. The C terminal may also be a free carboxyl group or have an arbitrary functional group having an amide or ester bond, for instance, without any particular restriction.

In accordance with the present invention, 1 is generally selected from within the range of integers 0 to 5, but preferably is an integer of 0 to 2, more preferably an integer of 0 or 1.

In accordance with the invention, n is generally selected from within the range of integers 1 to 100, but preferably is an integer of 6 to 50, more preferably an integer of 8 to 20.

The antisense molecule according to the invention specifically includes those compounds I, II and III which are shown below.

Compounds I:

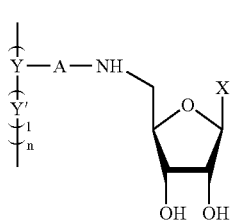
(3)

(In the formula, X is(are) the same or different and each represents a pyrimidine or purine base or a derivative thereof, Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond; l is an integer of 0 to 5, and n is an integer of 1 to 100; and Y is a group represented by the formula (i):

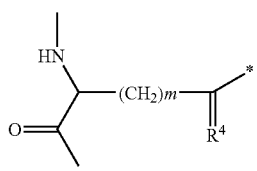
(i)

[wherein m is an integer of 1 to 3, $R^4$ represents an oxygen or sulfur atom, and * indicates the site of bonding to A in the PRNA represented by the general formula (3)].)

Compounds II:

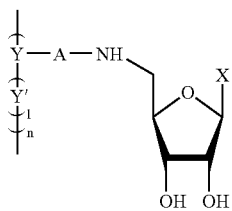
(3)

(In the above formula, X, Y', l and n are as defined above, A represents a single bond, and Y is a group of the formula (ii):

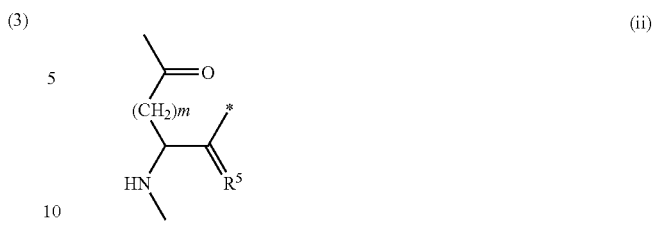
(ii)

[wherein m is an integer of 1 to 3, $R^5$ represents an oxygen or sulfur atom, and * indicates the site of bonding to A in the PRNA represented by the general formula (3)].)

Compounds III:

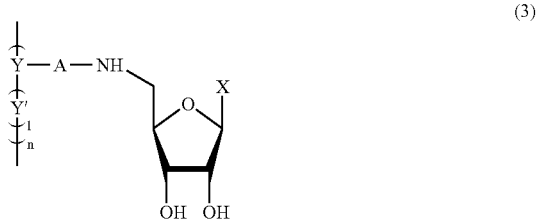
(3)

(In the above formula, X, Y', l and n are as defined above, A represents a carbonyl or thiocarbonyl group, and Y is a group of the formula (iii):

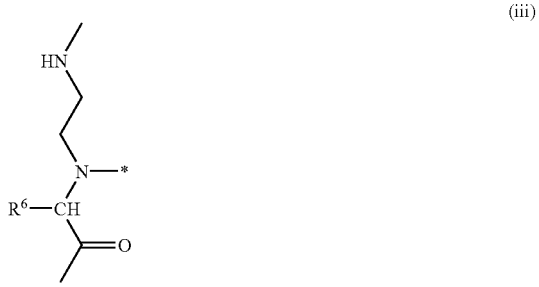
(iii)

[wherein $R^6$ represents a hydrogen atom or a carboxymethyl, carboxyethyl, hydroxymethyl, aminobutyl, aminopropyl or 4-amino-3-hydroxypropyl group, and * indicates the site of bonding to A in the PRNA represented by the general formula (3)].)

The PRNAs represented by the above formulas I, II and III are hereinafter referred to as PRNA1 (α type), PRNA2 (γ type) and PRNA3 (AEG type), respectively.

These PRNAs can be produced by various methods. In the case of PRNA1, for instance, the PRNA (1-i) (where l=0)

which have a group represented by the formula (i) as the group Y can be produced in the following manner.

Reaction formula 1

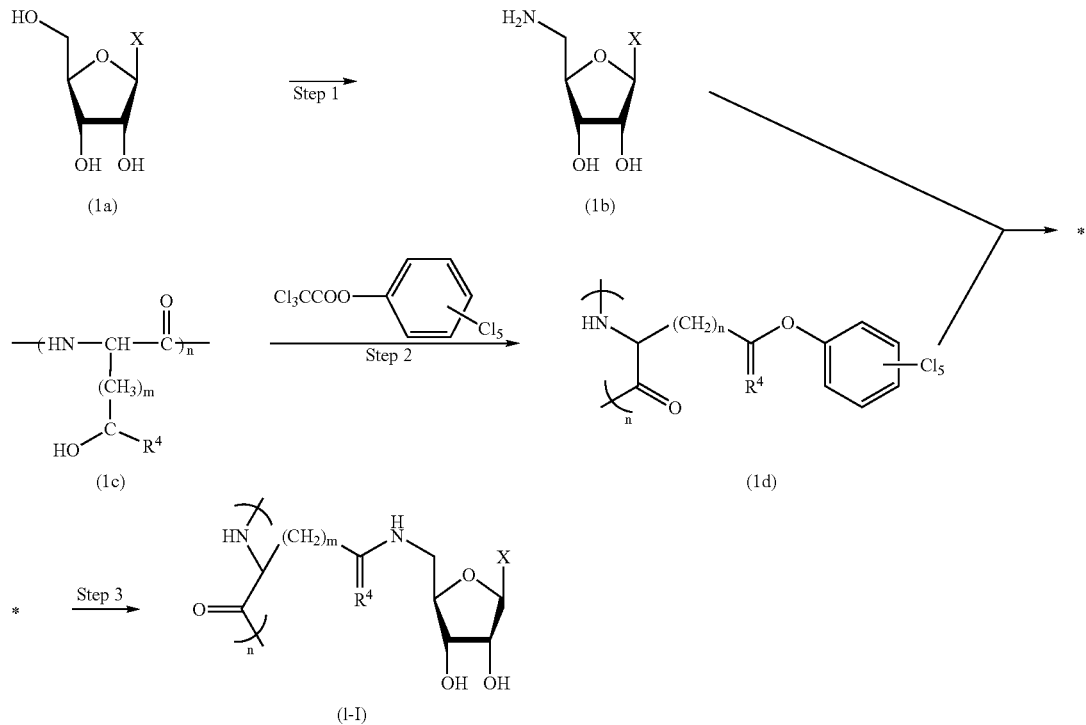

(In the formula, X, $R^4$, m and n are as defined above.)

In accordance with the reaction formula 1, a 5'-aminonucleoside derivative (1b) is produced by aminating the hydroxyl group (5'-hydroxyl group) bound to the 5' carbon in the sugar moiety of a nucleoside or nucleoside derivative of the general formula (1a) (step 1). Separately, an amino acid derivative (1d) is produced by reacting such an amino acid (1c) as L-aspartic acid, D-aspartic acid, β-thiocarbonyl-L-aspartic acid, β-thiocarbonyl-D-aspartic acid (in all the above, m=1), L-glutamic acid, D-glutamic acid, γ-thiocarbonyl-L-glutamic acid, γ-thiocarbonyl-D-glutamic acid (in the above, m=2), L-homoglutamic acid, D-homoglutamic acid, δ-thiocarbonyl-L-homoglutamic acid or δ-thiocarbonyl-D-homoglutamic acid (in the above, m=3) with pentachlorophenyl trichloroacetate (step 2). The nucleoside derivative (1b) and amino acid derivative (1d) respectively produced in the above steps are reacted with each other, whereby the nucleoside derivative (1-i) of the invention can be produced (step 3).

In step 1, various methods of substituting an amino group for a hydroxyl group can be used. Specifically, the method of Mitsunobu (T. Hata, et al., J. Chem. Soc., Perkin 1, 306 (1976); T. Hata, et al., Chem. Lett., (1975), pp. 977-980), for instance, can be applied. Specifically, the step can be carried out according to the following formula.

<Step 1>

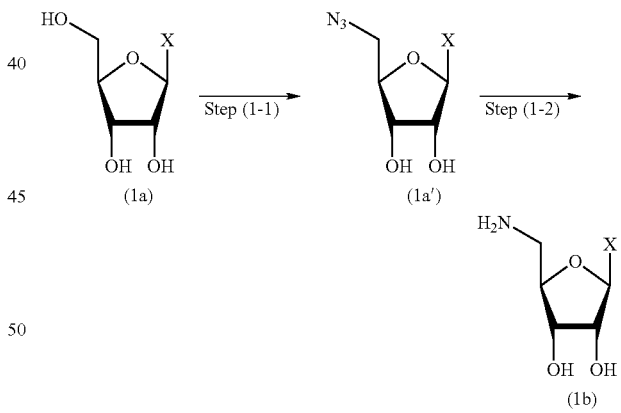

(In the formula, X is as defined above.)

The step (1-1) involves a reaction for converting the 5'-hydroxyl group of the nucleoside or nucleoside derivative (1a) to an azido group. When the nucleoside or nucleoside derivative (1a) is reacted with triphenylphosphine ($PPh_3$), lithium azide ($LiN_3$) and carbon tetrabromide ($CBr_4$) in an appropriate solvent, for instance, the 5'-$N_3$-nucleoside derivative (1a') can be obtained.

Here, the reaction solvent includes hydrocarbon solvents such as cyclohexane, benzene and toluene; halogenated hydrocarbon solvents such as dichloromethane, chloroform, dichloroethane, trichloroethane and chlorobenzene; water;

alcohol solvents such as methanol, ethanol and isopropanol; carboxylic acids such as formic acid and acetic acid; ether solvents such as tetrahydrofuran and dioxane; acetic anhydride; acetone; dimethylformamide, dimethyl sulfoxide; acetonitrile; THF; methylene chloride, etc. Preferred are dimethylformamide and dimethyl sulfoxide, and they are used preferably after drying. The amount of the solvent is generally 20 to 1000 parts by weight, preferably about 50 to 100 parts by weight, per part by weight of the nucleoside or nucleoside derivative of general formula (1a).

Triphenylphosphine, lithium azide and carbon tetrabromide are used each preferably in an amount of about 1 to 10 moles per mole of the nucleoside or nucleoside derivative of general formula (1a).

Such reaction can be carried out generally within the range of 0 to 80° C., and will be complete in about 1 to 36 hours. The reaction is terminated by addition of a polar solvent such as methanol, and the solvent is then distilled off. The 5'-$N_3$-nucleoside derivative (1a') can be isolated by further carrying out an ordinary purification procedure such as column chromatography, as necessary.

The step (1-2) involves a reaction for converting the azido group of the above 5'-$N_3$-nucleoside derivative (1a') to an amino group and can be carried out, for example, by reacting with hydrogen in an appropriate solvent. This reaction is preferably carried out in the presence of such a catalyst as palladium-on-carbon or ruthenium-on-carbon.

Here, the reaction solvent includes hydrocarbon solvents such as cyclohexane, benzene and toluene; halogenated hydrocarbon solvents such as dichloromethane, chloroform, dichloroethane, trichloroethane and chlorobenzene; water; alcohol solvents such as methanol, ethanol and isopropanol; carboxylic acids such as formic acid and acetic acid; ether solvents such as tetrahydrofuran and dioxane; acetic anhydride; acetone, dimethylformamide, dimethyl sulfoxide and like polar solvents, among others. Preferred are alcohols such as methanol and ethanol, and dimethylformamide. The amount of the solvent is generally 20 to 1000 parts by weight, preferably about 50 to 100 parts by weight, per part by weight of the 5'-$N_3$-nucleoside or 5'-$N_3$-nucleoside derivative of general formula (1a').

Such reaction can be carried out generally at room temperature, preferably within the range of 0 to 50° C., and will be complete in about 0.5 to 48 hours. After completion of the reaction, the reaction mixture filtrate is concentrated, and the residue is reprecipitated using a methanol-based solvent, for instance, whereby the 5'-$NH_2$-nucleoside derivative (1b) can be obtained. Desirably, a mixed solvent composed of methanol and ethanol is used as the methanol-based solvent.

<Step 2>

The step 2 can be carried out by reacting the amino acid (1c) with pentachlorophenyl trichloroacetate in an appropriate solvent.

Here, the reaction solvent include hydrocarbon solvents such as cyclohexane, benzene and toluene; halogenated hydrocarbon solvents such as dichloromethane, chloroform, dichloroethane, trichloroethane and chlorobenzene; water; alcohol solvents such as methanol, ethanol and isopropanol; carboxylic acids such as formic acid and acetic acid; ether solvents such as tetrahydrofuran and dioxane; acetic anhydride; acetone; dimethylformamide; acetonitrile; THF; methylene chloride, etc. Preferred are dimethylformamide, dimethyl sulfoxide and like polar solvents. The amount of the solvent is generally 10 to 1000 parts by weight, preferably about 20 to 100 parts by weight, per part by weight of the polyamino acid.

Said reaction can be carried out within the range of 0 to 80° C. and will be complete in about 0.5 to 48 hours.

<Step 3>

The step 3 can be carried out by adding the 5'-$NH_2$-nucleoside derivative (1b) obtained in the above step 1 to the reaction mixture of the above step 2, followed by mixing, whereby the nucleoside derivative of the invention as represented by the general formula (1-i) can be obtained. The proportions of the 5'-$NH_2$-nucleoside derivative (1b) and amino acid derivative (1d) to be subjected to the reaction are not particularly restricted but mention may be made of the range of about 0.8 to 1 mole of the amino acid derivative (1d) per mole of the 5'-$NH_2$-nucleoside derivative (1b). The reaction is carried out within the range of 0 to 40° C., preferably 0 to 40° C., and will be complete generally in about 24 to 48 hours.

The reaction product obtained by each of the above-mentioned reactions can be isolated from the reaction system and further purified by the conventional means known in the art. Such method of purification includes recrystallization, column chromatography, preparative thin layer chromatography, solvent extraction and reprecipitation, among others.

The above reaction process gives the PRNA of the invention in which A in general formula (3) is a single bond.

In the case of PRNA2, for instance, the PRNA (where 1=0) which have a group represented by the formula (ii) as the Y group can be produced by the process shown below in terms of reaction formula 2.

Reaction formula 2

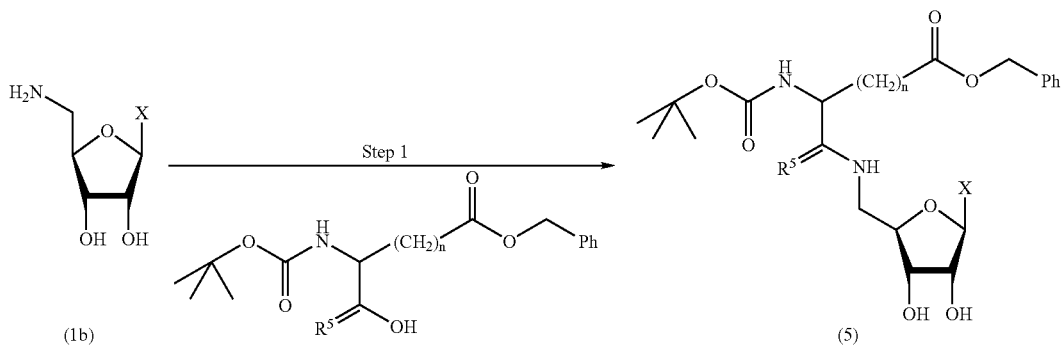

-continued

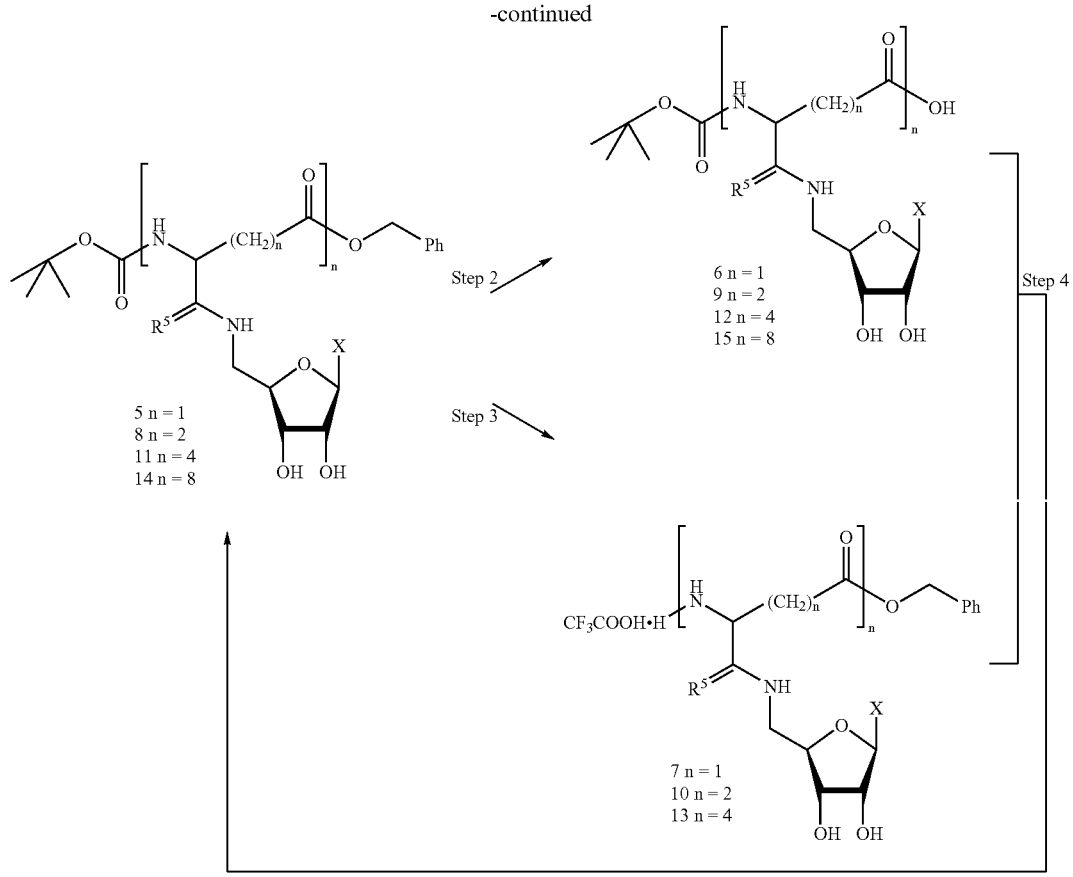

(In the formula, X, m and $R^5$ are as defined above.)

According to the reaction formula 2, a monomer (compound 5) composed of an amino acid serving as the peptide main chain and a nucleoside bound thereto is synthesized by coupling the 5'-$NH_2$-nucleoside derivative (1b), via the 5'-amino group thereof, to the α-carboxyl group of an amino acid whose amino and carboxyl groups are both protected (step 1), and the nucleoside derivative of the invention is then produced by using the monomer obtained as a unit and subjecting the same to consecutive elongation at the N terminus and C terminus thereof by repeating a selective deprotection and condensation cycle (steps 2 to 4). The amino acid mentioned above includes those having two carboxyl groups per molecule, such as L-aspartic acid, D-aspartic acid, β-thiocarbonyl-L-aspartic acid, β-thiocarbonyl-D-aspartic acid (in all the above, m=1), L-glutamic acid, D-glutamic acid, γ-thiocarbonyl-L-glutamic acid, γ-thiocarbonyl-D-glutamic acid (in the above, m=2), L-homoglutamic acid, D-homoglutamic acid, δ-thiocarbonyl-L-homoglutamic acid and δ-thiocarbonyl-D-homoglutamic acid (in the above, m=3).

<Step 1>

As mentioned above, the step 1 involves a reaction for coupling the α-carboxyl group of the amino acid or amino acid derivative serving as the peptide main chain unit to the 5'-amino group of the nucleoside derivative, and uses, as the starting materials, the amino acid derivative whose amino group and whose carboxyl group (e.g. (ω-carboxyl group) other than α-carboxyl group are protected, and the 5'-$NH_2$-nucleoside derivative (1b) produced, according to the process of above mentioned <Step 1> in reaction formula 1.

The amino-protecting group for the amino acid, which is to be used here, includes a wide variety of amino-protecting groups commonly used in peptide synthesis. As such amino-protecting groups, there may be mentioned, for example, carbobenzoxy, tert-butyloxycarbonyl, 9-fluorenylmethoxycarbonyl, phthalyl, formyl, acetyl, trifluoroacetyl, p-toluenesulfonyl, triphenylmethyl, cyclohexyloxycarbonyl, o-nitrophenylsulfenyl, tert-amyloxycarbonyl, benzyl, alkyl- or allylthiocarbonyl, o-nitrophenoxyacetyl, chloroacetyl, benzenesulfonyl, dibenzylphosphoryl, trialkylsilyl, allylidene, and acetoacetyl, which may optionally be substituted. Preferred from the high yield and highly selective deprotection viewpoint are tert-butyloxycarbonyl and 9-fluorenylmethoxycarbonyl.

As the carboxyl-protecting group for the amino acid, there may generally be mentioned esters such as methyl ester, ethyl ester, tert-butyl ester, benzyl ester and p-nitrobenzyl ester, as well as N'-substituted hydrazides, among others. Preferred from the high yield and highly selective deprotection viewpoint are the benzyl ester and p-nitrobenzyl ester, which can be eliminated by catalytic hydrogenation.

As more preferred specific examples of the amino acid or amino acid derivative, there may be mentioned amino acids or amino acid derivatives whose amino group is protected by a tert-butyloxycarbonyl group (Boc-) and whose carboxyl group is protected by a benzyl ester group (-OBzl), and amino acids and amino acid derivatives whose amino group is protected by a 9-fluorenylmethoxycarbonyl group (Fmoc-) and whose carboxyl group is either free or protected by a benzyl ester group (-OBzl). The above-mentioned N, γC-protected amino acids resulting from introduction of an arbitrary protective group(s) thereinto can all be produced by a conventional method.

The above coupling reaction between the N, γC-protected amino acid and 5'-NH$_2$-nucleoside derivative (1b) can be carried out in the manner of amide bond formation reaction using a condensing agent, such as DCC (dicyclohexylcarbodiimide), WSC (water-soluble dicyclohexylcarbodiimide) or BOP (benzotriazole-1-yloxytris(dimethylamino)phosphonium hexafluorophosphate), and an additive agent, such as HOBt (1-hydroxybenzotriazole), HONSu (N-hydroxysuccinimide), paranitrophenol, pentafluorophenol or pentachlorophenol. Such reaction can be carried out in DMF (N,N-dimethylformamide), DMSO (dimethyl sulfoxide), CHCl$_3$, CH$_2$Cl$_2$, CH$_3$CN or some other nonpolar solvent in the presence of diisopropylethylamine, and such reaction leads to formation of the monomer (compound 5).

The monomer (5) formed can be isolated and purified from the reaction mixture by a conventional method. More specifically, there may be mentioned the method comprising removing the solvent from the reaction mixture, extracting the product from the residue using ethyl acetate and, then, purifying the same utilizing the technique of column chromatography, for instance.

<Steps 2 to 4>

In the steps 2 to 4, an oligomer is formed by subjecting the monomer (5) obtained in the above <step 1>, as a unit, to condensation/elongation reaction. More specifically, in those steps, the oligomer (polymer) is produced by repetition of a reaction cycle (selective deprotection-condensation/repetition cycle) comprising the selective deprotection reactions of the carboxyl terminus and amino terminus of the above monomer (steps 2 and 3) and the subsequent condensation reaction (step 4) (selective deprotection-condensation cycle).

More detailedly, the selective deprotection-condensation cycle is carried out in the following manner.

1̂ First, the benzyl ester group, namely the carboxyl-protecting group, of the N,C-protected monomer (5) formed in the above <step 1> is eliminated by catalytic hydrogenation to give the corresponding free carboxyl group-containing N-protected monomer (compound 6, n=1) (step 2).

2̂ Separately, the tert-butyloxycarbonyl group, namely the amino-protecting group, of the N,C-protected monomer (5) formed in the above <step 1> is eliminated by acid treatment using trifluoroacetic acid, for instance, to give the corresponding free amino group-containing C-protected monomer (compound 7, n=1) (step 3).

3̂ Thereafter, the compound 6 and compound 7 respectively formed by the reactions in the above step 2 and step 3 are subjected to condensation by an amide bond formation reaction using the reagents HOBt and BOP, whereby the dimer (compound 8, n=2) is formed (step 4).

When the above cycle comprising the steps 1̂ to 3̂ is repeated, the PRNA oligomer whose carboxyl and amino groups are protected can be produced (two repetitions: tetramer (compound 11); three repetitions: octamer (compound 14).

The preparation of the PRNA2 (γPRNA) having a free amino group and a free carboxyl group can be carried out in the conventional manner by eliminating the amino-protecting group and carboxyl-protecting group from the N-,C-protected PRNA oligomer obtained as mentioned above. The process described in Production Example 3 may be mentioned as a specific example.

As mentioned above, those PRNAs of the present invention in which A, in general formula (3), is a single bond can be produced according to the process represented by the reaction formula 2.

Further, in the case of PRNA3, for instance, the PRNA (1-iii) (where l=0) having a group represented by the formula (iii) as the Y group can be produced according to the process represented by the following reaction formula 3.

Reaction Formula 3

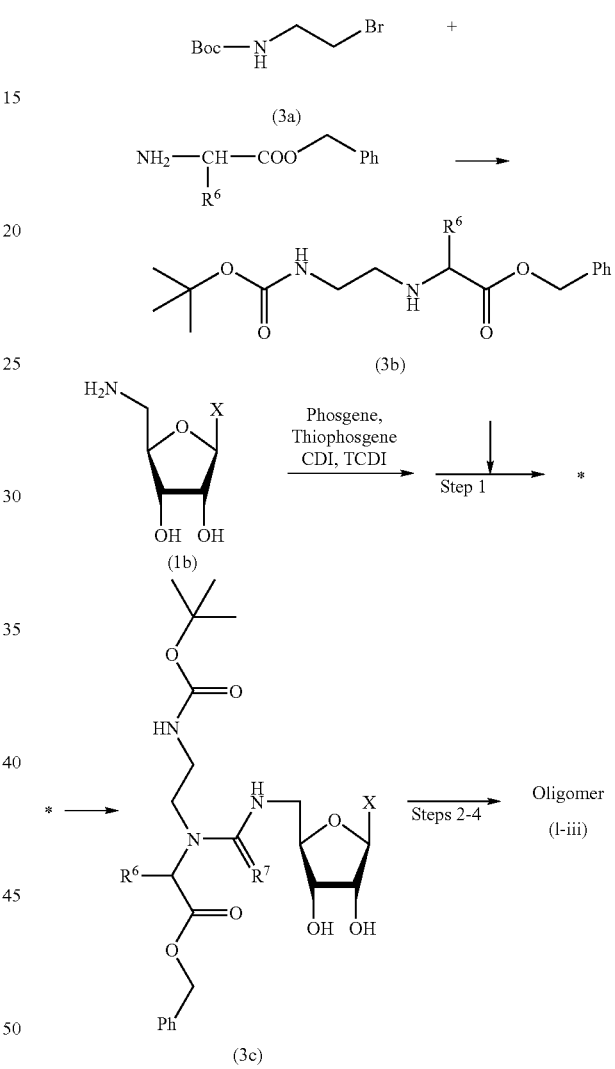

(In the formula, X and R$^6$ are as defined above and R$^7$ represents an oxygen or sulfur atom.)

According to the reaction formula 3, a monomer (compound 3c) composed of a peptide main chain and a nucleoside bound thereto is synthesized by coupling the 5'-NH$_2$-nucleoside derivative (compound 1b), via the 5'-amino group thereof, to the α-amino group of an amino acid (compound 3b) whose amino and carboxyl groups are both protected (step 1), and the monomer (3c) obtained is then used as a unit and subjected to elongation using an amide bond formation reaction to give a nucleoside derivative (1-iii) of the invention (steps 2 to 4).

As for the amino-protecting group and carboxyl-protecting group, those protective groups mentioned hereinbefore referring to PRNA2 can all be used. In cases where aminoethyleneglycine (AEG) ($R^7$ being a hydrogen atom) is used as the peptide main chain, Boc-AEG-OBn produced by using ethylenediamine as a starting material is judiciously used as the compound having protective groups at the N terminus and C terminus.

More specifically, the steps are performed in the following manner.

A Boc group can be introduced into 2-bromoethylamine (3a) by a conventional method, specifically by adding di-tert-butyl dicarbonate ($(Boc)_2O$) dropwise to a solution of 2-bromoethylamine (3a) in an appropriate solvent. Here, dioxane, THF, dimethylformamide, chloroform, methylene chloride or the like may be used as the solvent. Di-tert-butyl dicarbonate is used generally in amount of 1 to 2 moles, preferably about 1.2 moles, per mole of 2-bromoethylamine (3a). Preferably, the dropping is conducted within the range of −10 to 20° C.

The reaction product (N-protected compound) is then isolated and purified from the reaction mixture by a conventional method. More specifically, water is added to the residue after removal of the solvent from the reaction mixture, and the resulting aqueous layer is extracted with a nonpolar organic solvent such as chloroform. Then, the N-Boc-protected compound that has migrated to the organic layer is purified by utilizing column chromatography, for instance.

Then, an amino acid in the form of a benzyl ester derivative is reacted with the N-protected compound obtained as described above, whereby a butoxycarbonyl group is introduced into the amino group of the amino acid benzyl ester derivative (Boc-amino acid derivative-OBn, N,C-protected amino acid derivative) (3b). Such reaction can be carried out in a solvent such as chloroform, methylene chloride, dioxane, dimethylformamide or dimethyl sulfoxide. The amounts of diisopropylethylamine and benzyl bromoacetate are about 0.5 to 2 moles and about 1 to 2 moles, respectively, per mole of N-Boc-1,2-aminoethane. The reaction is preferably carried out within the range of 0 to 60° C. Generally, such reaction will be complete in 0.5 to 24 hours.

The reaction product (N,C-protected amino acid derivative) (3b) produced by the above reaction can be isolated from the reaction system and purified in conventional means known in the art. As such a method of purification, there may be mentioned recrystallization, column chromatography, preparative thin layer chromatography, and solvent extraction, among others.

Then, in step 1, the 5'-$NH_2$-nucleoside derivative (1b) synthesized by the process of reaction formula 1 (step 1) is then reacted with the N,C-protected amino acid derivative (3b) obtained as described above, whereby the N,C-protected PRNA3 monomer (3c) can be produced. In this case, it is preferred that the 5'-$NH_2$-nucleoside derivative (1b) be reacted in advance with N,N'-carbonyldiimidazole (CDI), phosgene, N,N'-thiocarbonyldiimidazole (TCDI) or thiophosgene and the thus-obtained reaction product be reacted with the above N,C-protected amino acid derivative (3b). Such reactions can be carried out in DMF, chloroform, methylene chloride, dimethyl sulfoxide or some other nonpolar solvent.

The proportion of the above-mentioned CDI or the like per mole the 5'-$NH_2$-nucleoside derivative (1b) is generally about 1 to 2 moles, preferably about 1 mole. Such reaction is preferably carried out at a low temperature, generally within the range of −120 to 0° C., preferably −78 to −40° C., so that side reactions involving the 3' and/or 2' hydroxyl group of the 5'-$NH_2$-nucleoside derivative (1b) may be inhibited. After 0.5 to 2 hours of reaction, the reaction system is returned to room temperature, and the N,C-protected amino acid derivative (3b) is added. The proportion of the N,C-protected amino acid derivative (3b) is generally about 1 to 2 moles, preferably about 1 to 1.5 moles, per mole of the 5'-$NH_2$-nucleoside derivative (1b).

The reaction product (N,C-protected PRNA3 monomer (3c)) produced by the above reaction is isolated from the reaction system and purified by conventional means known in the art. As such method of purification, there may be mentioned recrystallization, column chromatography, preparative thin layer chromatography, solvent extraction and reprecipitation. The isolation and purification of the above product is preferably carried out at room temperature or a lower temperature.

Then, the thus-obtained N,C-protected PRNA3 monomer (3c) can be oligomerized by a conventional method, for example by repeating the so-called selective deprotection-condensation cycle comprising the carboxyl-protecting group elimination step 2, the amino-protecting group elimination step 3 and the step 4 in which the C-deprotection production and N-deprotection product are condensed under amide bond formation, as mentioned hereinabove referring to PRNA2, or by the solid synthesis method, sequential condensation method, and fragment condensation method.

Those nucleoside derivatives in which A in general formula (1) is a carbonyl group can be produced by using, as a starting material, serine, threonine, aspartic acid, glutamic acid, lysine, arginine, cysteine or ornithine, δ-hydroxylysine, N-aminoethylglycine, N-aminoethylserine, N-aminoethyllysine, N-aminoethylornithine, N-aminoethylaspartic acid, N-aminoethylglutamic acid, or a oligomer or polymer thereof and reacting the same with N,N'-carbonyldiimidazole (CDI), phosgene or the like. Those nucleoside derivatives in which A is thiocarbonyl can be produced by using the above amino acid derivative or an oligomer or polymer thereof as a starting material and reacting the same with N,N'-thiocarbonyldiimidazole, thiophosgene or the like.

The 5'-amino-5'-deoxynucleosides and the PRNA prepared in the above manner each can be used as an antisense molecule either as such or in the form incorporated as a part of the nucleotide sequence of a DNA or RNA or a derivative thereof. Thus, the antisense molecule of the invention includes not only the 5'-amino-5'-deoxynucleosides and the above-mentioned PRNA but also the so-called chimeric nucleic acids resulting from integration thereof into at least a part of the base sequence of a DNA or RNA or a derivative thereof.

The DNA or RNA derivative so referred to herein includes not only those equivalent in physiological function to nucleic acids such as DNA or RNA but also nucleic acid derivatives known in the art as antisense molecules such as PNA and other nucleic acid analogues that are currently known or will be found in the future. As examples of the DNA derivatives, for instance, there may be mentioned those represented by the following formula:

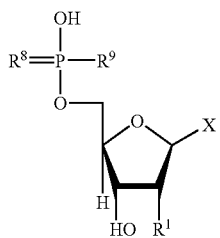

(In the formula, X is defined above, $R^1$ represents a hydrogen atom or a hydroxyl group, $R^8$ represents an oxygen or sulfur atom, $R^9$ represents $O^-$, $S^-$, $NH_2$, $NHR^{10}$, $NR^{10}R^{11}$, or $R^{10}$. $R^{10}$ and $R^{11}$ are the same or different and each represents $CH_3$, $(CH_2)_nCH_3$, $(CH_2)_nNHZ$, $(CH_2)_nNZZ'$, or $(CH_2)_nNH_2$ [in which Z and Z' are the same or different and each represents a lower alkyl group containing 1 to 4 carbon atoms, such as methyl, ethyl, isopropyl, n-propyl, tert-butyl, isobutyl or n-butyl, and n is an integer of 0 to 10].)

The nucleoside derivative of the invention can be coupled to a DNA or RNA, or a derivative thereof, either directly or via a spacer. The mode of such bonding is not particularly restricted but includes, in the case of direct bonding, the modes of bonding of the N or C terminus of the PRNA to the 5' or 3' terminus of a DNA or a derivative thereof via a phosphodiester, methylphosphonate, methylphosphonothioate, phosphorothioate, amide, sulfoamide, ethylene glycol, or thioformal bond, among others. As the mode of bonding of the nucleoside derivative of the invention to a DNA or RNA or a derivative thereof via a spacer, there may be mentioned, for example, those resulting from coupling of the 5'- or 3'-amino group or 5'- or 3'-hydroxyl group of a DNA or RNA or a derivative thereof to the carboxyl group of the PRNA via a lower alkylene group containing 1 to 10 carbon atoms ($(CH_2)_n$, n=1 to 10), such as a methylene, ethylene, propylene or butylene group; or a polymer of a lower alkyleneoxy group containing 1 to 4 carbon atoms, such as a methyleneoxy or ethyleneoxy group, for example $(CH_2O)_n$ or $(CH_2CH_2O)_n$ (n=1 to 10).

Such coupling of the PRNA to a DNA or RNA or a derivative thereof can be carried out by a conventional method.

The antisense molecule of the present invention is characterized in that all or part of the base moieties contained in said molecule are in a state of equilibrium between the syn orientation and anti orientation and that the syn-anti equilibrium can be arbitrarily controlled by means of an external factor.

The orientation controlling factor so referred to herein means an external factor capable of controlling the syn-anti orientation of the base moieties of the above antisense molecule in an arbitrary direction. The external factor so referred to herein means a factor which is other than the antisense molecule but can act on the antisense molecule, irrespective of its being artificial or natural or occurring in vivo or in vitro. It thus includes a wide variety of environmental factors in the living body and artificially constituted factors as well.

The orientation controlling factor is not particularly restricted but may be any of various factors capable of manifesting above function against antisense molecules. More specifically, it includes various environmental factors such as pH, light and temperature, sugars, "borates", alkaline earth metals (e.g. calcium, magnesium, barium, strontium, radium) and transition metals (e.g. iron, copper, cobalt) and other compounds capable of coordinating with the diol (cis-2',3'-diol) of the sugar moiety of the antisense molecule. Even when used singly, these can control the orientation of the base moiety of the antisense molecule of the invention through appropriate adjustment of such factors as their concentration, presence or absence, the pH change, temperature change, intensity of radiation, and wavelength of light. It is also possible to control the orientation of the base moiety of the antisense molecule by means of an arbitrary combination of two or more such factors which act synergistically.

The base moiety orientation control by a combination of, or synergy between, at least two factors can be achieved by an "orientation regulating factor", which regulates the base moiety orientation of the antisense molecule, and an "orientation regulation controlling factor", which controls the orientation regulation by the orientation regulating factor. For example, the orientation regulating factor includes compounds capable of coordinating with the diol of the sugar moiety of the antisense molecule, such as "borates", alkaline earth metals and transition metals among the orientation controlling factors mentioned above. Those compounds coordinate with the sugar moiety diol of the antisense molecule and thereby regulate the base moiety orientation of the antisense molecule. On the other hand, the orientation regulation controlling factor includes such environmental factors as pH, light and temperature as well as sugars among the orientation controlling factors mentioned above. These factors control the binding/dissociation of compounds such as "borates", which are capable of coordinating the diol of the sugar moiety of the antisense molecule, to/from the said diol. Upon changes in pH, light, temperature or sugar conditions (e.g. concentration, presence or absence, pH change, temperature change, light intensity, light wavelength, etc.), the above-mentioned compound is allowed to bind to or dissociate from the diol to thereby control the base moiety orientation of the antisense molecule. Preferred combinations of the orientation regulating factor and orientation regulation controlling factor are "borates" and pH, "borates" and a sugar, "borates" and light, and "borates" and temperature.

The "borates" so referred to herein is not particularly restricted but includes those capable of coordinating with the sugar moiety diol of the antisense molecule, more preferably capable of changing the puckering of the sugar moiety, such as boric acid; salts of boric acid (borates), for example alkali metal salts such as sodium borate (borax); aromatic boric acids including phenylboric acid, naphthylboric acid, anthracenylboric acid and the like and derivatives thereof; as well as various other boric acid derivatives, for example alkylated boric acids such as methylboric acid.

The sugar is not particularly restricted but may be any of those capable of controlling the binding/dissociation of the orientation regulating factor to/from the diol of the antisense molecule sugar moiety. It includes, for example, xylose, glucose, sorbose, N-acetylglucosamine, sialic acid, and glucuronic acid.

As described in detail later herein in the example section, the antisense molecule of the invention can reversibly control the base moiety orientation (syn-anti) under the control of pH or a sugar in the presence of a boric acid. As is known, in cancer cells, for instance, sialic acid is produced abundantly and the acidity is therefore high, namely the environment in an affected site in a patient is under particular conditions different from the normal environment. Therefore, when the antisense molecule of the invention is administered, in combination with an orientation regulating factor such as a boric acid, for instance, to the living body, the base moiety orientation of the antisense molecule can be controlled in response to the change in pH in the in vivo environment and, as a result, the nucleic acid recognition ability or gene function expression can expectedly be controlled. Furthermore, the nucleic acid recognition ability or gene function expression can be controlled by administering the antisense molecule of the invention and an orientation regulating factor in response to the change in sugar concentration in cells in the in vivo environment, like in the case of pH.

The present invention also provides a composition which comprises the antisense molecule of the invention and an orientation regulating factor such as the above-mentioned boric acid, alkaline earth metal or transition metal. The orientation regulating factor is preferably a boric acid. Said composition includes not only simple mixtures of the antisense molecule and an orientation regulating factor but also those embodiments in which the antisense molecule is bound to the orientation regulating factor through a linker according to need.

The present invention also relates to a method for controlling the expression of a gene function which method comprises controlling reversibly the orientation of all or a part of the base moieties contained in the antisense molecule of the invention using the above-mentioned orientation controlling factor (orientation regulating factor, orientation regulation controlling factor) to thereby control the binding of said antisense molecule to a mRNA/gene and/or the dissociation of said antisense molecule from the mRNA/gene. Specific examples of the antisense molecule and of the orientation controlling factor are as mentioned hereinabove. The mechanisms of control will be described in detail later herein in the example section.

The method of introducing the antisense molecule of the invention and an orientation regulating factor such as "borates", alkaline earth metal or transition metal into the living body includes, but is not limited to, the microinjection method, the method utilizing such a drug delivery system as liposomes, and the catheter method, among others. Such orientation regulating factor introduced into the living body is controlled by the change of the orientation regulation controlling factor, such as pH, sugar, or temperature, in the living body and, for example, "borates" bound in vivo to the antisense molecule of the invention is dissociated when it is warmed by local heating on the occasion of thermotherapy, for instance; thereupon, it can switch on the expression of a gene function from the state of off. Light may be mentioned as another example of the orientation regulation controlling factor. When a target site is irradiated with light utilizing a catheter, the action of the orientation regulating factor can be controlled.

EXAMPLES

The following reference examples and working examples illustrate the invention in more detail. However, these examples and so forth are by no means limitative of the scope of the invention. While, in the examples, uracil (pyrimidine base) and inosine (purine base) were mainly used as the base (X) of nucleic acid giving examples of the PRNA, and glutamic acid was mainly used as the amino acid or a derivative thereof (Y, Y'), PRNAs having other bases and amino acids or derivatives thereof can also be used in the same manner.

Example 1

Orientation Control of the 5'-aminouridine Base Moiety Using a Boric Acid and pH as External Factors The orientation of a base moiety is closedly involved in the process of nucleic acid recognition. While highly efficient nucleic acid recognition is possible in the state of the anti orientation, such recognition is almost impossible in the state of the syn orientation. If the anti-syn equilibrium can be controlled arbitrary, it will be possible to control the nucleic acid recognizing ability in the manner shown in FIG. 1.

Therefore, in designing nucleic acid models whose base moiety orientation can be reversibly controlled, attention was paid to the syn orientation induction by a crosslink structure at the 2',3' positions of the sugar moiety of a nucleoside structure. The syn orientation is induced by such crosslink structure at the 2',3' positions of the sugar moiety because the puckering of the furanose moiety takes a 2',3'-planar structure, unlike the 3'-endo-2'-exo structure in ordinary state of a nucleoside.

Thus, the present inventors conceived that if this crosslink structure at the 2',3' positions of the sugar moiety could be formed reversibly, it would become possible to control the orientation of the base moiety in the nucleoside. Therefore, they investigated whether it was possible to control the orientation of the base moiety of a pyrimidine ribonucleoside using boric acids, which are able to reversibly form a borate ester bond with the cis-diol group in the sugar moiety of nucleosides in aqueous solution.

(1) Effects of "Borates" on the Orientation of the 5'-aminouridine Base Moiety (pH 7.2)

(1-1) Investigations Using Circular Dichroism Spectra

Figure 2:
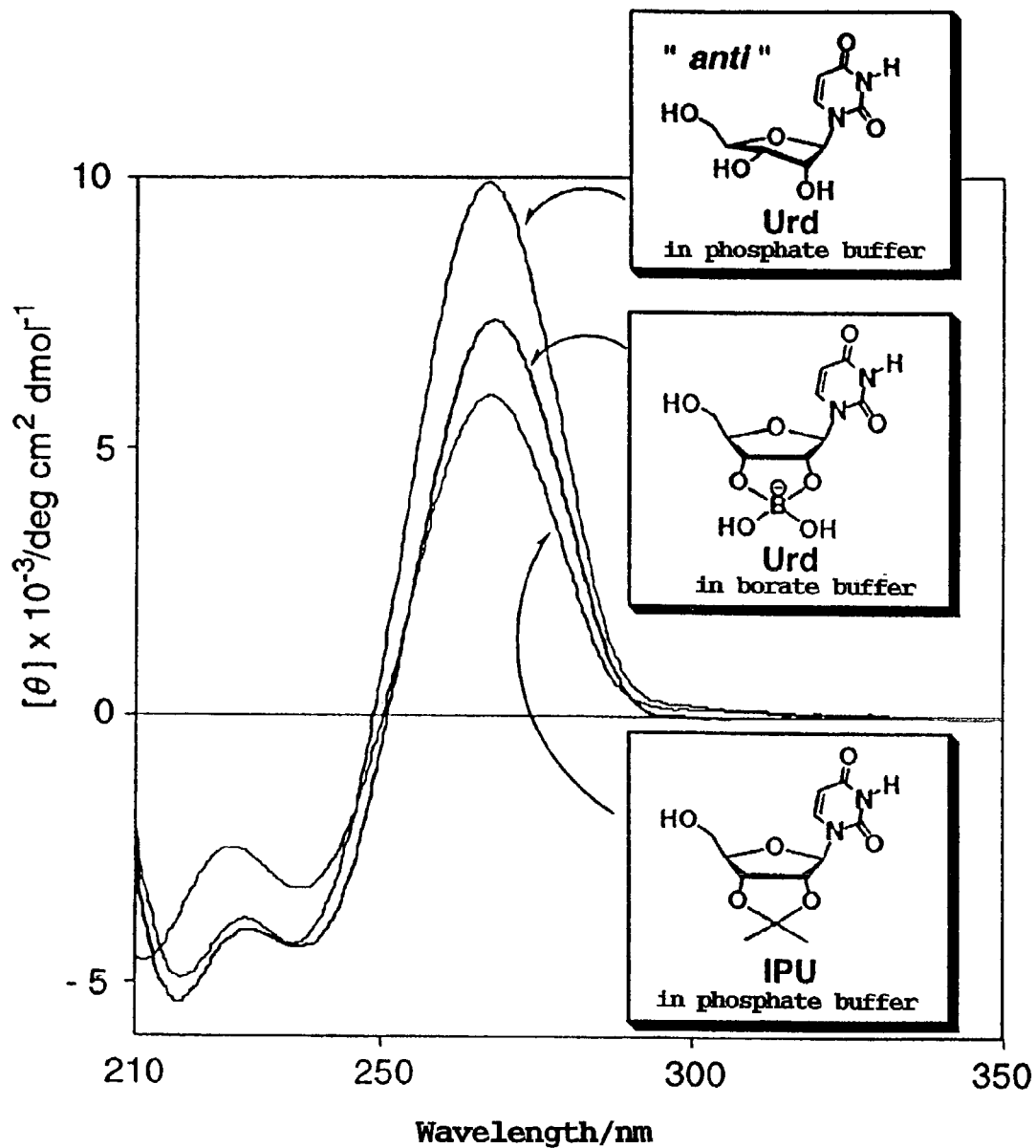
FIG. 2 is a representation of the results of circular dichroism (CD) spectrum measurements of uridine (Urd) and isopropylideneuridine (IPU) in phosphate buffer (pH 7.2) and of uridine (Urd) in borate buffer (pH 7.2) in Example 1 (1) (1-1).

The molar ellipticity ([θ]max) at about 270 nm in the CD spectrum of a nucleoside reflects two factors, namely the orientation of the base moiety to the furanose moiety and the puckering of the furanose ring. It is known that the molar ellipticity at about 270 nm markedly decreases in the syn orientation as compared with the anti orientation. Therefore, CD spectra were measured with uridine (Urd) and with isopropylideneuridine (IPU) having a crosslink structure at the 2',3' positions of the sugar moiety in phosphate buffer with a pH of 7.2 (1/30 M $KH_2PO_4$ and 1/30 M $Na_2HPO_4$). The results are shown in FIG. 2. From these results, it was revealed that the proportion of the syn orientation increases upon formation of a crosslink structure at the 2',3' positions of the sugar moiety, since the [θ]max observed for IPU was smaller as compared with Urd.

Then, a CD spectrum of Urd was measured in borate buffer with a pH of 7.2 (1/10 M $KH_2PO_4$ and 1/20 M $Na_2B_4O_7$). As shown in FIG. 2, the results revealed that the [θ]max value decreases and the proportion of the syn orientation increases in borate buffer as compared with the case in phosphate buffer. This suggests that the borate ester formation at the 2',3' positions of the sugar moiety and the resulting conversion of the puckering of the furanose moiety to 2',3'-planar induced the syn orientation. The rate of syn orientation induction in Urd in the presence of boric acid was smaller as compared with IPU but this can be explained by the presence of an equilibrium between the borate ester formation and the dissociation.

Figure 3:
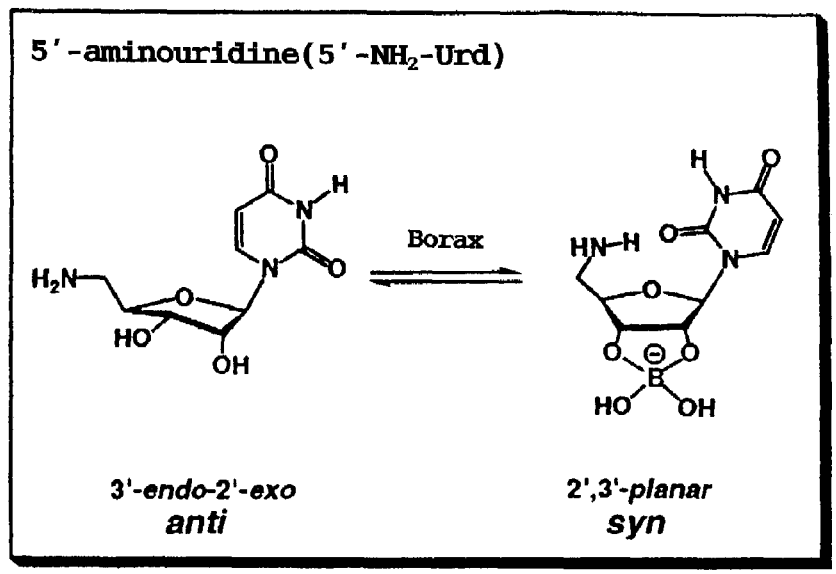
FIG. 3 is an illustration showing that the syn orientation of 5'-aminouridine (5'-NH$_2$-Urd) is induced by the synergy between a borate aster bond and an intramolecular hydrogen bond.

As shown with Urd, no efficient orientation regulation can be attained by the borate ester bond formation alone. Therefore, as shown in FIG. 3, investigations were made with models in which the syn orientation can be induced by intramolecular hydrogen bonding.

Figure 4:
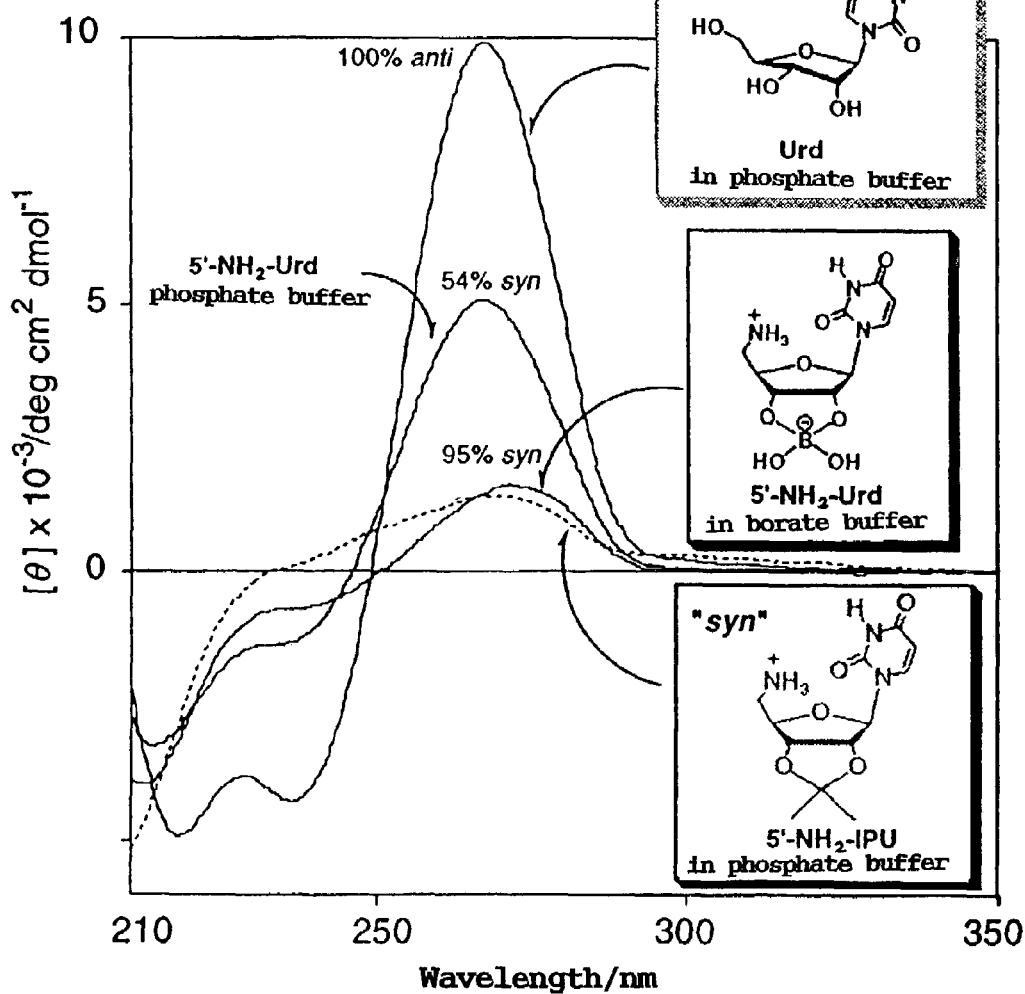
FIG. 4 is a representation of the results of CD spectrum measurements of Urd, 5'-NH$_2$-Urd and 5'-amino-isopropylideneuridine (5'-NH$_2$-IPU) in phosphate buffer (pH 7.2) and of 5'-NH$_2$-Urd in borate buffer (pH 7.2) in Example 1 (1) (1-1).

Specifically, CD spectra were measured with Urd, 5'-aminouridine (5'-$NH_2$-Urd) and 5'-aminoisopropylideneuridine (5'-$NH_2$-IPU) in phosphate buffer (pH 7.2) and with 5'-$NH_2$-Urd in borate buffer (pH 7.2) for the investigation of uracil moiety orientations. The results, shown in FIG. 4, revealed that the [θ]max value for 5'-$NH_2$-Urd in phosphate buffer is small as compared with Urd under the same conditions, indicating an increase in rate of syn orientation. This is presumably due to a syn orientation-inducing effect of hydrogen bond formation between the oxygen atom of the 2-position carbonyl group of the nucleoside base moiety and the 5'-position amino hydrogen atom. Under the measurement conditions in this case, the 5'-position amino group of 5'-$NH_2$-Urd occurs in an ammonium ion state and presumably serves as a good hydrogen bond donor. Further, as shown in FIG. 4, the [θ]max value becomes very small when measured with 5'-$NH_2$-IPU, used in lieu of 5'-$NH_2$-Urd, in phosphate buffer or when measured with 5'-$NH_2$-Urd in borate buffer, indicating that the syn orientation predominates in these base moieties. This is probably due to two synergistic effects, namely the fixation of the sugar moiety to the 2',3'-planar structure and the hydrogen bond formation between the 5'-position amino group and the 2-position carbonyl group of the base moiety.

Then, on the supposition that Urd in phosphate buffer ([θ]max value=9700) is in an ideal 100% anti orientation and 5'-$NH_2$-IPU in phosphate buffer ([θ]max value=1200) in an ideal 100% syn orientation, the orientations of the base moiety (uracil) of uridine and uridine derivatives (5'-$NH_2$-Urd, IPU, 5'-$NH_2$-IPU) were evaluated under different conditions (in phosphate buffer, in borate buffer). The results are shown in Table 1.

TABLE 1

| Compound | [θ]$_{max}$/deg $cm^2 dmol^{-1}$ | |
|---|---|---|
| | Phosphate buffer | Borate buffer |
| Urd | 9700 (100% anti) | 7400 (27% syn) |
| 5'-$NH_2$-Urd | 5100 (54% syn) | 1600 (95% syn) |
| IPU | 6000 (44% syn) | — |
| 5'-$NH_2$-IPU | 1200 (100% syn) | — |

From the above results, it was revealed that the syn orientation predominates in 5'-$NH_2$-Urd in the presence of boric acid with very good efficiency. A similar change in orientation was also found with 5'-amino-5'-deoxycytidine (5'-$NH_2$-Cyd).

TABLE 2

| Compound | [θ]$_{max}$/deg $cm^2 dmol^{-1}$ | |
|---|---|---|
| | Phosphate buffer | Borate buffer |
| Cytidine (Cyd) | 14200 | 12200 |
| 5'-$NH_2$-Cyd | 8400 | 4900 |

Figure 5:
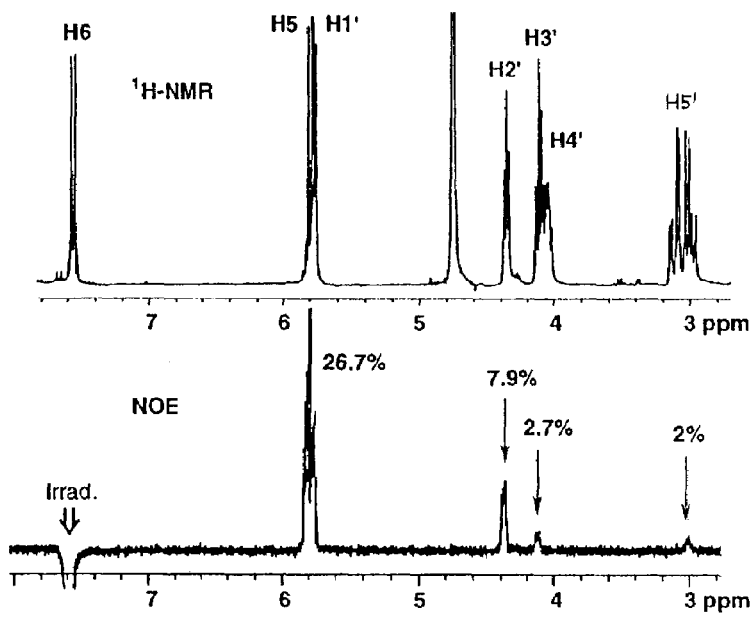
FIG. 5 is a representation of the results of $^1$H-NMR and NOE (nuclear Overhauser effect) spectrum measurements made, in Example 1 (1) (1-2), for examining the orientation of the base moiety of 5'-NH$_2$-Urd proton-irritated at the position 6 of the base moiety in phosphate buffer (pH 7.2) (FIG. 5a) and in borate buffer (pH 7.2) (FIG. 5b).
Figure 5:
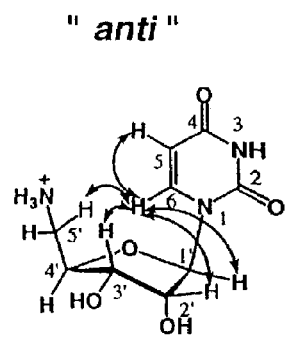
Figure 5:
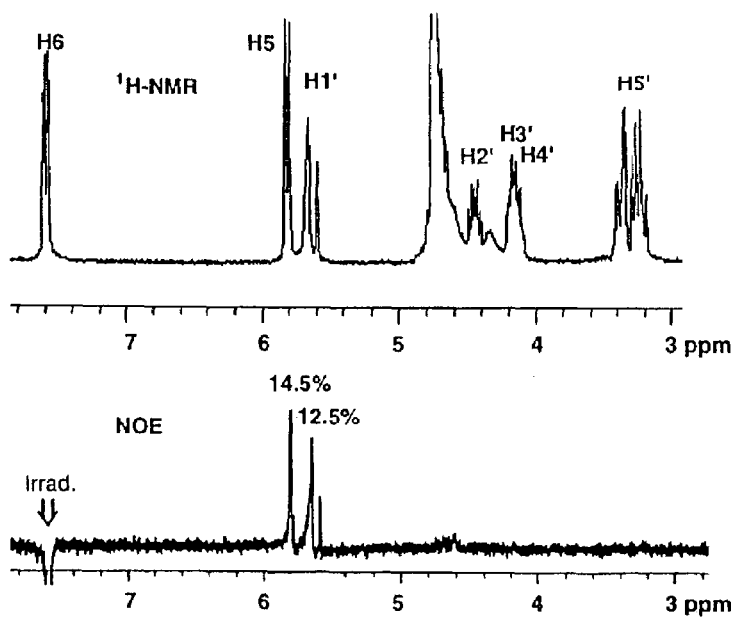
Figure 5:
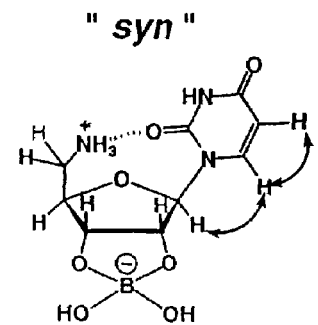

The orientations of the base moiety of 5'-$NH_2$-Urd in the absence of "borates" and in the presence of "borates" were further investigated using NMR difference NOE measurements. The results are shown in FIG. 5. For 5'-$NH_2$-Urd in phosphate buffer, the NOE was observed not only at positions 5 and 1' but also at positions 2',3' and 5' upon proton irradiation at position 6 of the base moiety. This results indicates that the anti orientation is predominant in the base moiety. On the other hand, upon the same irradiation at position 6 in borate buffer, the NOE was observed at positions 5 and 1' but not observed at positions 2',3' or 5'. This result indicates that the syn orientation is predominant in the base moiety.

Thus, from the results of NMR difference NOE measurements as well, it was revealed that when "borates" is used, the orientation of the base moiety of 5'-$NH_2$-Urd can be changed from anti to syn with good efficiency.

Figure 6:
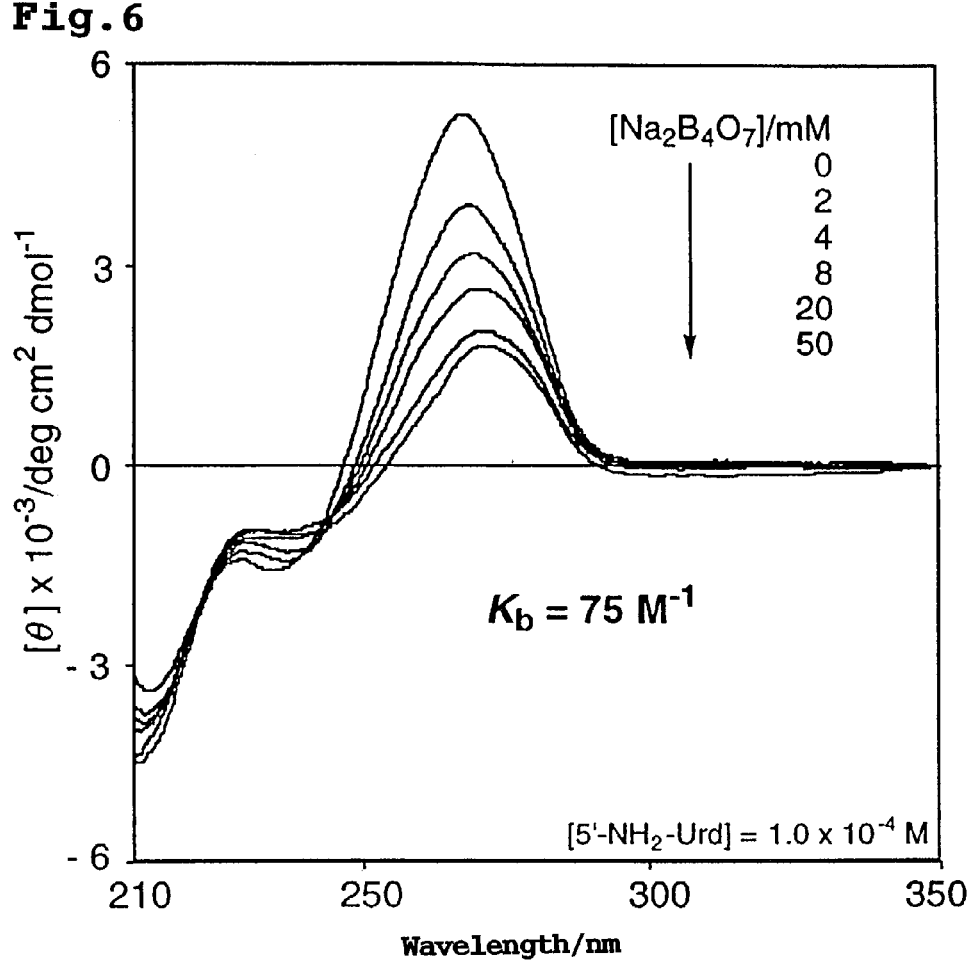
FIG. 6 is a representation of the results obtained upon examination, in Example 1 (2) (2-1), of changes in CD spectrum of 5'-NH$_2$-Urd as resulting from addition of borax (0 to 50 mM) to phosphate buffer (pH 7.2).

(2) Multifactor Control of the Base Moiety Orientation of 5'-aminouridine Using "Borates" and pH (2-1) Effect of pH on Orientation Regulation of the Base Moiety of 5'-aminouridine In the above examples, it was revealed that the syn orientation is predominant in 5'-$NH_2$-Urd in the presence of "borates". However, there is no direct evidence as yet that this change in base moiety orientation is induced by borate ester bond formation. Therefore, the dependency of the change in base moiety orientation on the concentration of borax ($Na_2B_4O_7$) was investigated at pH 7.2. The results are shown in FIG. 6. From the results, it was revealed that, with the increase in borax concentration, decreases in [θ]max value are observed and the base moiety orientation changes from anti to syn. The association constant of 5'-$NH_2$-Urd with boric acid was determined by plotting the decrement in peak height against the boric acid (borax) concentration, followed by curve fitting. Supposing that borax give 4 equivalents of boric acid in aqueous solution, the association constant of 5'-$NH_2$-Urd with boric acid was calculated at 75 $M^{-1}$.

Figure 7:
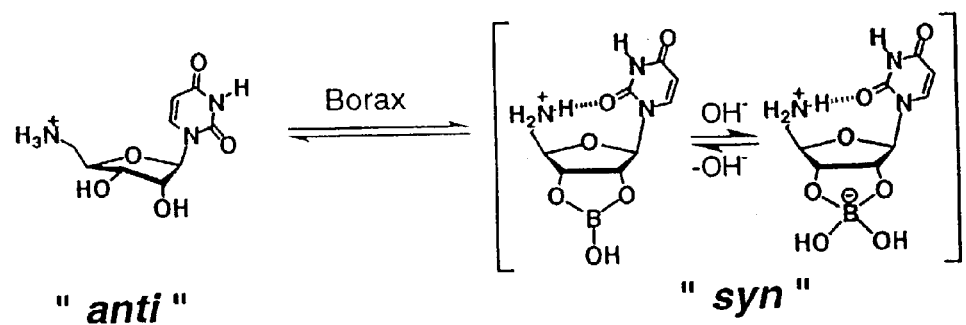
FIG. 7 is an illustration showing the change in orientation (anti→syn) in the base moiety of 5'-NH$_2$-Urd as resulting from borate ester bond formation.

From the above findings, it was revealed that the change in orientation of the base moiety from anti to syn is accomplished by borate ester bond formation (FIG. 7).

In addition to the above-mentioned borax, boric acid ($B(OH)_3$) was also used and the addition test was carried out in the same manner. In this case, too, decreases in peak height were observed, and the association constant was calculated at 49 $M^{-1}$. In addition, changes in orientation due to ester formation were also observed with methylboric acid and phenylboric acid.

Figure 8:
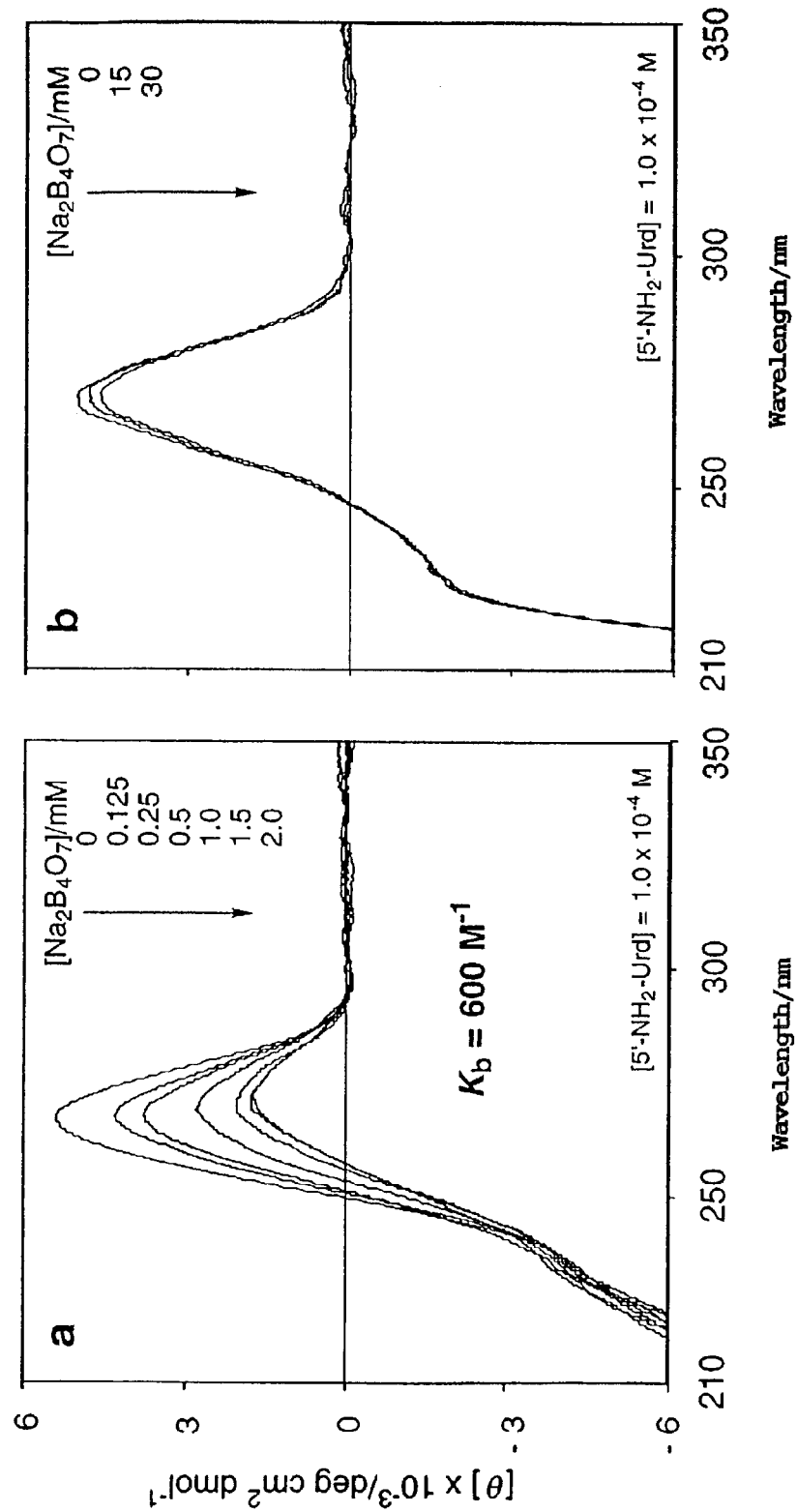
FIG. 8 is a representation of the results obtained upon examination, in Example 1 (2) (2-1), of changes in CD spectrum of 5'-NH$_2$-Urd as resulting from addition of borax to the phosphate buffer (pH 8.8) (FIG. 8a) and phosphate buffer (pH 6.0) (FIG. 8b).

Meanwhile, it is known that pH is deeply involved in borate ester formation. As shown in FIG. 7, stable tetravalent borate esters are formed at high pH, while unstable trivalent borate esters are formed at low pH. It is thus considered that the equilibrium shifts in the direction of ester dissociation at low pH. Therefore, borax addition experiments were carried out at pH 8.8 and pH 6.0. The results are shown in FIG. 8.

As is evident from FIG. 8a, almost the same change as that attained by addition of 50 mM of borax at pH 7.2 was obtained at pH 8.8 only by addition of 2 mM of borax. It was thus revealed that the syn orientation is induced more effectively at pH 8.8 as compared with pH 7.2. The association constant 5'-$NH_2$-Urd with boric acid was calculated at 600 $M^{-1}$, which is greater by one order than at pH 7.2. On the other hand, at pH 6.0, almost no peak decreases were observed even upon addition of 30 mM of borax and no orientation change occurred in the base moiety (FIG. 8b). These results can be explained by the pH-dependent stability of borate esters.

Figure 9:
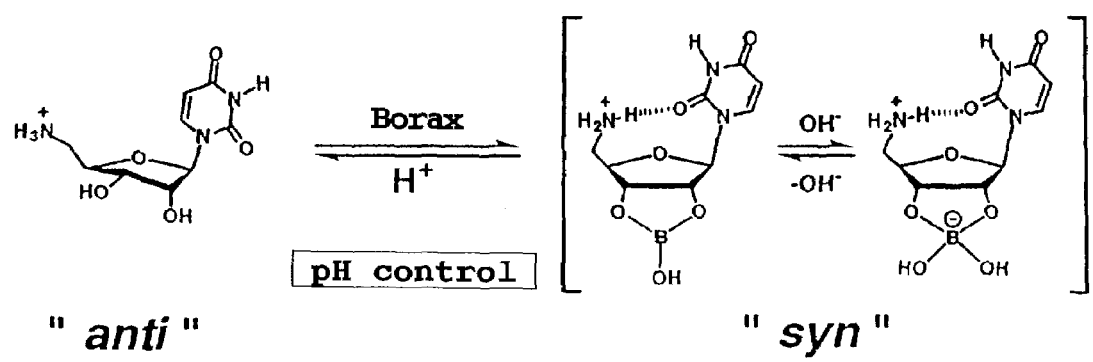
FIG. 9 is an illustration showing the mode of reversible control of the base moiety orientation of 5'-NH$_2$-Urd as resulting from pH changes in the presence of borax in Example 1 (2) (2-1).

In view of the foregoing, it became apparent that the base moiety orientation regulation by the addition of borax is controlled in a pH-dependent manner. This suggests the possibility of reversible multifactor control of the base moiety orientation by using "borates" as an orientation regulating factor and pH as an orientation regulation controlling factor, as shown in FIG. 9.

Figure 10:
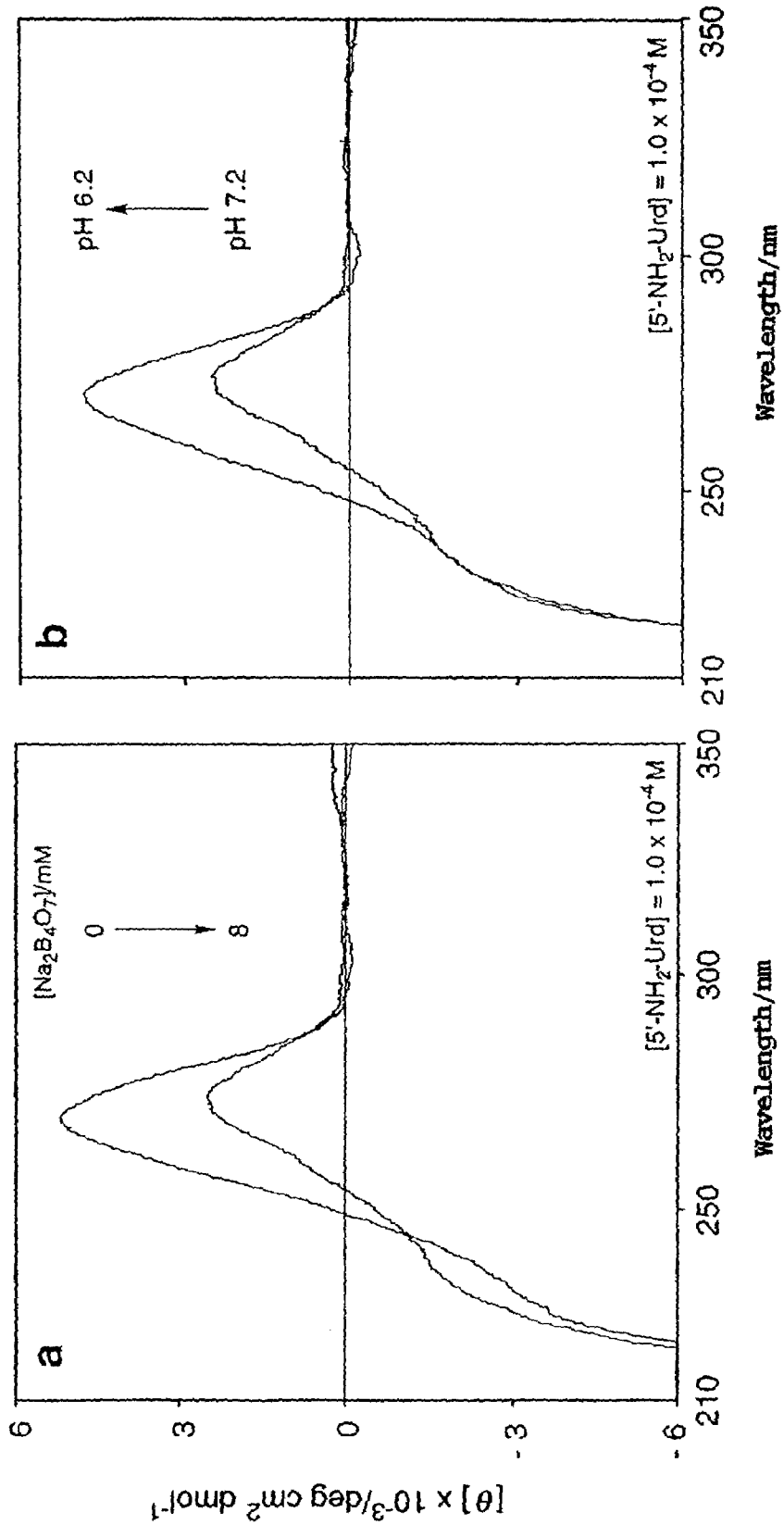
FIG. 10 is a representation of the results obtained upon examination, in Example 1 (2) (2-2), of changes in CD spectrum of 5'-NH$_2$-Urd following addition of borax (8 mM) (FIG. 10a), followed by pH control (FIG. 10b).

(2-2) Reversible Orientation Control of the Base Moiety of 5'-aminouridine Using a "Borates" as an Orientation Regulating Ractor and pH as an Orientation Regulation Controlling Factor Based on the above results, an investigations using CD spectra was made to check as to whether the orientation of the base moiety (uracil group) of 5'-$NH_2$-Urd can be reversibly controlled by using borax as an orientation regulating factor and pH as an orientation regulation controlling factor. The results are shown in FIG. 10. As is evident from FIG. 10a, the peak at about 270 nm decreased and the change in orientation from 55% syn to 83% syn was observed when 8 mM of borax was added to 5'-$NH_2$-Urd in phosphate buffer at pH 7.2. Then, when the pH of this borax-added system was adjusted from 7.2 to 6.2, the peak at about 270 nm increased and the orientation of the base moiety changed to 58% syn, namely the proportion of anti orientation increases (FIG. 10b).

Figure 11:
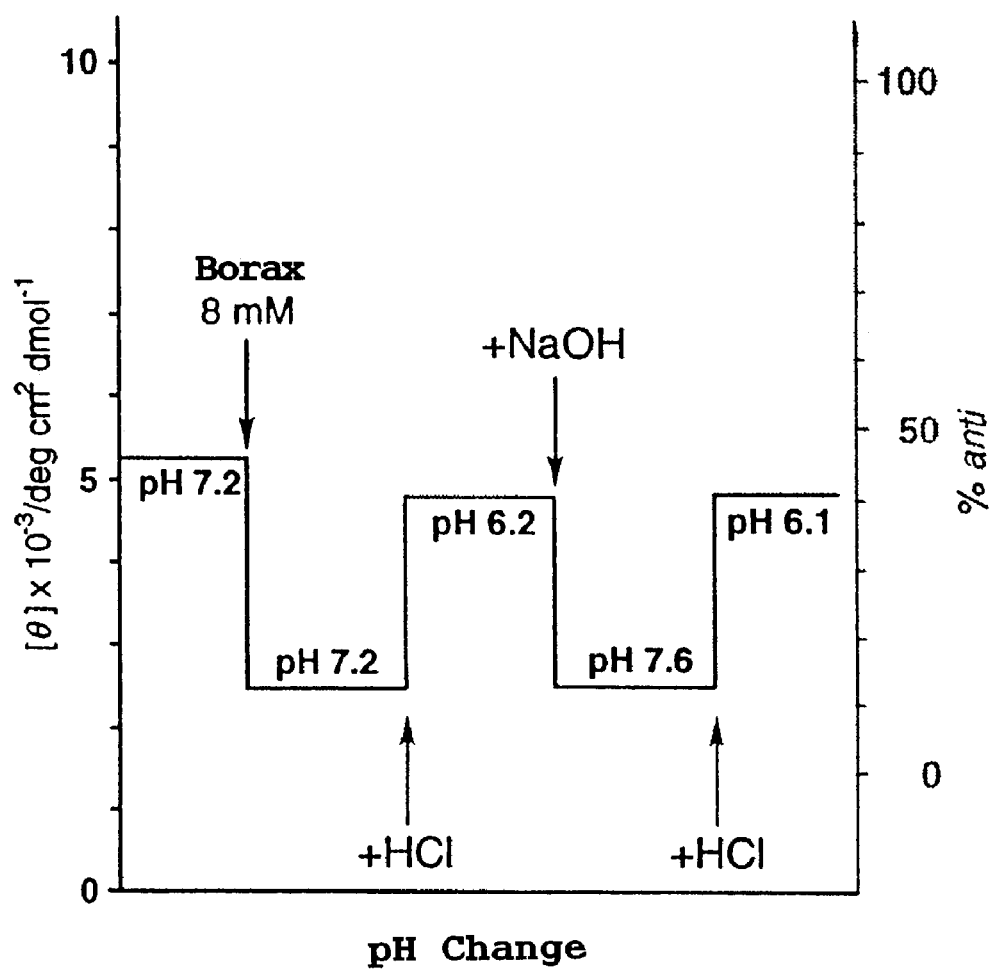
FIG. 11 is a representation of changes in molar ellipticity ([θ]max) of 5'-NH$_2$-Urd upon addition of borax and changes in pH.

Further, in succession, the pH of this system was adjusted to 7.6, whereupon the syn orientation was again induced and, when the pH was adjusted to 6.1, the anti orientation was again induced (FIG. 11).

From the above results, it was revealed that the base moiety orientation of 5'-$NH_2$-Urd can be reversibly controlled by using borax as an orientation regulating factor and pH as an orientation regulation controlling factor.

(2-3) Reversible Control of the Base Moiety Orientation of a PRNA2 (Octamer) Using "Borates" as an Orientation Regulating Factor and pH as an Orientation Regulation Controlling Factor As is seen from the results mentioned above, the 2',3' cis-diol capable of forming a borate ester bond in the sugar moiety, the 2-position carbonyl group in the base moiety and the 5'-position amino hydrogen atom capable of hydrogen bonding with the oxygen atom of said carbonyl group are required for the change in base moiety orientation of 5'-$NH_2$-Urd. The PRNAs ((poly)amino acid ribonucleic acid and peptide ribonucleic acid) of the present invention are new-category nucleic acid models resulting from introduction of a 5'-$NH_2$-nucleoside, preferably a 5'-$NH_2$-5'-deoxynucleoside, into a peptide chain without impairing such functional groups necessary for orientation control.

Accordingly, the octamer (compound 17), which is a PRNA2, prepared in Production Example 3 (2) was used as a PRNA, and the ability thereof to form complexes with a nucleic acid (oligonucleotide) was examined and whether said complex formation can be controlled by boric acids was also examined.

Specifically, the PRNA2 (octamer) (17) was mixed with the oligonucleotide octamer shown in Table 3, the melting point (Tm) was determined by measuring the resulting change in absorbance on a UV spectrum, and the ability of the PRNA2 (octamer) (17) to hybridize with a nucleic acid (complex forming ability) was evaluated from that melting point. Further, for examining the influence of boric acids on the PRNA2 (octamer)-DNA hybrid formation and on the stability thereof, melting point measurements were carried out using the PRNA2 (octamer) (17) and $d(A)_8$ as the binding target oligonucleotide to the PRNA2, namely a complementary compound to $(T)_8$, with and without addition of borax (20 mM), and the melting points were compared. The results are shown in Table 3. A control run was carried out in the same manner using $(T)_8$ as the binding target oligonucleotide in lieu of $d(A)_8$.

TABLE 3

| PRNA2 (octamer), or Oligodeoxyribonucleotide | Binding target compound | Tm/° C. Additive | |
|---|---|---|---|
| | | Non | 20 mM Borax |
| PRNA2 (17) | $d(A)_8$ | 52.8 | <0 |
| PRNA2 (17) | $(T)_8$ | <0 | <0 |
| $(T)_8$ | $d(A)_8$ | 45 | 56.9 |

Solvent: Phosphate(0.033 M $KH_2PO_4$-0.033 M $Na_2HPO_4$, pH 7.2)

From the above results, it was found that the PRNA2 (octamer) (17) interacts specifically with $d(A)_8$, which is an oligonucleotide complementary thereto. In a buffer solution without addition of borax, the PRNA2 (octamer) and $d(A)_8$ formed a complex having a melting point of 52.8° C., which was significantly higher than the melting point (45° C.) of the $(T)_8$-$d(A)_8$ complex. This indicates that the PRNA 2 (octamer) shows a stronger interaction with bases of nucleic acid in the system without addition of borax, as compared with the case of a natural nucleic acid.

On the other hand, in a borax-containing buffer solution, the melting point of $(T)_8$-$d(A)_8$ was 56.9° C., the PRNA2 (octamer) gave a melting point below 0° C.; no complex formation was observed. It was thus found that the complex formed in the above system is dissociated by the addition of borax.

Figure 12:
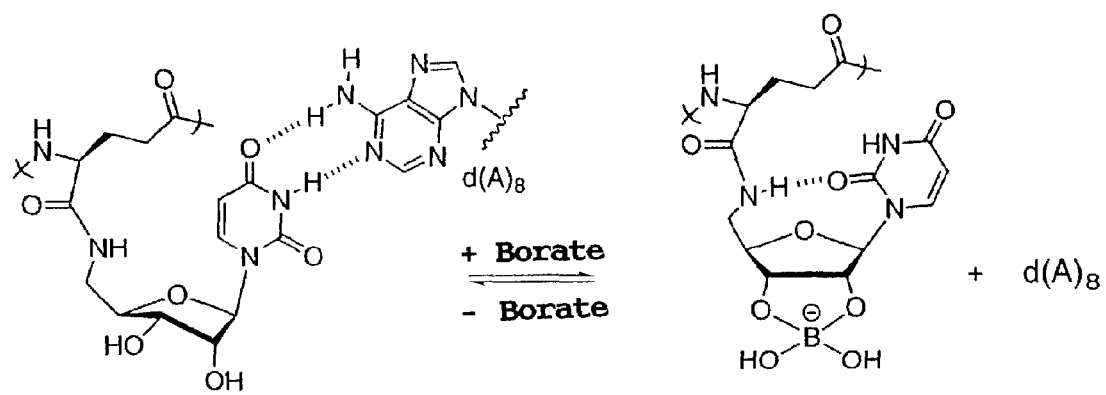
FIG. 12 is an illustration showing the change in orientation of the uracil base moiety of PRNA2 (octamer) in the presence and absence of a borate salt and the formation of a complex between the same and a complementary oligonucleotide d(A)$_8$, as measured in Example 1 (2) (2-3).

Such contrary behaviors of the PRNA2 (octamer) in the absence of a borate and in the presence of a borate are presumably due to the anti-to-syn orientation switching in the uracil base moiety. It is also presumable that such orientation switching is attained by synergy between the borate ester bond formation at the cis-2',3'-diol site of sugar moiety in the nucleoside and the hydrogen bond formation between the oxygen atom of the 2-position carbonyl group of base moiety in the nucleoside and the 5'-amino group (cf. FIG. 12).

Example 2

Multifactor Control of the Base Moiety Orientation of AEG (5'U) Using "Borates" and pH (1) Base Moiety Orientation Regulation of AEG(5'U) Using "Borates" at pH 7.2

As has been revealed in Example 1, the base moiety orientation of 5'-$NH_2$-Urd can be reversibly controlled using "borates" and pH. Therefore, the possibility of the same reversible control of base moiety orientation for AEG(5'U) having 5'-$NH_2$-Urd as the recognition site was examined by CD spectrum and $^1$H-NMR difference NOE measurements.

Figure 13:
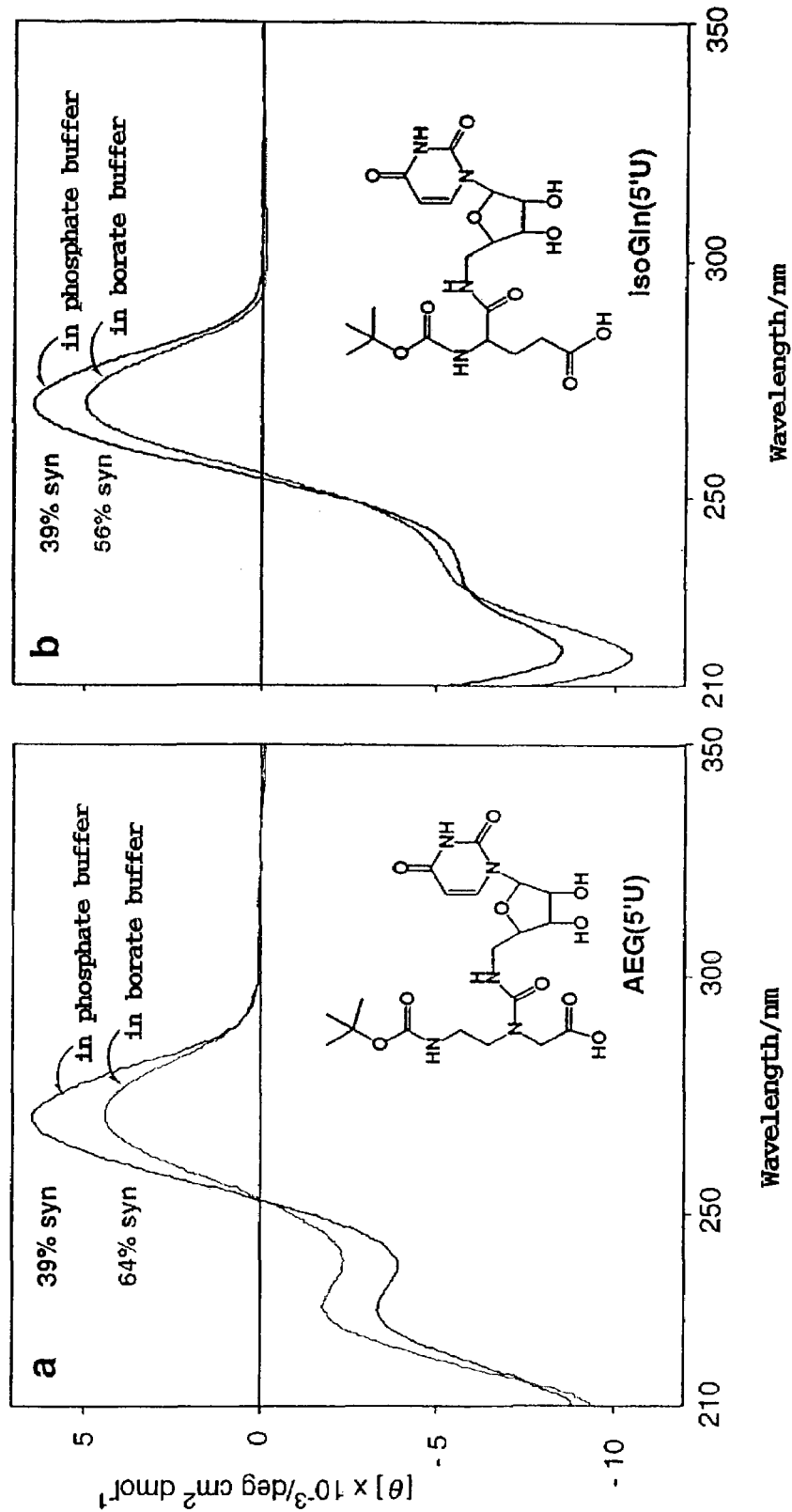
FIG. 13 is a representation of the results of CD spectrum measurements, in Example 2 (1), of Boc-AEG(5'U)-OH (FIG. 13a) and Boc-isoGln(5'U)-OH (FIG. 13b) in phosphate buffer (pH 7.2) and borate buffer (pH 7.2).

CD spectra of Boc-AEG(5'U)-OH (Production Example 5 (3)) were measured in phosphate buffer and borate buffer. The results are shown in FIG. 13a. Here, the peak at about 270 nm reflects the base moiety orientation. It was revealed that the anti orientation is predominant (39% syn) in the base moiety in phosphate buffer, while the proportion of the syn orientation increases to 64% syn in borate buffer. This induction of syn orientation in the presence of boric acid is presumably due to the borate ester bond formation at the 2',3' positions of the sugar moiety.

Figure 14:
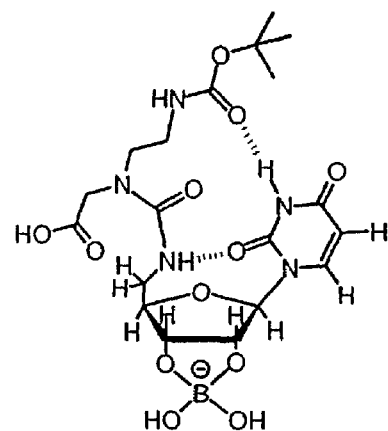
FIG. 14 is an illustration showing a probable estimated structure of Boc-AEG(5'U)-OH in borate buffer.

CD spectrum measurements were carried out in the same manner for a PRNA2 monomer (Boc-isoGln(5'U)-OH) (Production Example 2 (2)). The results are shown in FIG. 13b. As is evident from the figure, an increase in syn orientation percentage (56% syn) was observed in the presence of boric acid but this change in orientation was smaller as compared with the above-mentioned AEG(5'U). As the reasons for this difference between the two monomers, there may be mentioned the difference in peptide chain bulkiness, the difference in hydrophobicity, and the difference in acidity of the 5'-position amide proton, among others. As a factor influencing the syn orientation induction efficiency, there may be mentioned a second intramolecular hydrogen bond occurring in AEG(5'U) syn and supporting orientation induction (FIG. 14). This is also supported by the fact that the chemical shifts, in $^1$H-NMR, of the 5-position and 6-position protons in the base moiety of AEG(5'U) show high magnetic field shifting in borate buffer as compared with those in phosphate buffer (Table 4).

TABLE 4

| | δ/ppm | | |
|---|---|---|---|
| | Phosphate buffer | Borate buffer | Δδ/ppm |
| H5 | 5.75 | 5.71 | −0.04 |
| H6 | 7.56 | 7.47 | −0.09 |

The relatively small change in orientation due to boric acid as compared with the case of 5'-NH$_2$-Urd is probably due to a decrease in hydrogen bond forming ability as resulting from the fact that the position 5' in the monomer is not in the state of ammonium ion.

Figure 15:
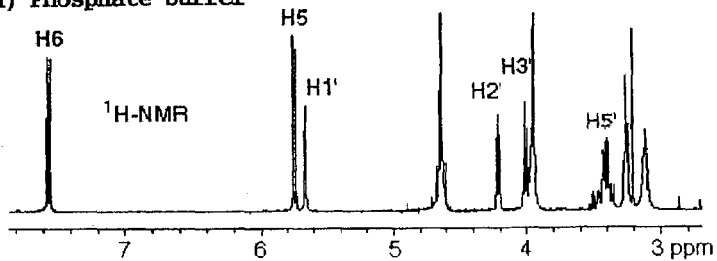
FIG. 15 is a representation of a $^1$H-NMR spectrum (FIG. 15a) of Boc-AEG(5'U)-OH in phosphate buffer (pH 7.2) and NOE spectra of Boc-AEG(5'U)-OH proton-irradiated at the position 6 of the base moiety in phosphate buffer (pH 7.2) (FIG. 15b) and borate buffer (pH 7.2) (FIG. 15c), as measured in Example 2 (1).
Figure 15:
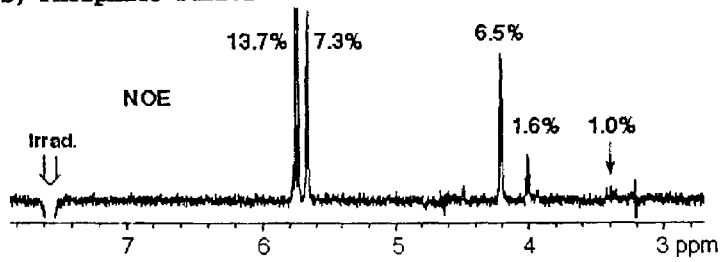
Figure 15:
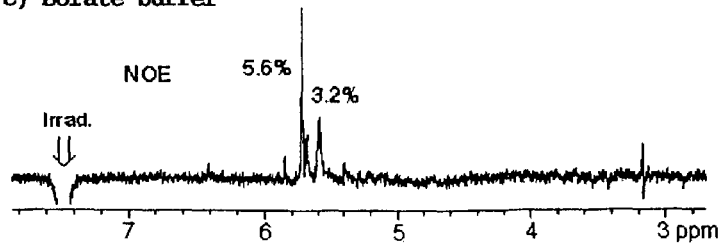

The base moiety orientation of AEG(5'U) was also examined using $^1$H-NMR difference NOE measurements. The results are shown in FIG. 15. Upon irradiation of the uracil base 6-position in phosphate buffer, the NOE was observed at positions 5 and 1' and further at positions 2', 3' and 5', revealing the predominance of the anti orientation. In borate buffer, on the other hand, the NOE was observed only at positions 5 and 1' upon irradiation of position 6, revealing the predominance of the syn orientation. These results are in agreement with the results of CD spectrum measurements.

The above results revealed that the base moiety orientation of AEG(5'U) can be changed from the anti orientation to the syn orientation with good efficiency by using of "borates" as an external factor.

Figure 16:
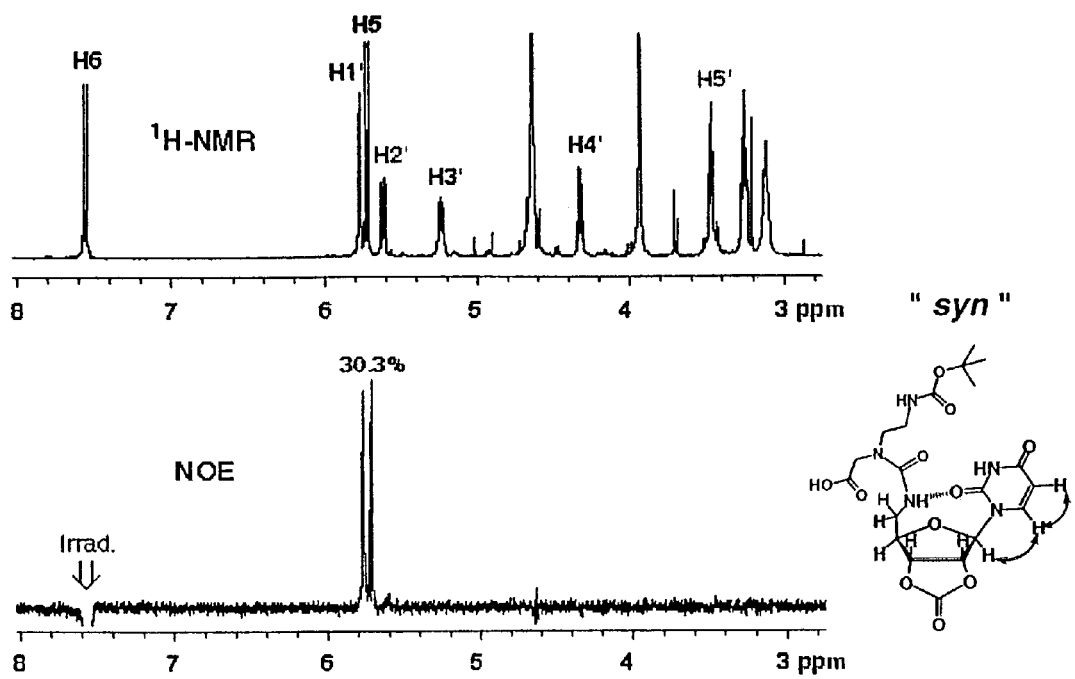
FIG. 16 is a representation of a $^1$H-NMR spectrum and a NOE spectrum of Boc-AEG(5'cU-carboante)-OH in phosphate buffer (pH 7.2) as measured in Example 2 (1).

The base moiety orientation of Boc-AEG(5'cU)-carbonate)-OH having a crosslink structure at the 2',3' positions of the sugar moiety in the nucleoside (sugar moiety) was also examined in the same manner by $^1$H-NMR difference NOE measurements. The results are shown in FIG. 16. Upon irradiation of the uracil base 6 position in phosphate buffer, the NOE was observed at only positions 5 and 1', revealing the predominance of the syn orientation. From this finding, too, it is evident that there is a close relationship between the crosslink structure at the sugar moiety 2',3' positions and the base moiety orientation and, in particular when hydrogen bonding is possible between the base moiety 2-position carbonyl group and the 5'-amino group, the overwhelming predominance of the syn orientation is induced by the crosslink structure.

(2) Effects of pH on the Orientation Regulation of the Base Moiety of AEG(5'U)

Figure 17:
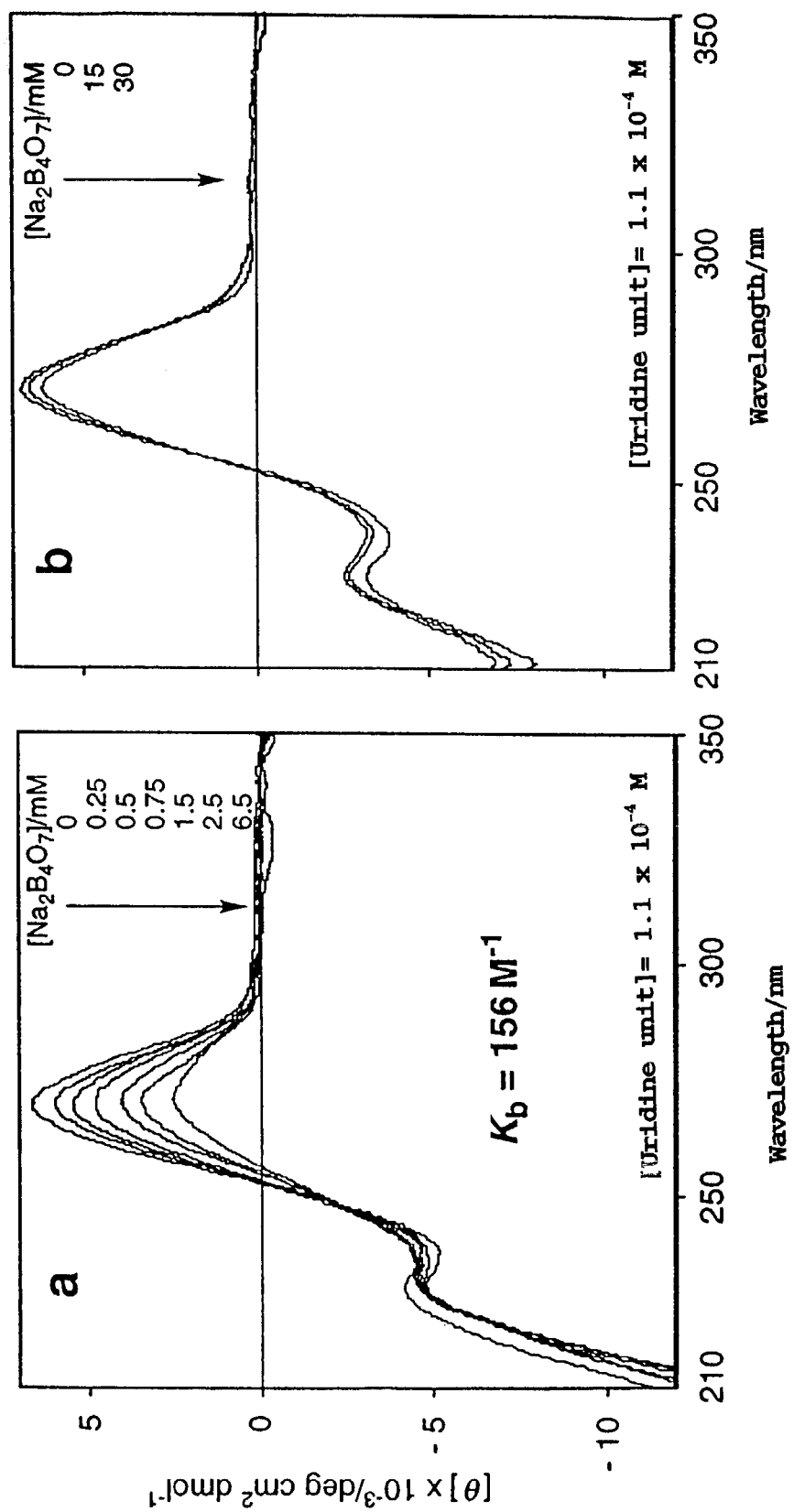
FIG. 17 is a representation of the results of examination, in Example 2 (2), of the changes in CD spectrum of Boc-AEG (5'U)-OH as resulting from addition of borax to the phosphate buffer (pH 8.8) (FIG. 17a) and phosphate buffer (pH 6.0) (FIG. 17b).
Figure 18:
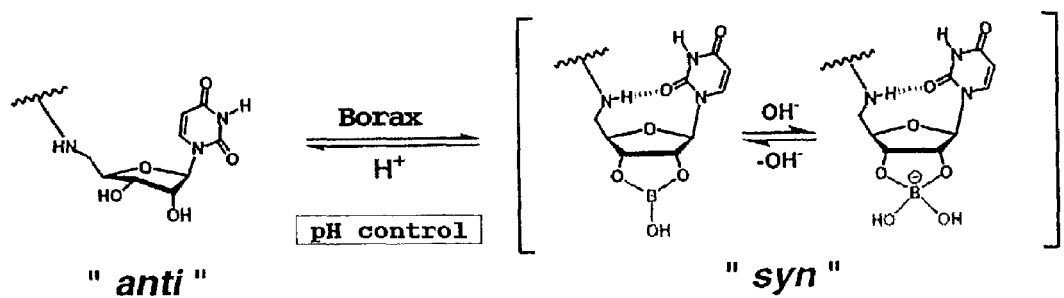
FIG. 18 is an illustration showing that the orientation of the base moiety of Boc-AEG(5'U)-OH is reversibly controlled by the change in pH in the presence of borax.

The changes in base moiety orientation of Boc-AEG(5'U)-OH (Production Example 4 (3)) at pH 8.8 and pH 6.0 in the presence of "borates" were examined using CD spectra. The results are shown in FIG. 17. As can be seen from the figure, the peak at about 270 nm decreased upon addition of borax at pH 8.8, like in the case of 5'-NH$_2$-Urd, and a very efficient increase in syn orientation proportion was thus observed (FIG. 17a), whereas, at pH 6.0, almost no decrease in the relevant peak was observed, hence no change in orientation occurred upon addition of borax (FIG. 17b). These results can be explained by the pH-dependent stability of the borate ester formed at sugar moiety.

The above results revealed that, even in the PRNA monomer (amino acid ribonucleic acid), the base moiety orientation control by the addition of borax is dependent on pH. Therefore, it is estimable that the base moiety orientation of Boc-AEG(5'U)-OH can be reversibly controlled by a boric acid as an orientation regulating factor and pH as an orientation regulation controlling factor (multifactor control).

(3) Reversible Orientation Control of the Base Moiety of AEG(5'U) by "Borates" as an Orientation Regulating Factor and pH as an Orientation Regulation Controlling Factor (CD Spectrum-based Investigations)

Figure 19:
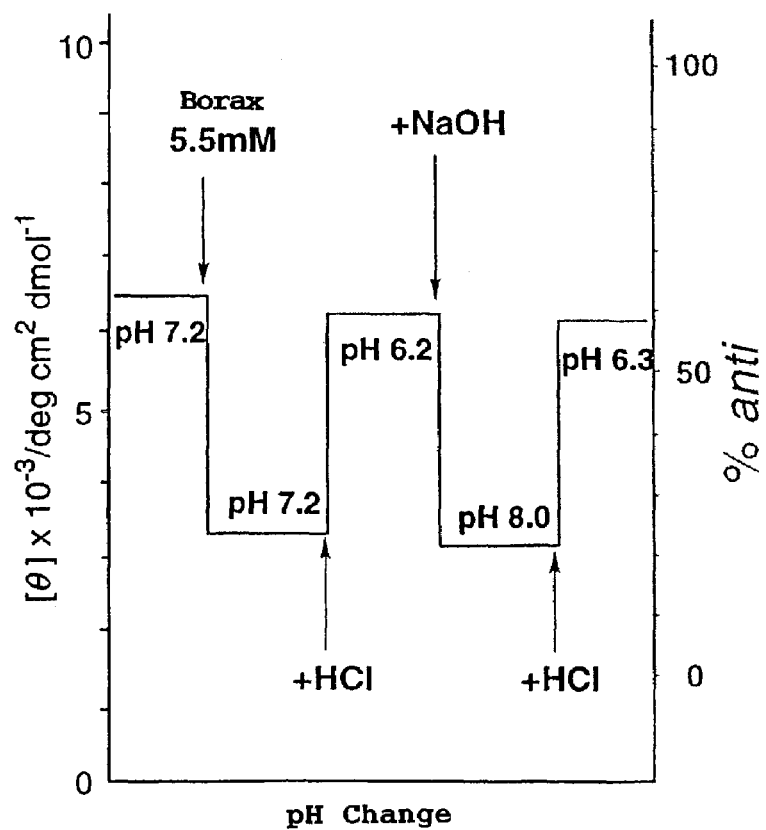
FIG. 19 is a representation of the changes in molar ellipticity ([θ]max) of Boc-AEG(5'U)-OH upon the addition of borax and upon changes in pH.

CD spectrum-based investigations were carried out to check as to whether the above-estimated reversible orientation control of the base moiety of AEG(5'U) by borax as an orientation regulating factor and pH as an orientation regulation controlling factor is actually possible or not. The changes in [θ]max value of AEG(5'U) as found upon pH adjustment following the addition of borax are shown in FIG. 19. Upon addition of 5.5 mM of borax to AEG(5'U) in phosphate buffer at pH 7.2, the [θ]max value decreased and a change orientation from 39% syn to 76% syn was observed. Then, the pH of this borax-containing system was adjusted from 7.2 to 6.2, whereupon the anti orientation percentage increased and 41% syn was observed. Thereafter, induction of the syn orientation was observed upon adjustment to high pH, and induction of the anti orientation upon adjustment to low pH, revealing that the base moiety orientation of AEG(5'U) can be reversibly controlled using boric acid as an orientation regulating factor and pH as an orientation regulation controlling factor. It is considered that the ability to form a complex with a target mRNA/gene (nucleic acid sequence) can be modulated by controlling this base moiety orientation.

Example 3

Figure 20:
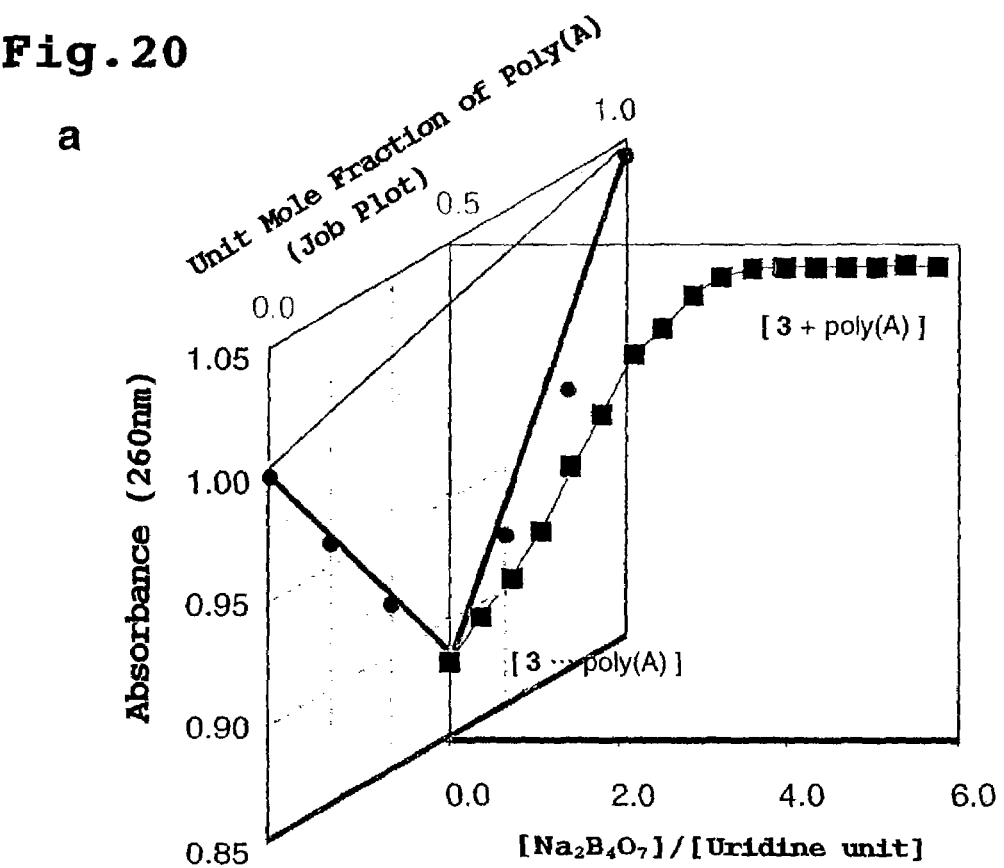
FIG. 20a is a representation of the results of continuous absorbance (260 nm) plotting, in Example 3 (1), following incorporation of polyadenylic acid into phosphate buffer (pH 7.2) containing PRNA1, followed by addition of borax while increasing the amount thereof (0 to 6 equivalents relative to PRNA).
FIG. 20b is a representation of the results of continuous absorbance (260 nm) plotting following incorporation of borax (6 equivalents) followed by addition of xylose.
Figure 20:
Figure 20:
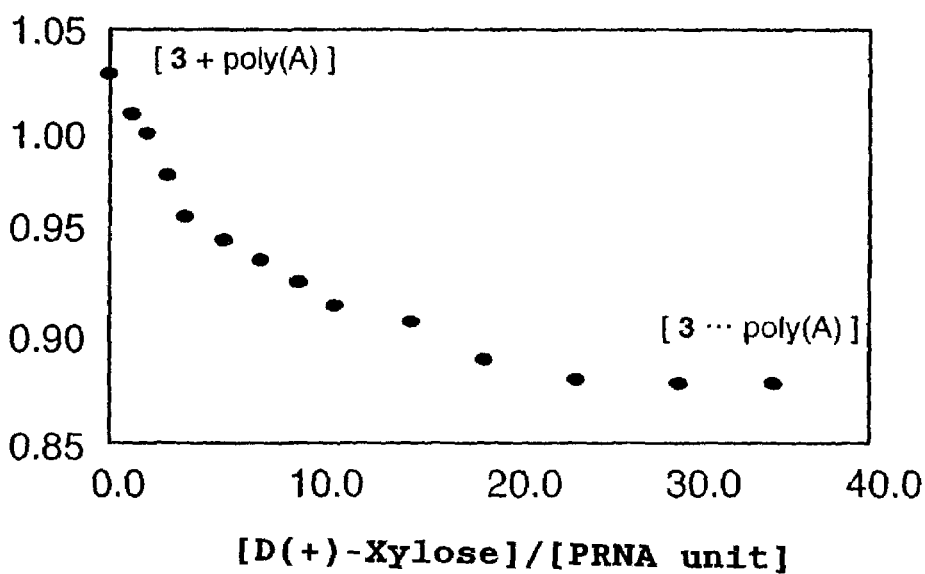
Figure 21:
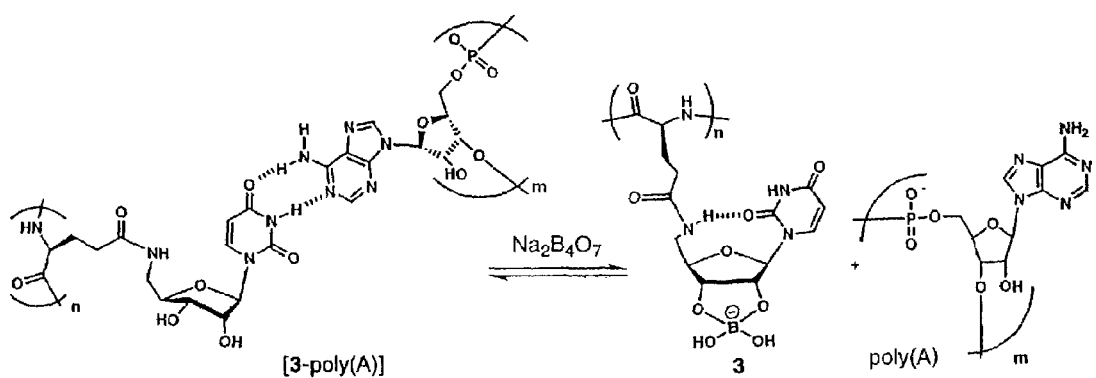
FIG. 21 is an illustration showing the change in orientation of the uracil base moiety of PRNA1 in the presence or absence of borax and the resulting complex formation with a complementary oligonucleotide, poly(A), as measured in Example 3 (1).

Multifactor Control of the Base Moiety Orientation of PRNAs Using "Borates" and a Sugar (1) Orientation Regulation of the Base Moiety of a PRNA1 at pH 7.2 Using a Borate When a nucleic acid binds to its complementary strand and forms a complex, a marked decrease in absorbance at about 260 nm is observed. The stoichiometry of the complex can be revealed by continuously plotting the absorbance. Therefore, poly(Nγ-(5'-deoxy-5'-uridyl)-L-glutamine) PRNA1 (Production Example 1) was examined for its complex forming ability using polyadenylic acid (poly(A)) as its complementary strand. As a result, when poly(A) was added to a borax-free phosphate buffer solution of the PRNA1, the absorbance at 260 nm significantly decreased (decrease in absorbance from 1 to 0.88) and, thus, it was concluded that the PRNA1 and poly(A) form a complex (1:1) (plots ● in FIG. 20(a)). Then, borax was added to this PRNA1- and poly(A)-containing phosphate buffer solution, whereupon the absorbance (260 nm) increased in a concentration-dependent manner until a certain concentration, as shown by the plots ■ in FIG. 20(a). Upon addition of borax in an amount about 3 times the amount of the PRNA1, the absorbance (260 nm) increased to be the original absorbance prior to addition of poly(A). This is because the addition of borax leads borate ester bond formation at the cis-2',3'-diol site of the sugar moiety and the base moiety orientation of the PRNA1 thus changes, resulting in complete dissociation of the base pairs involved in complex formation between the PRNA1 and poly(A) (cf. FIG. 21). Furthermore, this borate ester was in equilibrium with its anionic form even at pH 7.2. This thus suggests that the anionic property of the borate ester moiety of the PRNA1 and the polyanionic property of the phosphodiester chain of poly (A) promote the dissociation of the complex between the PRNA1 and poly(A).

The above results showed that the base moiety orientation of the PRNA1 can be changed from anti to syn by the borate ester formation of the sugar moiety as resulting from the addition of the borate. It was further found that even when the distance to a nucleoside is significantly different from and farther than the distances generally observed with DNAs and RNA, the PRNA1 can recognize a complementary nucleic acid and that the nucleic acid recognizing ability of the PRNA1 can be controlled by addition of a borate as an external factor.

(2) Effects of Sugars on the Orientation Regulation of the PRNA1 Base Moiety

Then, when, in the above empirical system, D(+)-xylose was added to a borax-containing phosphate buffer solution containing the PRNA1 and poly(A) (containing borax in an amount 6 times the amount of PRNA1), the absorbance at 260 nm significantly decreases depending on the level of addition thereof (decrease in absorbance from 1.03 to 0.88) and it was thus observed that the PRNA1 and poly(A) form a complex. The addition of xylose in an amount about 20 times that of the PRNA1 led to perfect 1:1 complex formation between the PRNA1 and poly(A) (cf. FIG. 20(b)). It was also observed that when D(+)-glucose is used as the sugar in lieu of the above D(+)-xylose, the complex is formed by the addition of D(+)-glucose.

The above results thus revealed that the base moiety orientation control by addition of borax is dependent on sugars. Namely, it is believed that the base moiety orientation of the PRNA can be reversibly controlled by using "borates" as an orientation regulating factor and a sugar as an orientation regulation controlling factor (multifactor control).

The above examples revealed that, in pyrimidine type PRNAs, the base moiety orientation thereof can be changed from the ordinary anti orientation to the syn orientation by synergistically utilizing the hydrogen bond between the base moiety 2-position carbonyl group and the 5'-amino hydrogen atom and the change in sugar moiety puckering through the borate ester formation by 2',3' hydroxyl groups at the sugar moiety, and that such change in orientation and the effect of the negative charge generated on the PRNA can lead to dissociation of the complex. Namely, it was revealed that when the base moiety orientation of the pyrimidine type PRNAs is freely controlled, they can recognize the target nucleic acids and such recognition can be controlled in an on-off manner.

(3) Complex Formation Control in a γ-PRNA Octamer ($NH_2$-UUUUUUUU-Lys-OH) by Means of Boric Acid and pH Adjustment (Absorbance-based Investigations)

Figure 22:
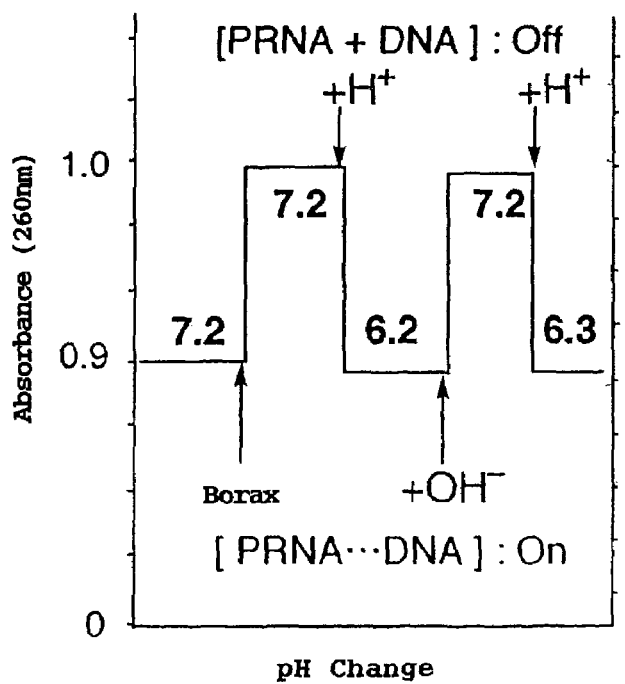
FIG. 22 is a representation of the changes in absorbance, which is shown the complex formation control by borax and by pH adjustment in the case of a γ-PRNA octamer (NH$_2$-UUUUUUUU-Lys-OH) (Example 3 (3)).

When a nucleic acid binds to its complementary strand and forms a complex, a marked decrease in absorbance at about 260 nm is observed. The stoichiometry of the complex can be revealed by continuously plotting the absorbance. Therefore, the reversible base moiety orientation control in a PRNA2 oligomer (octamer) by an orientation regulating factor and an orientation regulation controlling factor was confirmed in terms of hypochromic/hyperchromic effect on the absorbance (260 cm). Specifically, the changes in absorbance (260 nm) of the γ-PRNA octamer ($NH_2$-UUUUUUUU-Lys-OH) produced according to the method of Production Example 10 in response to boric acid addition and pH adjustment were measured. The results are shown in FIG. 22. As a result, the absorbance at 260 nm significantly increased upon addition of borax and complex dissociation was thus observed (hyperchromic effect, syn orientation, off-control). Then, the pH of this borax-containing system was adjusted from 7.2 to 6.2, whereupon the absorbance abruptly decreased, hence complex formation was observed (hypochromic effect, anti orientation, on-control). Thereafter, a hyperchromic effect was observed by syn orientation induction at high pH adjustment, and a hypochromic effect by anti orientation induction at low pH adjustment. By observing the hypochromic/hyperchromic effect on the absorbance in this manner, it could be confirmed that the complex formation/dissociation between the PRNA of the invention and a nucleic acid can be controlled by utilizing borax as an orientation regulating factor and pH as an orientation regulation controlling factor.

It is known that, in cancer cells, for instance, sialic acid is produced abundantly and the acidity increases accordingly. Therefore, by administering the PRNA (antisense molecule) of the invention in the state of a complex with a gene useful in cancer therapy, it becomes possible for the complex that has arrived at the target cancer cells to be specifically dissociated by the cancer cell-specific low pH and for the gene useful in cancer therapy to act on the cancer cells. Thus, the antisense molecule of the invention makes it possible to carry out selective therapy, without influencing normal tissues or cells, by selecting and using an orientation controlling factor according to the biological environment in question.

Example 4

Base Moiety Orientation in PRNAs Having a Pyrimidine-Purine Mixed Sequence

Three dimmers, Boc-isoGln(5'U)-isoGln(5'U)-OH (Production Example 2 (5), U-U), Boc-isoGln(5'U)-isoGln(5'I)-OH (Production Example 7 (2), U-I) and Boc-isoGln(5'I)-isoGln(5'U)-OH (Production Example 8 (2), I-U), were synthesized by condensing an N terminally deprotected monomer and a C terminally deprotected monomer with each other using the Bop reagent and HOBt. Among them, the PRNA of Production Example 7 (2) having a pyrimidine-purine mixed sequence was examined for its base moiety orientation control.

(1) $^1$H-NMR Difference NOE Spectrum

Figure 23:
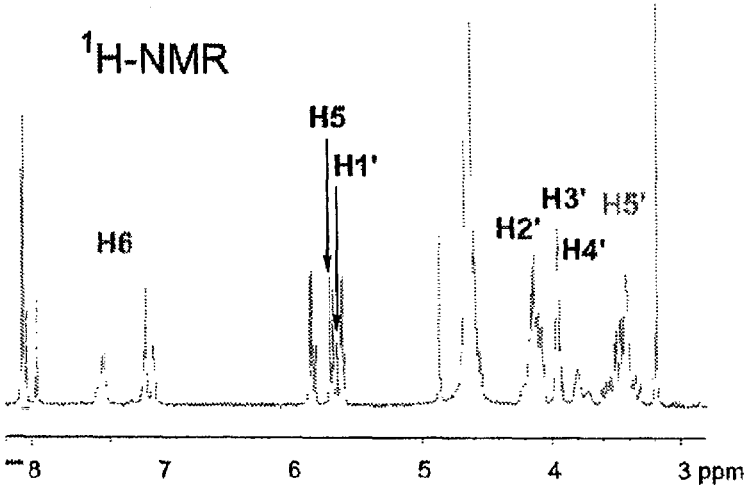
FIG. 23 is a representation of ¹H-NMR and NOE spectra of Boc-AEG(5'cU-carboante)-OH in phosphate buffer and borate buffer as measured in Example 4 (1).
Figure 23:
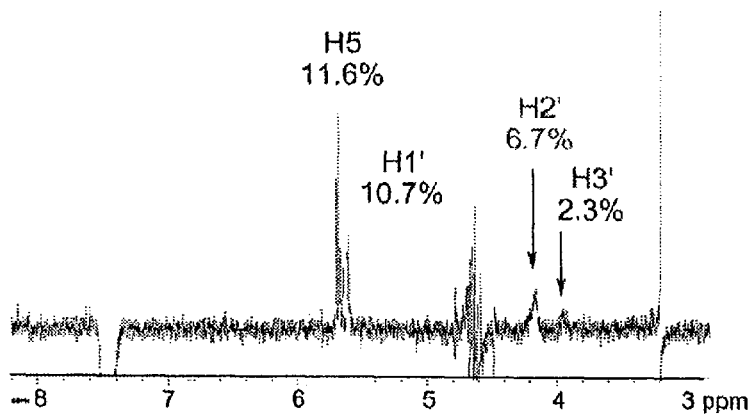
Figure 23:
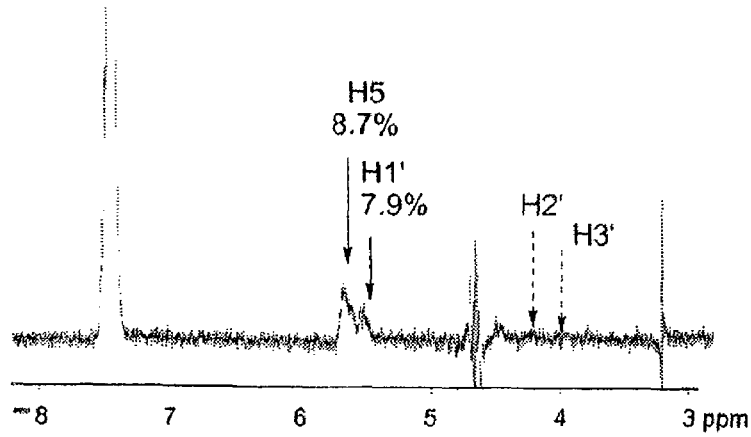
Figure 24:
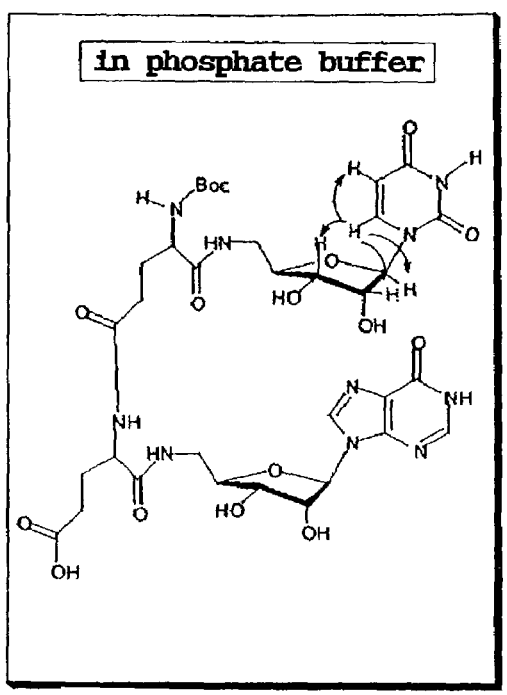
FIG. 24 is an illustration showing estimated orientation behaviors of Boc-isoGln(5'U)-isoGln(5'I)-OH in phosphate buffer and borate buffer.
Figure 24:
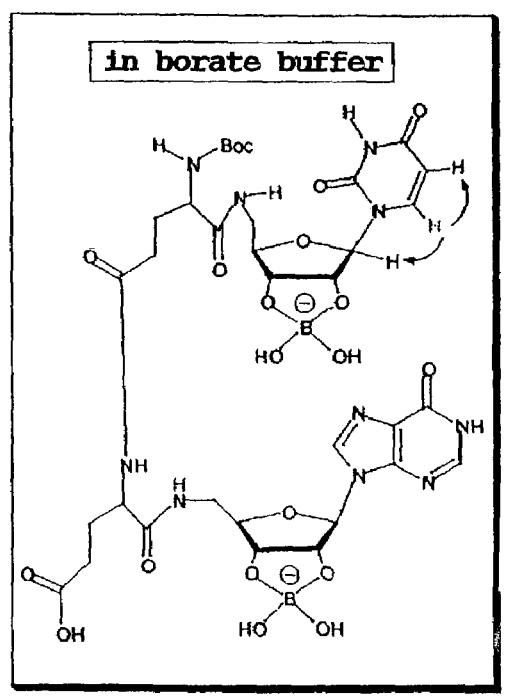

First, for investigating the pyrimidine base moiety orientation control, a $^1$H-NMR difference NOE spectrum obtained upon uracil 6-position irradiation was used, like in Example 1 (1-2) (5'-$NH_2$-Urd), and the pyrimidine base moiety orientation control by boric acid was investigated. Boc-IsoGln(5'U)-isoGln(5'I)-OH (Production Example 7 (2), U-I) was used as the PRNA having a pyrimidine-purine mixed sequence. The results are shown in FIG. 23. In phosphate buffer, peaks were observed for the base moiety 5-position and the sugar moiety 1'-, 2'- and and 3'-positions and it was revealed that the pyrimidine base moiety had an anti orientation. On the other hand, in borate buffer, peaks were observed only for the 5- and 1'-positions and it was thus revealed that the pyrimidine base moiety was in syn orientation. From this finding, it was found that even when such a dimer contains a purine unit, the pyrimidine base moiety orientation thereof can be controlled by synergistically utilizing the change in sugar moiety puckering by borate ester formation, and the hydrogen bond between the 5'-amide hydrogen atom and the base moiety 2-position carbonyl group, like in the case of monomer (FIG. 24).

Figure 25:
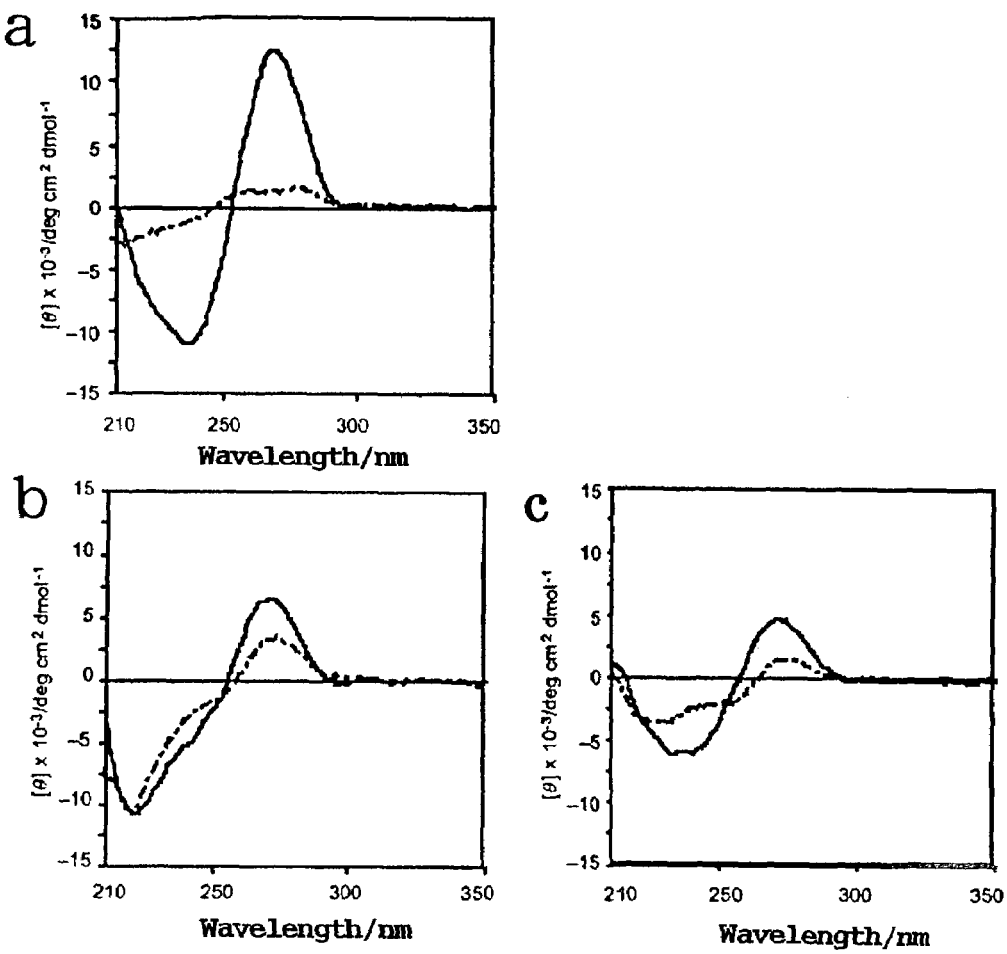
FIG. 25 is a representation of the results of CD spectrum measurements, in Example 4 (2), of PRNAs (U-U (FIG. 25a), U-I (FIG. 25b) and I-U (FIG. 25c)) in phosphate buffer (pH 7.2) and borate buffer (pH 7.2).

(2) Circular Dichroism Spectrum (i) CD spectrum measurements were carried out for the above three PRNAs (U-U, U-I and I-U) in phosphate buffer (pH 7.2) and in borate buffer (pH 7.2) in the same manner as in Example 1 (1-1). The results are shown in FIG. 25 (a: U-U, b: U-I, c: I-U). In FIG. 25, the solid lines indicate the CD spectra in phosphate buffer, and the broken lines the CD spectra in borate buffer. The molar ellipticity ([θ]ext) at about 270 nm for the CD spectrum for each PRNA in each buffer is shown in Table 5.

TABLE 5

| PRNA dimer | Molar ellipticity ([θ]ext) | | |
|---|---|---|---|
| | Phosphate buffer | Borate buffer | Δ[θ]ext |
| U-U | 12300 | 1250 | 11050 |
| U-I | 6600 | 3300 | 3300 |
| I-U | 4800 | 1400 | 3400 |

As can be seen from the results, the [θ]ext value per unit of U-I was 6600 in phosphate buffer but it decreased to 330 in borate buffer, indicating a change to the syn base moiety orientation in the presence of boric acid. This result is in agreement with the result of the $^1$H-NMR difference NOE spectrum mentioned above under (1). Also for I-U having a sequence with the N terminal side and C terminal side units reversed, almost the same extent of buffer-dependent decrease was observed, indicating that the pyrimidine unit base moiety orientation can be controlled using boric acid as an external factor, irrespective of the site of bonding of the pyrimidine unit. Furthermore, it was revealed that, in U-U having a continued pyrimidine sequence, the anti orientation much predominates in phosphate buffer and the syn orientation can be induced efficiently in borate buffer.

Figure 26:
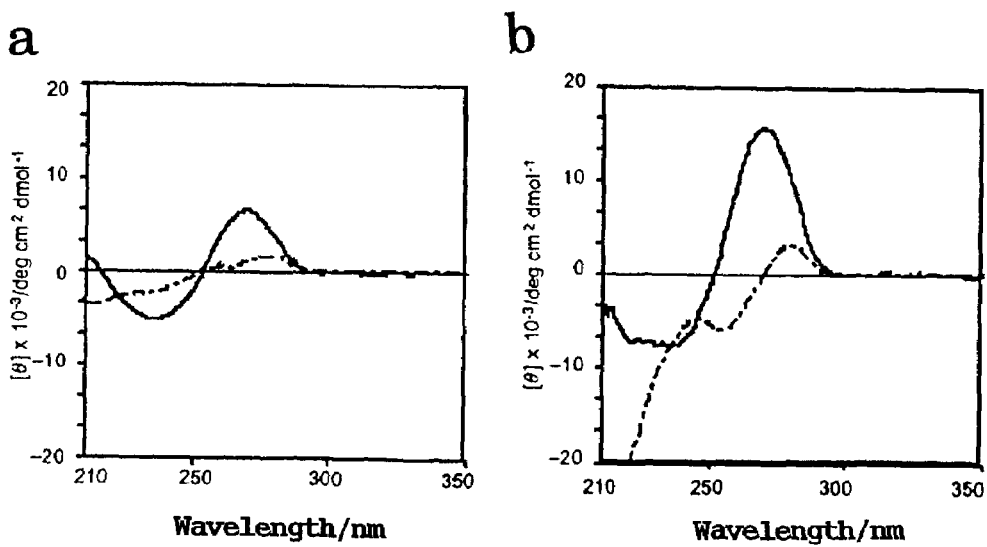
FIG. 26 is a representation of the results of CD spectrum measurements, in Example 4 (2), of trimeric PRNAs (U-U-U (FIG. 26a), and U-I-U (FIG. 26b)) in phosphate buffer (pH 7.2) and borate buffer (pH 7.2).

(ii) For studying the sequence effect in more detail, Boc-isoGln(5'U)-isoGln(5'U)-isoGln(5'U)-OH (Production Example 5 (2), U-U-U) having three consecutive uridine units, and Boc-isoGln(5'U)-isoGln(5'I)-isoGln(5'U)-OH (Production Example 9, U-I-U) having an inosine unit between two uridine units were synthesized by the fragment condensation method, their CD spectra were measured, and their base moiety orientation behaviors were observed (FIG. 26) (a; U-U-U, b: U-I-U). In FIG. 26, the solid lines indicate the CD spectra in phosphate buffer, and the broken lines the CD spectra in borate buffer. These results revealed that the [θ]ext decreases when the borate buffer is substituted for the phosphate buffer, namely that the orientation in borate buffer is syn. It was thus revealed that the base moiety orientation can be controlled even in PRNA trimers having a purine unit by borate ester formation.

Example 5

Figure 27:
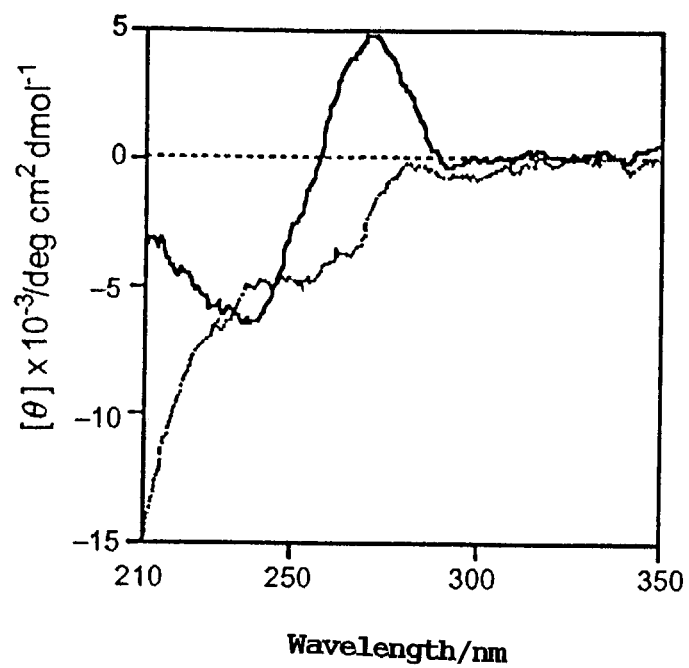
FIG. 27 is a representation of the results of CD spectrum measurements, in Example 5, of a PRNA octamer, $NH_2$-UIIUUUU-Lys-OH, in phosphate buffer and borate buffer.

(1) Base Moiety Orientation in PRNAs (Octamers) Having a Pyrimidine-purine Mixed Sequence For the PRNA octamers NH$_2$-UIIUUUUU-Lys-OH and NH$_2$-IIIIIIII-Lys-OH synthesized by the solid phase method in Example 10, the base moiety orientation control behaviors in the presence or absence of "borates" were examined by measuring CD spectra in phosphate buffer and in borate buffer. The results obtained with NH$_2$-UIIUUUUU-Lys-OH are shown in FIG. 27, and the results obtained with NH$_2$-IIIIIIII-Lys-OH in FIG. 28. In each figure, the solid line indicates the CD spectrum in phosphate buffer, and the broken line the CD spectrum in borate buffer.

Figure 28:
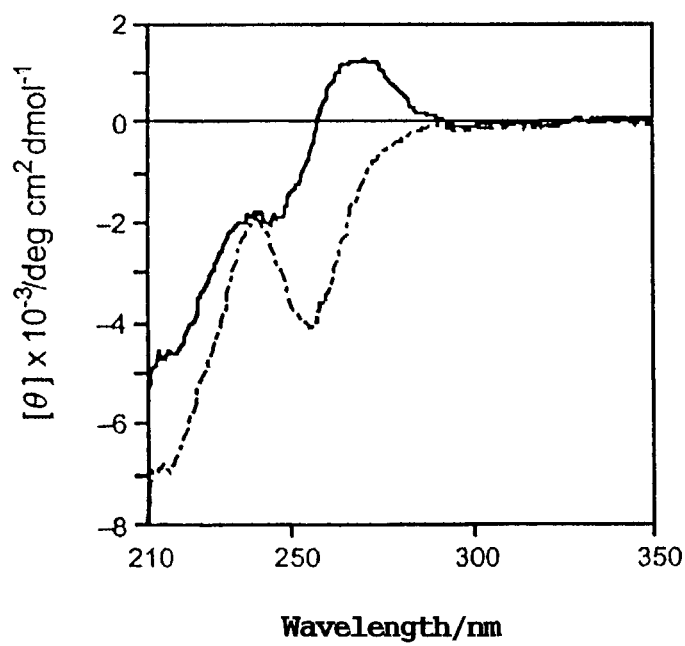
FIG. 28 is a representation of the results of CD spectrum measurements, in Example 5, of a PRNA octamer, $NH_2$-IIIIIIII-Lys-OH, in phosphate buffer and borate buffer.

As shown in FIG. 27, the CD peak of the NH$_2$-UII-UUUUU-Lys-OH in borate buffer showed a marked decrease, indicating that its orientation control to the syn orientation is possible with boric acid. For NH$_2$-IIIIIIII-Lys-OH, a positive CD peak was observed at about 270 nm in phosphate buffer, as shown in FIG. 28. This was interpreted as follows: the oligomerization of inosine caused steric repulsion against the main chain, whereby the base moiety anti orientation was induced. Furthermore, since excitone coupling was observed at 258 nm corresponding to λmax, base stacking was indicated and it was revealed that it has a higher-order structure.

(2) Control of Nucleic Acid Recognition of PRNAs (Octamers) Having a Pyrimidine-purine Mixed Sequence Using the PRNA octamers NH$_2$-UIIUUUUU-Lys-OH and NH$_2$-IIIIIIII-Lys-OH, their ability to form a complex with a nucleic acid (oligonucleotide) was examined and whether said complex formation was controlled by "borates" or not was checked.

Specifically, the PRNA (octamer NH$_2$-UIIUUUUU-Lys-OH) was mixed with each of oligonucleotide octamers specified in Table 6, the melting temperature (Tm) was determined by measuring the resulting change in absorbance on UV spectra, and the ability of the PRNA (octamer) to hybridize with the nucleic acid (complex forming ability) was evaluated based on the resultant melting temperature. Furthermore, the effects of a borate on the PRNA (octamer)-DNA hybrid formation and the stability thereof were investigated using the PRNA (octamer) and 5'-d(AAAAACCA)-3', a complementary compound as its binding target oligonucleotide, and measuring the melting temperatures with and without addition of borax (20 mM) to the phosphate buffer and comparing them. The results are also shown in Table 6. A control experiment was carried out in the same manner using 5'-d(AC-CAAAAA)-3' as the binding target oligonucleotide in lieu of 5'-d(AAAAACCA)-3'.

TABLE 6

| | | Tm/° C. Additive | |
|---|---|---|---|
| PRNA, or Oligonucleotide | Binding target compound | Non | 20 mM Borax |
| NH$_2$UIIUUUUU-Lys-OH | 5'd(AAAAACCA)3' | 7.8 | <0 |
| | 5'd(ACCAAAAA)3' | 6.2 | <0 |
| 5'd(TIITTTTT)3' | 5'd(AAAAACCA)3' | 4.7 | 6.0 |

PRNA = 1.0 × 10$^{-4}$ M,
Oligonucleotide = 1.0 × 10$^{-4}$ M in $^1$/$_{30}$ M Phosphate buffer From the above results, it was found that the PRNA (octamer) interacts specifically with its complementary oligonucleotide 5'-d(AAAAACCA)-3'. In borax-free buffer, the melting temperature of the complex formed between the PRNA (octamer) and 5'-d(AAAAACCA)-3'was 7.8° C. and this was significantly higher than the melting temperature (4.7° C.) of the complex between the DNA octamer 5'-d(TIITTTTT)-3' and its complementary DNA octamer (5'-d(AAAAACCA)-3'). This indicates that the PRNA (octamer)-DNA complex is more stable than the DNA-DNA complex in the borax-free system. This is probably because the PRNA has no charge either on the main chain or on the side chains and therefore can efficiently form a complex with the target DNA, whereas both main chains of the DNA-DNA are unstabilized by an electrostatic anion-to-anion repulsive force. Furthermore, since the Tm lowered by 1.6° C. to 6.2° C. when 5'-d(ACCAAAAA)-3' was used as the binding target oligonucleotide, in lieu of 5'-d(AAAAACCA)-3', it was revealed that an antiparallel orientation is predominant in the PRNA-DNA complex.

Figure 29:
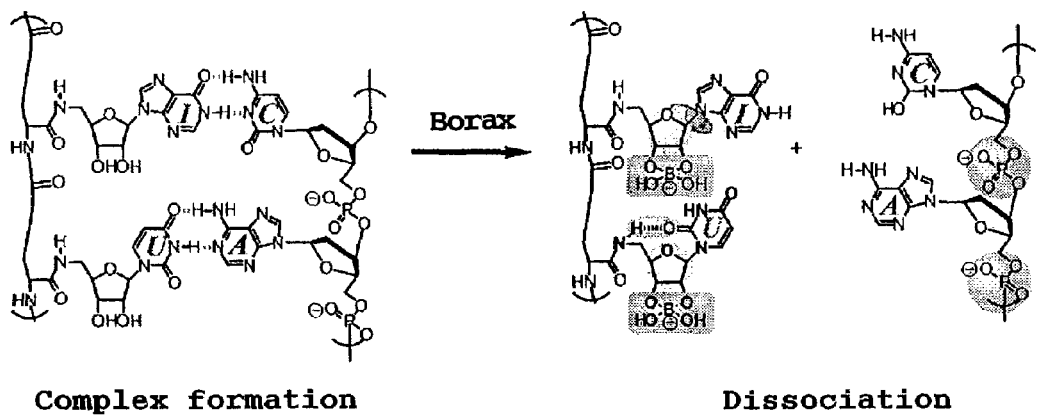
FIG. 29 is an illustration showing the anticipated behavior of a pyrimidine-purine mixed PRNA recognizing a DNA, as resulting from controlling of "borates".

In borax-added buffer, on the other hand, the DNA-DNA complex was stabilized by the effect of the salt strength, whereas the PRNA (octamer)-DNA complex showed a melting temperature lower than 0° C., suggesting the dissociation of the complex. The reasons for this are probably that the orientation of the pyrimidine type PRNA was changed to the syn orientation, which is disadvantageous for complex formation, by the change in orientation due to the synergistic effect of the change in sugar moiety puckering as resulting from borate ester formation and the hydrogen bond formation between the 5'-amide hydrogen and base moiety 2-position carbonyl group, and that an electrostatic repulsion toward the DNA occurred due to the anion formation resulting from borate ester formation (FIG. 29).

(ii) Since, in (1), the possibility of structural control by "borates" was suggested also for the PRNA (NH$_2$-IIIIIIII-Lys-OH) having a homopurine sequence, the complementary oligonucleotide d(C)$_8$ was used, as shown in the table, and the complementary nucleic acid recognition was examined in the same manner as mentioned above. The results are also shown in Table 7.

TABLE 7

| PRNA, or Oligonucleotide | Binding target compound | Tm/° C. Additive | |
|---|---|---|---|
| | | 20 mM Non | Borax |
| NH$_2$-IIIIIIII-Lys-OH | d(C)$_8$ | 4.8 | <-5 |
| poly(I) | d(C)$_8$ | 4.5 | 5.7 |

Figure 30:
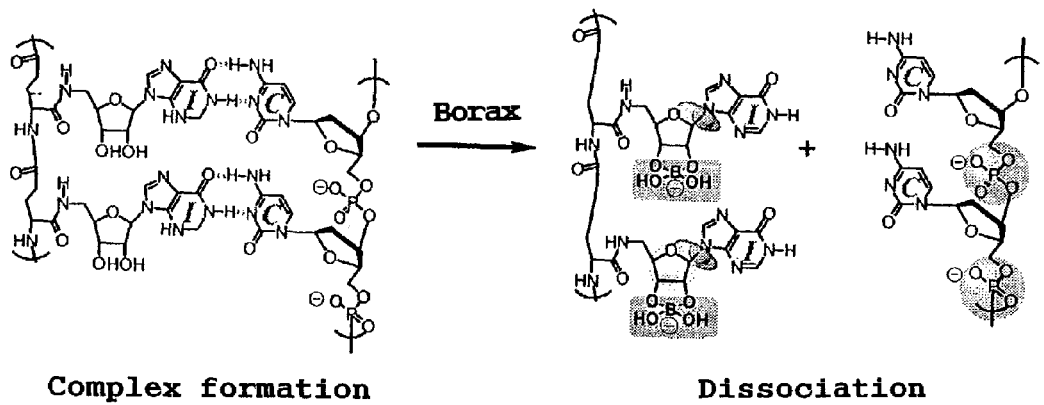
FIG. 30 is an illustration showing the anticipated behavior of a purine-based PRNA recognizing a DNA, as resulting from controlling of "borates".

PRNA = 1.0 × 10$^{-4}$ M
Oligonucleotide = 1.0 × 10$^{-4}$ M in 1/30 M Phosphate buffer As can be seen from Table 7, the stability of the PRNA-DNA was almost comparable to that of a natural nucleic acid (DNA-DNA complex) under these conditions. Further addition of borax to this system stabilized the DNA-DNA complex owing to the salt effect, whereas the PRNA-DNA complex showed no Tm at or above −5° C., suggesting the dissociation of the complex. Thus, the use of "borates" as an external factor also modified the structure of the PRNA having a homopurine sequence and caused an electrostatic repulsion between the negative charges on the main chain. It was thus revealed that the target DNA recognition can be controlled in an on-off manner (with reversible) by utilizing the above facts (FIG. 30).

In the above-mentioned, Examples 4 and 5, it was revealed that, for the purine base type PRNA as well, it is possible to cause complex dissociation by the disappearance of a higher structure as resulting from borate ester formation and by anion formation resulting from borate ester formation.

The above examples revealed that the addition of an external factor such as "borates" to a phosphate buffer solution of the antisense molecule of the invention can change the base moiety orientation of the nucleoside from anti predominance to syn predominance. This change in orientation is attained by the synergy of two factors, namely the borate ester bond formation at the 2',3' positions of sugar moiety in the antisense molecule and the hydrogen bond formation between the base moiety 2-position carbonyl group and 5'-amide hydrogen. The stability of the borate ester bonding is dependent on pH, so that the regulation of the base moiety orientation is also dependent on pH. Thus, it was revealed that, at high pH conditions, the changing of the base moiety orientation of the antisense molecule to the syn orientation is accomplished with good efficiency whereas, at low pH conditions, no change occurs in the base moiety orientation. Furthermore, it was revealed that the base moiety orientation of the antisense molecule can be reversibly controlled using "borates" and pH, or "borates" and a sugar, as external factors.

The 2',3' hydroxyl groups and the 5'-amino hydrogen capable of hydrogen bonding are required for the orientation control. Therefore, experiments were carried out in the same manner using such pyrimidine type PRNAs, such as the AEG (5'U) monomer and isoGln(5'U) monomer, resulting from introduction of 5'-NH$_2$-Urd in the peptide chain without impairing the above-mentioned functional groups, and it was revealed that the base moiety orientation thereof can be reversibly controlled by means of "borates" and pH, or "borates" and a sugar. It was further revealed that, for not only the pyrimidine type PRNAs but also purine base type PRNAs, the base moiety orientation thereof can be reversibly controlled by "borates" as an external factor. Thus, it was found that an arbitrary PRNA of the invention, whether a pyrimidine PRNA or a purine type one, can recognize its complementary sequence and further that such recognition can be controlled by utilizing an external factor(s) such as "borates", pH and/or a sugar in accordance with the invention.

Thus, the reversible target nucleic acid recognizing ability of the PRNAs of the invention can be applied to any of the nucleic acid models so far proposed, so that the PRNAs of the invention are useful in creating novel antisense molecules.

As drawbacks of the PNAs reported by Nielsen et al. (Science 1991, 254, 1497), there may be mentioned, among others, excessively high affinity, nonspecific protein adsorption, and scarce solubility in water. Of course, the PNAs are incapable of reversible control of nucleic acid sequence recognition. On the contrary, the PRNAs to be used in accordance with the present invention, unlike the PNAs, have hydroxyl groups and therefore are superior in solubility in water, whereby it is expected that improvements in affinity be produced and the nonspecific protein adsorption be reduced. In view of the possibility of reversible control (on-off control) in recognizing nucleic acid sequence, too, they can be said to be nucleic acid models of a higher level than the PNAs.

In utilizing the PRNA as orientation-controllable antisense molecules, one of the methods of minimizing the amount of "borates" which is an orientation regulating factor, and making the best of the orientation controllability of the PRNA will be the application thereof to a drug delivery system (DDS). Thus, the method comprises administering, as a drug, a PRNA in a recognizing ability off state by coupling with a boric acid so that only those molecules that have arrived at the infected site showing a low pH can act as antisense molecules (PRNA) following their recognizing ability being switched on. It is known that sialic acid is produced abundantly in cancer and like cells and the acidity is high in such cells. Therefore, it is expected that such DDS will produce its effect effectively. Further, with a model resulting from coupling of a PRNA to boric acid via a linker to form an intramolecular borate ester bond, it is expected that the nucleic acid recognizing ability can be controlled in an on-off manner (with reversible) by pH control alone. In this way, the PRNAs are highly functional nucleic acid models and can be expected to play an important role in creating next generation antisense molecules.

Example 6

Base Moiety Orientation Control of a Dimeric Chimera Nucleic Acid (PRNA-DNA)

A chimeric nucleic acid (PRNA(Urd)-DNA(Thr)) resulting from coupling of a PRNA (Urd) to the N terminus of a DNA (thymidine) via an amide bond was synthesized (Production Example 11), and the base moiety orientation control of said chimeric nucleic acid was examined using "borates" as an external factor.

(1) Circular Dichroism Spectrum

Figure 31:
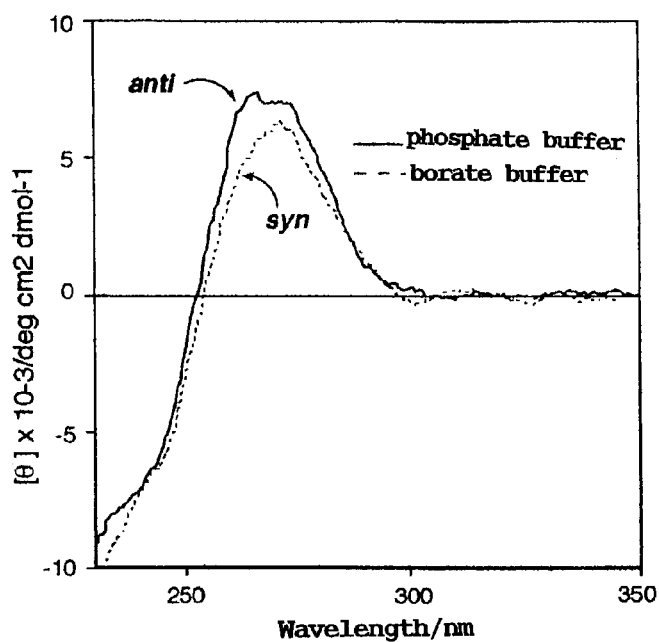
FIG. 31 is a representation of the results of CD spectrum measurements, in Example 6(1), of a chimeric nucleic acid (PRNA(Urd)-DNA(Thr)) in phosphate buffer (pH 7.2) and borate buffer (pH 7.2).

With the chimeric nucleic acid (PRNA(Urd)-DNA(Thr)), CD spectrum measurements were carried out in phosphate buffer (pH 7.2) and in borate buffer (pH 7.2) in the same manner as in Example 1 (1-1). The results are shown in FIG. 31. In FIG. 31, the solid line indicates the CD spectrum in phosphate buffer, and the broken line the CD spectrum in borate buffer. The molar ellipticity ([θ]ext) at about 270 nm in the CD spectrum of the chimeric nucleic acid in each buffer is shown in Table 8.

TABLE 8

| Chimeric nucleic acid etc. | Molar ellipticity ([θ]ext) | | Δ[θ]ext |
|---|---|---|---|
| | Phosphate buffer | Borate buffer | |
| PRNA(U)-DNA(T) [B] | 7500 | 6400 | 1100 |
| 5'-NH$_2$-Urd | 5100 | 1600 | 3500 |
| 5'-NH$_2$-Thd [A] | 600 | 950 | −350 |
| [B] − [A] | 8100 | 6000 | 2100 |

As can be seen from the results, the [θ]ext value per unit of the chimeric nucleic acid was 7500 in phosphate buffer but it decreased to 6400 in borate buffer, revealing that the syn orientation is induced in the presence of boric acid even in the base moiety of the chimeric molecule. The [θ]ext values for 5'-NH$_2$-Urd and 5'-NH$_2$-Thd, which are constituents of the chimeric nucleic acid, are also shown in the above table. As the results indicate, the decrement in [θ]ext of the chimeric nucleic acid was smaller than that of 5'-NH$_2$-Urd. On the other hand, the [θ]ext of 5'-NH$_2$-Thd, which is also a constituent of the chimeric nucleic acid, increases upon addition of boric acid. Based on this, the difference between the spectrum of the chimeric nucleic acid and that of 5'-NH$_2$-Thd was calculated, in order to investigate the change in structure of the PRNA moiety of the chimeric nucleic acid. As a result, the decrease of the [θ]ext value in the chimeric nucleic acid was 2100, indicating that the syn orientation is induced in the base moiety of the PRNA(Urd) moiety in the chimeric nucleic acid (PRNA(Urd)-DNA(Thd)).

(2) $^1$H-NMR Difference NOE Spectrum

Figure 32:
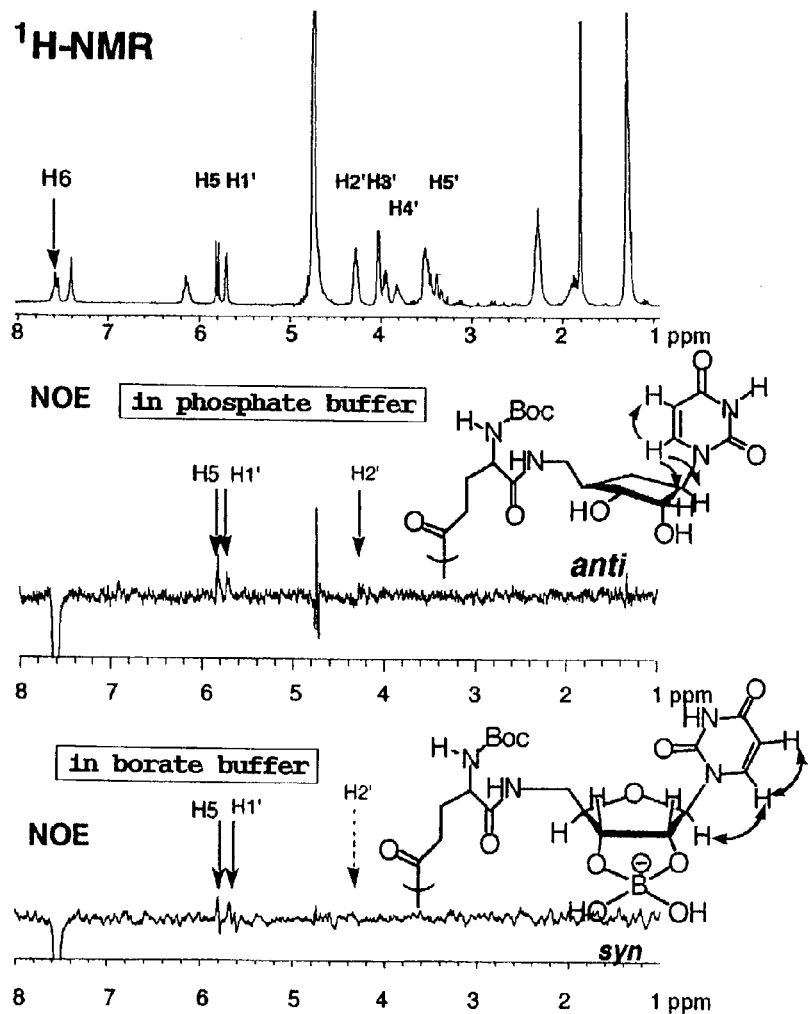
FIG. 32 is a representation of ¹H-NMR and NOE spectra of a chimeric nucleic acid (PRNA(Urd)-DNA(Thr)) in phosphate buffer and borate buffer as measured in Example 6 (2).

The base moiety orientation control by "borates" in the chimeric nucleic acid (PRNA(Urd)-DNA(Thr)) was investigated in the same manner as in Example 1 (1-2) using $^1$H-NMR difference NOE spectra obtained by proton irradiation at position 6 of Uracil. The results are shown in FIG. 32. In phosphate buffer, NOE peaks were observed for the base moiety 5-position and the sugar moiety 1'-position as well as the 2'-position. It was thus revealed that the anti orientation is predominant in the base moiety in phosphate buffer. On the other hand, in borate buffer, NOE peaks were observed only for the base moiety 5-position and sugar moiety 1'-position. It was revealed that the syn orientation is induced in the base moiety in the presence of boric acid.

In view of the above, it was revealed that, in the dimeric chimera molecule (PRNA-DNA), the orientation of the uridine base moiety of the PRNA moiety, which is a pyrimidine nucleoside, can be controlled from the ordinary anti orientation to the syn orientation by utilizing the synergy between the hydrogen bonding of the base moiety 2-position carbonyl group to the 5'-amide hydrogen and the change in sugar moiety puckering due to borate ester formation by the sugar moiety 2',3' hydroxyl groups.

Example 7

Base Moiety Orientation Control of a Dodecameric Chimera Nucleic Acid (PRNA-DNA)

A dodecamer of the above chimeric nucleic acid (PRNA(Urd)-DNA(Thd)) having an amide bond as the bond between PRNA and DNA was synthesized (Production Example 12), and the base moiety orientation control of said chimeric nucleic acid was examined using boric acid as an external factor.

(1) Circular Dichroism Spectrum

Figure 33:
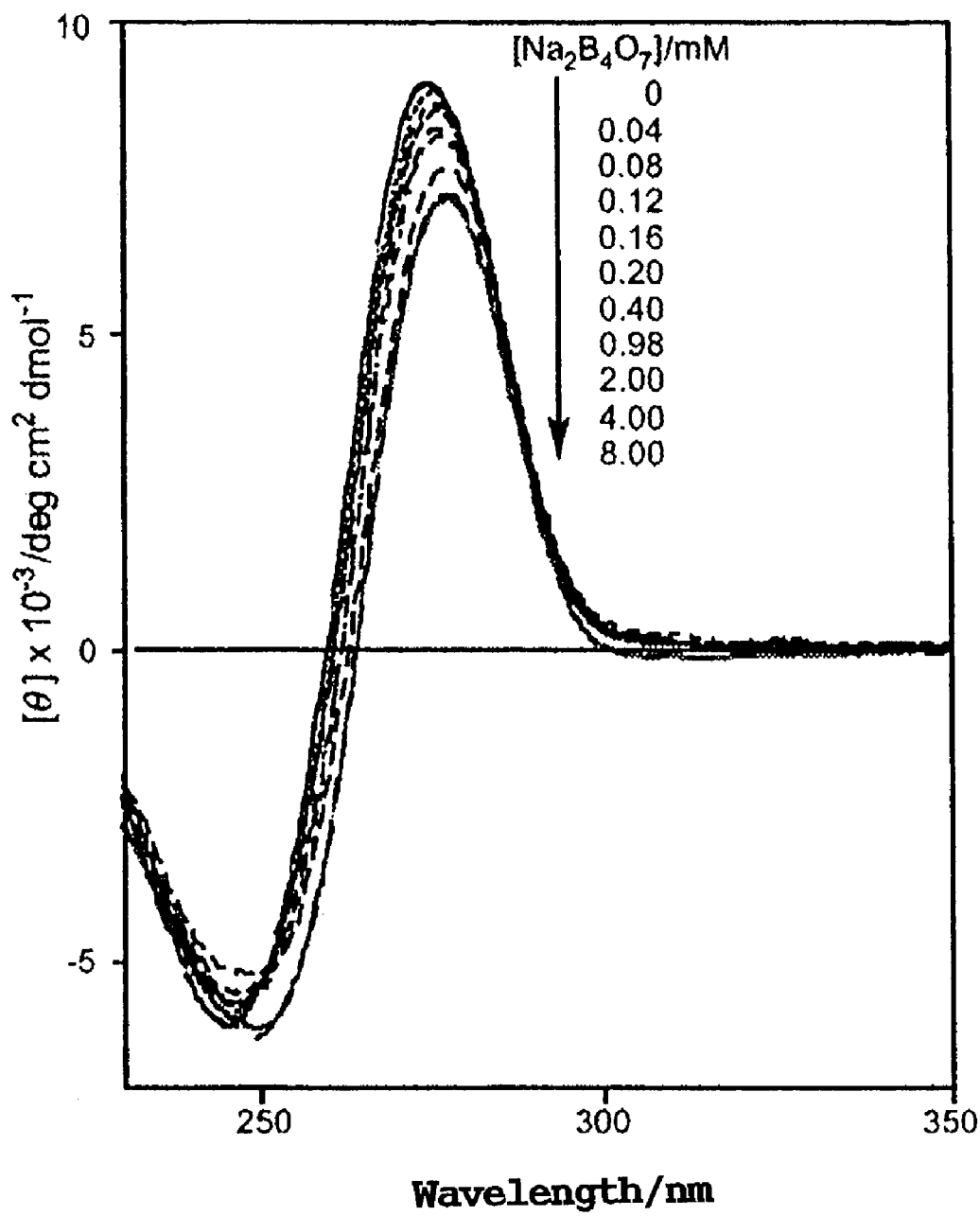
FIG. 33 is a representation of the results of CD spectrum measurements, in Example 7 (1), of a dodecameric chimeric nucleic acid (PRNA(U)$_8$-DNA(T)$_4$) in phosphate buffer (pH 7.2) and borate buffer (pH 7.2).
Figure 34:
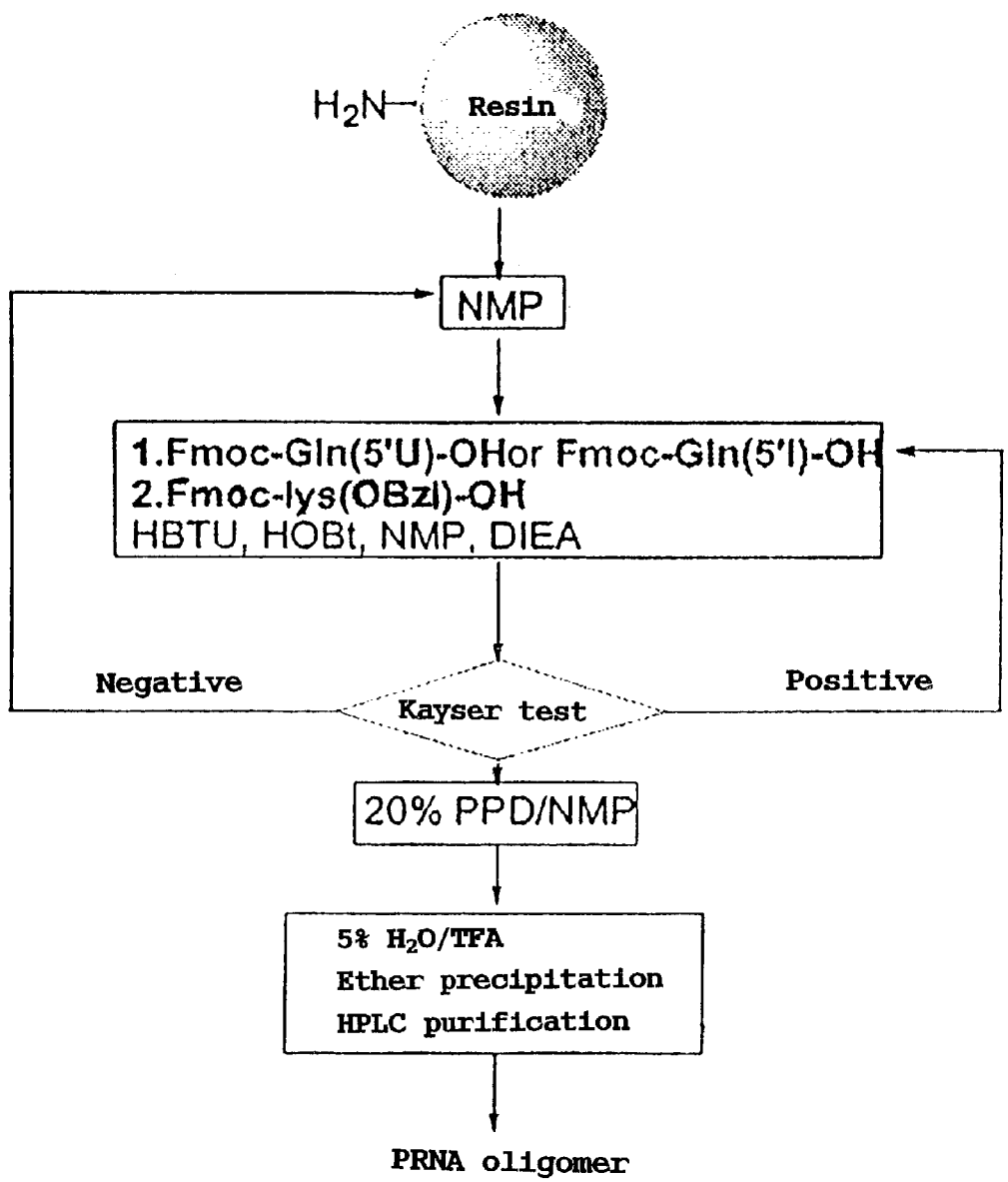
FIG. 34 is a schematic representation of the process for the solid phase synthesis of nucleoside derivatives according to the invention (PRNA oligomers or polymers).

With the dodecameric chimera nucleic acid (PRNA(U)$_8$-DNA(T)$_4$), CD spectrum measurements were carried out in phosphate buffer (pH 7.2) and in borate buffer (pH 7.2) in the same manner as in Example 1 (1-1). The results are shown in FIG. 33. The results of the molar ellipticity ([θ]ext) at about 270 nm suggested that the anti orientation is predominant in the base moiety of said chimeric nucleic acid in phosphate buffer. On the other hand, the [θ]ext decreased upon addition of borax, revealing that the syn orientation is induced in the base moiety by the presence of "borates".

(2) Control of Nucleic Acid Recognition of the Dodecameric Chimera Nucleic Acid

Using the above dodecameric chimera nucleic acid and a DNA having a complementary base sequence, the melting temperature Tm was measured in phosphate buffer allowing predominance of the anti orientation in the PRNA moiety. The results are shown in Table 9.

TABLE 9

| PRNA, or Oligonuoleotide | Binding target compound | Tm/° C. Additive | |
|---|---|---|---|
| | | Non | 20 mM Borax |
| NH$_2$-UUUUUUUUTTTT-3' | d(A)$_{12}$ | 42.5 | <0 |
| 5'-TTTTTTTTTTTT-3' | d(A)$_{12}$ | 23.2 | 27.5 |

PRNA = 1.0 × 10$^{-4}$ M,
Oligonucleotide = 1.0 × 10$^{-4}$ M in $^1$/$_{30}$ M Phosphate buffer (pH 7.2)

As shown in Table 9, the melting temperature Tm of the d(A)$_{12}$-d(A)$_{12}$ complex was 23.2° C. and the melting temperature Tm of the PRNA(U)$_8$DNA(T)$_4$-d(T)$_{12}$ complex was 42.5° C., suggesting that the latter complex formed is more stable by 19.3° C. than the d(A)$_{12}$-d(A)$_{12}$ complex. The reason is probably that the DNA-DNA complex is unstable because of the electrostatic repulsive force due to the negative charges on the DNA main chains whereas, as for the chimeric nucleic acid (PRNA)-DNA complex, the PRNA has no electric charge on the main chain, hence can efficiently form the complex with the DNA.

On the other hand, when borax was added to this system, the d(A)$_{12}$-d(A)$_{12}$ complex was stabilized, with a rise in Tm by 4.3° C., by the salt effect whereas, in the (U)$_8$DNA(T)$_4$-d(A)$_{12}$ mixture system, no melting temperature was observed at 0° C. or above, indicating that the complex had been dissociated. The presumable reasons are that the PRNA acquired the syn orientation, which is unfavorable for complex formation, by the synergy of the change in puckering of the uridine sugar moiety in the PRNA and the hydrogen bond between the 5'-amide hydrogen and the base moiety 2-position carbonyl group and that an electrostatic repulsion was caused by the occurrence of negative charges in the PRNA moiety as resulting from borate ester formation.

The above results revealed that the base moiety orientation is possible even in the chimeric nucleic acid dodecamer, like in the chimeric nucleic acid dimer, and that the dodecamer can form a stable complex with nucleic acid sequence in a base moiety-specific manner and the complex can be efficiently dissociated by the synergistic effects of the syn orientation and the anions formed on the PRNA.

PRODUCTION EXAMPLES

Reference Production Example 1

Production of 5'-amino-5'-deoxyuridine
(5'-$NH_2$-Urd)

(1) Production of 5'-azido-5'-deoxyuridine

Uridine (5.5 g, 22.5 mmol), triphenylphosphine (11.8 g, 45.0 mmol) and lithium azide (5.51 g, 112.6 mmol) were dissolved in dried DMF (120 ml). Then, carbon tetrabromide (14.92 g, 45.0 mmol) was added with vigorous stirring and after 2 hours of stirring, about 5 ml of methanol was added to terminate the reaction. The DMF was distilled off under reduced pressure, and the residue was purified by column chromatography (silica gel; chloroform-methanol (30:1 v/v) to give 5'-azido-5'-deoxyuridine (5.40 g, 21.2 mmol, yield 94%). A white solid.

vmax (Se board)/$cm^{-1}$: 3370, 2080, 1690, 1270, 1100, 1060 δH (270 MHz; DMS-$d_6$): 3.59(2H,m,5'-H), 3.92(2H,m, 3'-H,4'-H,) 4.13(1H,q,$J_{2',1'}$=$J_{2',3}$=5.0,2'-H), 5.30(1H,d,$J_{OH,3'}$, 5.0,3'-OH), 5.50(1H,d,$J_{OH,2'}$,5.6,2'-OH), 5.67(1H,d,$J_{5,6}$7.9, 5-H), 5.77(1H,d,$J_{1',2'}$,5.6,1'-H), 7.69(1H,d,$J_{6,5}$7.9,6-H), 11.38(1H,s,3-NH)

(2) Production of 5'-amino-5'-deoxyuridine

To a solution of the 5'-azido-5'-deoxyuridine (2.51 g, 9.33 mmol) obtained as described above in methanol (100 ml) was added palladium-on-carbon Pd/C (10%, about 0.25 g). While bubbling hydrogen (1 atm), the mixture was stirred at room temperature for 2 hours. Then, the reaction mixture obtained was filtered to remove the palladium-on-carbon, the filtrate was evaporated under reduced pressure, and the residue was reprecipitated from methanol-ethanol to give 5'-amino-5-deoxyuridine (5'-$NH_2$-Urd) (2.22 g, yield 98%) as powders. A white solid.

vmax (KBr disc)/$cm^{-1}$: 3400, 1680, 1640, 1500, 1460, 1270, 1120, 1050

$^1$H NMR (270 MHz; DMS-$d_6$): δ2.74(2H,m,5'-H), 3.74 (1H,q,$J_{4',3'}$=$J_{4',5'}$=4.6,4'-H), 3.92(1H,t,$J_{3',2'}$=$J_{3',4'}$=4.8,3'-H), 4.05(1H,t,$J_{2',1'}$=$J_{2',3}$=5.5,2'-H), 5.11(4H,br,2'-OH,3'-OH,5'-$NH_2$), 5.62(1H,d,$J_{5,6}$7.8,5-H), 5.75(1H,d,$J_{1',2}$5.6,1'-H), 7.87 (1H,d,$J_{6,5}$8.0,6-H)

Found: C,42.81; H,5.63; N,16.98. Calc. for $C_9H_{13}N_3O_5$·½$H_2O$: C,42.86; H,5.59; N,16.66%: FAB MS(NBA): m/z 244(M+H).

Reference Production Example 2

Production of 5'-amino-5'-deoxycytidine
(5'-$NH_2$-Cyd)

A suspension of cytidine (9.72 g, 40.0 mmol) in pyridine (200 ml) was added to trimethylchlorosilane (25.6 ml, 200 mmol). After 15 minutes of stirring, benzoyl chloride (23.2 ml, 200 mmol) was added, and the reaction was allowed to proceed at room temperature for 2 hours. The reaction mixture was then cooled on an ice bath, and water (40 ml) was added. Five minutes later, 28% aqueous ammonia (40 ml) was added, and the mixture was stirred at room temperature for 15 minutes. Then, the solvent was distilled off under reduced pressure, and acetone was added to precipitate a white solid. The precipitate was filtered off and recrystallized from water to give $N^4$-benzoylcytidine (13.3 g, 96%). The $N^4$-benzoylcytidine (13.0 g, 37.4 mmol), triphenylphosphine (28.0 g, 107 mmol) and lithium azide (13.0 g, 266 mmol) were suspended in dried DMA, and carbon tetrabromide (35.5 g, 107 mmol) was added to the suspension. After 3 hours of stirring at room temperature, ethyl acetate (1500 ml) was added, and the mixture was washed with water and a saturated aqueous solution of sodium chloride (1000 ml each). The organic layer was dried over magnesium sulfate, and the solvent was evaporated under reduced pressure. The residue was recrystallized from methanol to give 5'-azido-5'-deoxy-$N^4$-benzoylcytidine (12.4 g, yield 89%). A solution of 5'-azido-5'-deoxy-$N^4$-benzoylcytidine (10.0 g, 26.9 mmol) in methanol-DMF (1:1 v/v, 100 ml) was vigorously stirred with 10% palladium-on-carbon (about 1.0 g) in a hydrogen atmosphere. The resulting mixture was filtered, and the filtrate was evaporated under reduced pressure to give 5'-amino-5'-deoxy-$N^4$-benzoylcyridine (9.04 g, yield 97%).

Then, the thus-obtained 5'-amino-5'-deoxy-$N^4$-benzoylcytidine (8.5 g, 24.5 mmol) was dissolved in 28% aqueous ammonia (200 ml), and the mixture was stirred at room temperature for 24 hours. The solution was evaporated to dryness, and acetone was added to recover 5'-amino-5'-deoxycytidine (5.76 g, yield 97%).

vmax (KBr disc)/$cm^{-1}$: 3400, 1690, 1660, 1470, 1320, 1220, 1120

$^1$H NMR (270 MHz; DMSO-$d_6$): δ2.75(2H,m,5'-H), 3.71 (1H,q,$J_{4',3}$=$J_{4',5}$=4.9,4'-H), 3.86(1H,$J_{3',2'}$=$J_{3',4'}$=5.4,3'-H), 3.93(1H,$J_{2',1'}$=$J_{2',3}$=4.4,2'-H), 4.95(3H,br,3'-OH,5'-$NH_2$), 5.25(1H,br,2'-OH), 5.71(1H,d,$J_{5,6}$7.3,5-H), 5.76(1H,d,$J_{1'}$, $_{2'}$4.4,1'-H), 7.14(1H,br,4-$NH_2$), 7.77(1H,d,$J_{6,5}$ 7.3,6-H)

Found: C,44.52; H,5.79; N,23.33. Calc. for $C_9H_{14}N_4O_4$: C,44.63; H,5.83; N,23.13%: FAB MS(NBA): m/z 243(M+H)

Reference Production Example 3

Production of 5'-amino-5'-deoxyinosine (5'-$NH_2$-Ins)

Inosine (890 mg, 3.0 mmol) was dried under reduced pressure for 1 hour. Thereto was added 1.02 g (21 mmol) of lithium azide, and the mixture was further dried for 1 hour. Distilled DMF (40 ml) was added to the reaction vessel, and the pressure was reduced for about 10 minutes with stirring. Further, 2.20 g (8.4 mmol) of triphenylphosphine was added and, after confirmation of the dissolution of triphenylphosphine, 2.78 g (8.14 mmol) of carbon tetrabromide was added to initiate the reaction. On that occasion, the solution turned yellow. After 8 hours, the completion of the reaction was confirmed by TLC, and the reaction was quenched with methanol. The solution was distilled under reduced pressure, and the residue was purified by silica gel column chromatography (mobile phase MeOH:$CHCl_3$=1:5) to give 5'-azido-5'-deoxyinosine. Isolation yield 775 mg, 88%.

The thus-obtained 5'-azido-5'-deoxyinosine was then dissolved in methanol and reduced with hydrogen for 12 hours using palladium-on-carbon Pd/C (10%, 80 mg) as a catalyst, whereby 5'-amino-5'-deoxyinosine was obtained. Yield 91%.

$^1$H NMR (270 MHz; DMSO-$d_6$): δ3.61(m,2H), 4.10(m, 8H), 4.63(m,2H), 5.40(d,1H), 5.63(d,1H), 5.90(d,1H), 8.08 (s,1H): IR (KBr) n 1610, 1695 $cm^{-1}$: MS (FAB): m/z 267($M^+$, 39.4): UV (phosphate buffer) λmax (ε) 258 nm Reference Production Example 4

Production of 5'-amino-5'-deoxythymidine
(5'-NH$_2$-Thd)

Thymidine (2.42 g, 10.0 mmol) was dried under reduced pressure for 1 hour. Thereto was added 2.20 g (4.5 eq) of lithium azide, and the mixture was further dried for 1 hour. Distilled DMF (50 ml) was added to the reaction vessel, and the pressure was reduced for about 10 minutes with stirring. Further, 3.41 g (1.3 eq) of triphenylphosphine was added and, after confirmation of the dissolution of triphenylphosphine, 4.97 g (1.5 eq) of carbon tetrabromide was added to initiate the reaction. On that occasion, the solution turned yellow. After 40 minutes, the completion of the reaction was confirmed by TLC, and the reaction was quenched with methanol. The solution was distilled under reduced pressure, and the residue was purified by silica gel column chromatography (mobile phase MeOH:CHCl$_3$=1:9) to give 5'-azido-5'-deoxythymidine.

$^1$H-NMR (DMSO, 270 MHz): δ1.79(s,3H), 2.01-2.32(m, 2H),3.56(d,J=5.4 Hz,2H), 3.83(q,J=Hz,1H), 4.19(m,1H), 5.42(d,4.4 Hz,1H), 6.20(t,J=6.84 Hz,1H), 7.50(s,1H), 11.35 (s,1H)

The thus-obtained 5'-azido-5'-deoxythymidine was then dissolved in methanol and reduced with hydrogen using 10% palladium/carbon as a catalyst, whereby 5'-amino-5'-deoxythymidine was obtained. Yield 1.734 g, 71.6%.

$^1$H-NMR (DMSO, 270 MHz): δ1.78(s,3H), 1.96-2.19(m, 2H), 2.62-2.76(d,J=5.37 Hz,2H), 3.64(q,1H), 4.19(m,1H), 6.14(t,J=6.84 Hz,1H), 7.66(s,1H)

Production Example 1

Poly(N$^γ$-(5'-deoxy-5'-uridyl)-L-glutamine) (PRNA1)

Pentachlorophenyl trichloroacetate (0.454 g, 1.10 mmol) and diisopropylethylamine (0.174 ml, 1.00 mmol) were carefully added to a solution of poly(L-glutamic acid) (0.129 g) in DMF (20 ml) at 0° C. with stirring. After 1 hour, the 5'-amino-5'-deoxyuridine (0.267 g, 1.10 mmol) produced as described in Reference Example 1 was added to the reaction mixture, and the whole mixture was heated at 60° C. for 10 hours. Then, the solvent was removed under reduced pressure, and ethanol was added to the residue to give poly(N$^γ$-(5'-deoxy-5'-uridyl)-L-glutamine) (0.314 g). A white solid.

UV (H$_2$O, pH 7.2) λmax=262 nm (ε=9.8×10$^3$); vmax (KBr disc)/cm$^{-1}$: 3350, 3100, 2900, 1680, 1540, 1460, 1390, 1260

$^1$H NMR (270 MHz; DMSO-d$_6$): δ1.88(2H,br,β-CH$_2$), 2.15(2H,br,γ-CH$_2$),3.34(1.81H,br,5'-H), 3.80(1.85H,m,3'-H, 4'-H), 4.07(0.92H,br,2'-H), 4.22(1H,br,α-CH), 5.17(0.93H,s, 3'-OH), 5.40(0.93H,s,2'-OH), 5.67(0.93H,br,5-H), 5.72 (0.93H,br,1'-H), 7.65(0.92H,br,6-H), 8.01(1.90H,m,α-NH, 5'-NH), 11.33(0.93H,br,3-NH)

Found: C,46.97; H,5.30; N,13.47. El. Anal. Calcd. for (C$_{14}$H$_{18}$N$_4$O$_7$)$_{0.53}$(C$_5$H$_7$NO$_3$)$_{0.47}$: C,47.01; H,5.28; N,13.48%:

Production Example 2

PRNA2

A peptide ribonucleic acid (PRNA2) having an oligo(γ-L-glutamic acid) skeleton was produced according to the following reaction formula:

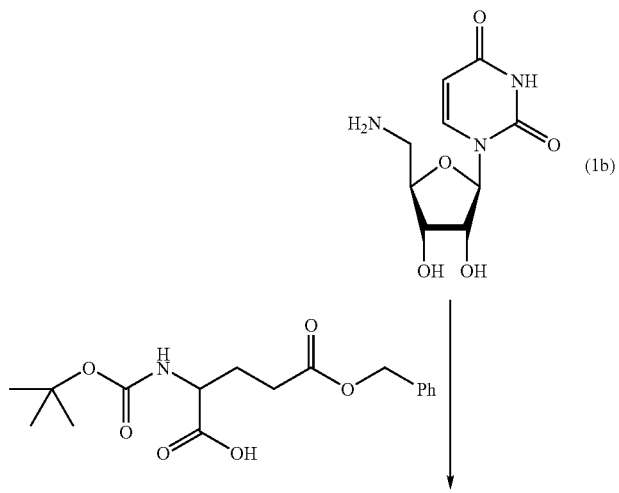

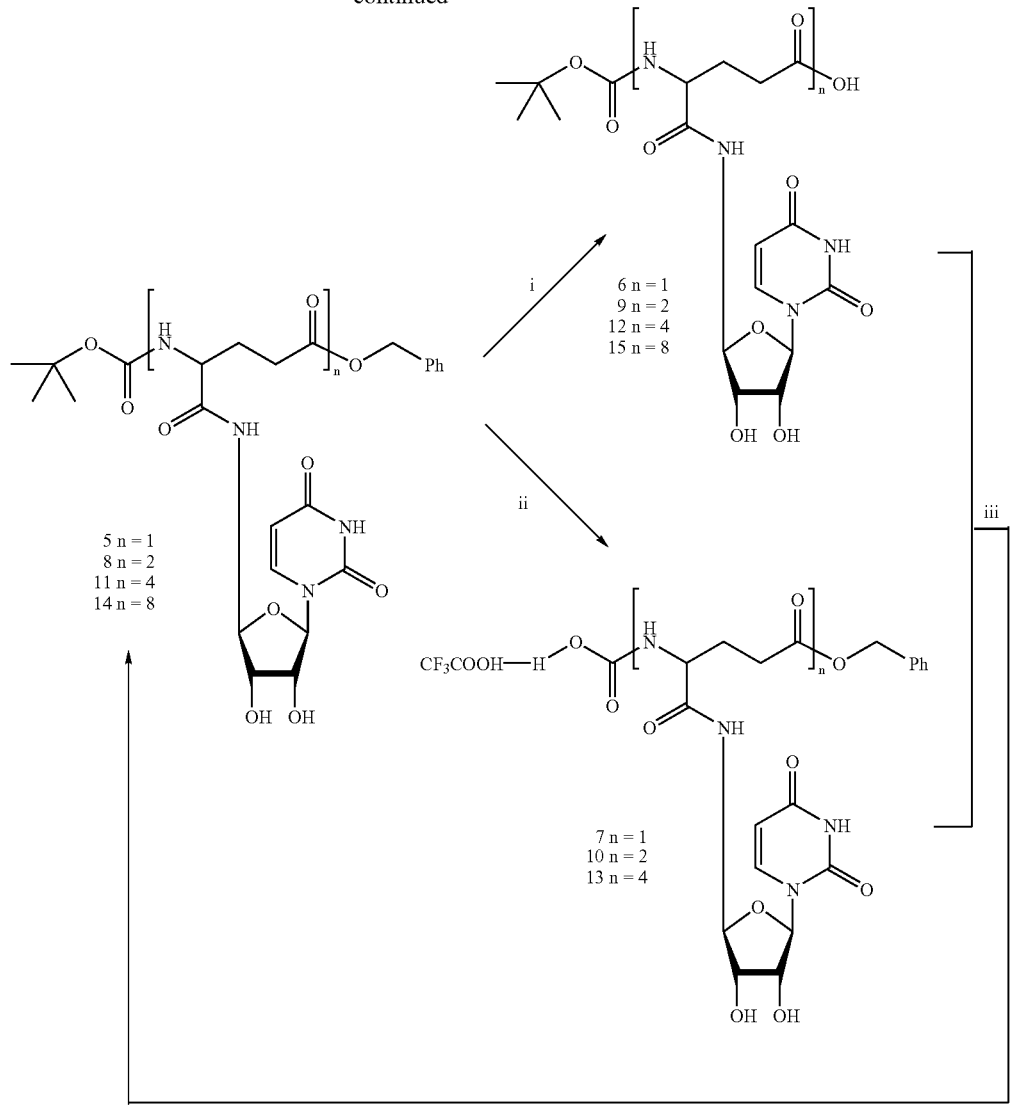

(1) Production of $N^4$-t-butoxycarbonyl-$N^5$- (5,'-deoxy-5'-uridyl)-L-isoglutamine benzyl ester (Boc-isoGln(5'U)-OBzl) (compound 5)

Diisopropylethylamine (1.30 ml. 7.47 mmol) was added to a DMF solution (100 ml) of glutamic acid with its amino terminus protected with a t-butoxycarbonyl group and its carbonyl group with a benzyl ester group, namely N-t-butoxycarbonyl-L-glutamic acid γ-benzyl ester (Boc-isoGln-OBzl) (2.52 g, 7.47 mmol), HOBt (1.01 g, 7.47 mmol) and the BOP reagent (benzotriazol-1-yloxytris(dimethylamino) phosphorium hexafluorophosphate) (3.30 g, 7.47 mmol). After 30 seconds of stirring at 0° C., the 5'-amino-5'-deoxyuridine (1b) (2.00 g, 8.22 mmol) produced in Reference Example 1 was added, and the reaction mixture was stirred at room temperature for 1 hour. After reaction, the solvent was distilled off under reduced pressure, and the residue obtained was suspended in ethyl acetate (200 ml). The suspension was thoroughly washed with an equal volume each of 4% sodium hydrogen carbonate, 5% potassium hydrogen sulfate and a saturated aqueous solution of sodium chloride. The organic layer was dried over magnesium sulfate and filtered, and the filtrate was concentrated under reduced pressure. The residue obtained was purified by column chromatography (solid phase; silica gel, mobile phase: chloroform-methanol (30:1 v/v) to give powdery Boc-isoGln(5'U)-Obzl (compound 5, n=1) (3.70 g, 88%).

νmax (KBr)/cm$^{-1}$: 3420, 1680, 1520, 1460, 1390, 1250, 1170

$^1$H-NMR (270 MHz; DMSO-$d_6$): δ1.37(9H,s,t-Bu—H), 1.77-1.88(2H,m,β-CH$_2$), 2.36(2H,t,$J_{\gamma,\beta}$=7.8,γ-CH$_2$), 3.29 (2H,m,5'-H), 3.83(2H,m,3'-H,4'-H), 3.94(1H,q,$J_{CH,NH}$=$J_{CH,\beta}$=7.3,Boc-NHC$\underline{H}$), 4.01(1H,q,$J_{2',1}$=$J_{2',3}$=5.4,2'-H), 5.07 (2H,s,PhCH$_2$), 5.18(1H,d,$J_{OH,3'}$=4.9,3'-OH), 5.40(1H,d,$J_{OH,2'}$=5.4,2'-OH), 5.63(1H,d,$J_{5,6}$8.3,5-H), 5.74(1H,d,$J_{1',2'}$=5.9,1'-H), 6.94(1H,d,$J_{NH,CH}$=7.8,Boc-NH), 7.35(5H,m,Ar—H), 7.64(1H,d,$J_{6,5}$=7.8,6-H), 8.00(1H,t,$J_{NH,5'}$=5.6,5'-NH), 11.35 (1H,s,3-NH), Found: C,55.06; H,6.02; N,9.76. Calc. for $C_{26}H_{34}N_4O_{10}\cdot¼H_2O$: C,55.07; H,6.13; N,9.88%: MALDI-TOF HRMS (α-CHCA), m/z found 585.220 (M+Na), calculated 585.217

(2) Production of N$^\alpha$-t-butoxycarbonyl-N$^5$-(5'-deoxy-5'-uridyl)-L-isoglutamine (Boc-isoGln(5'U)-OH) (Compound 6, n=1), (i)

Palladium-on-carbon (10%, about 0.2 g) was added to a solution of the Boc-isoGln(5'U)-OBzl (1.80 g, 3.20 mmol) (5) obtained as described above in methanol (50 ml). The mixture was continuously stirred in a hydrogen atmosphere (1 atm) for 2 hours, the reaction mixture was then filtered, and the filtrate was evaporated under reduced pressure to give powdery Boc-isoGln(5'U)-OH (1.44 g, yield 95%).

νmax (KBr)/cm$^{-1}$: 3320, 1680, 1530, 1460, 1390, 1250, 1170

$^1$H-NMR (270 MHz; DMSO-d$_6$): δ1.37(9H,s,t-Bu—H), 1.69-1.82(2H,m,β-CH$_2$), 2.19(2H,t,J$_{\gamma,\beta}$=7.3,γ-CH$_2$), 3.29-3.39(2H,m,5'-H), 3.83(2H,m,3'-H,4'-H), 3.92(1H,q,J$_{CH,NH}$=J$_{CH,\beta}$=5.9,Boc-NHC<u>H</u>), 4.02(1H,t,J$_{2',1}$=J$_{2',3}$=4.9,2'-H), 5.63(1H,d,J$_{5,6}$=8.3,5-H), 5.73(1H,d,J$_{1',2'}$=5.9,1'-H), 6.92(1H,d,J$_{NH,CH}$=8.3,Boc-NH), 7.65(1H,d,J$_{6,5}$=7.8,6-H), 7.98(1H,t,J$_{NH,5'}$=5.4,4,5'-NH), 11.35(1H,s,3-NH), MALDI-TOF HRMS (α-CHCA), m/z found 495.174 (M+Na), calculated 495.170

(3) Production of N$^5$-(5'-deoxy-5'-uridyl)-L-isoglutamine benzyl ester trifluoroacetate (TFA.isoGln(5'U)-OBzl) (Compound 7, n=1), (ii)

The Boc-isoGln(5'U)-OBzl (1.80 g, 3.20 mmol) obtained as described above under (1) was dissolved in TFA (10 ml), and the solution was allowed to stand at 0° C. for 30 minutes. The TFA was then distilled off under reduced pressure, and 200 ml of ester was added to give powdery TFA.isoGln(5'U)-OBzl (1.81 g, yield 98%).

νmax (KBr)/cm$^{-1}$: 3420, 1680, 1560, 1460, 1270, 1200, 1130

$^1$H-NMR (270 MHz; DMSO-d$_6$): δ1.97(2H,m,β-CH$_2$), 2.44(2H,t,J$_{\gamma,\beta}$=8.1,γ-CH$_2$), 3.82(3H,m,NH$_3^+$CH,3'-H,4'-H), 4.11(1H,q,J$_{2',1}$=J$_{2',3}$=5.2,2'-H), 5.08(2H,s,PhCH$_2$), 5.24(1H,d,J$_{OH,3'}$=4.9,3'-OH), 5.47(1H,d,J$_{OH,2}$=5.4,2'-OH), 5.63(1H,d,J$_{5,6}$=8.3,5-H), 5.75(1H,d,J$_{1',2}$=5.4,1'-H), 7.36(5H,m,Ar—H), 7.66(1H,d,J$_{6,5}$=8.3,6-H), 8.10(3H,br,NH$_3^+$), 8.62(1H,t,J$_{NH,5}$,5.4,5'-NH), 11.37(1H,s,3-NH), MALDI-TOF HRMS (α-CHCA), m/z found 463.178(M—CF$_3$COO), calculated 463.183

(4) Production of a Dimer (Boc-(isoGln(5'U))$_2$-OBzl) (Compound 8), Process (iii)

Diisopropylethylamine (0.97 ml. 5.57 mmol) was added to a DMF solution (50 ml) of the Boc-isoGln(5'U)-OH (compound 6) (1.25 g, 2.65 mmol) obtained in the above process (2), HOBt (0.358 g, 2.65 mmol) and the BOP reagent (1.17 g, 2.65 mmol). After 30 seconds of stirring at 0° C., the TFA.isoGln(5'U)-OBzl (compound 7) (1.68 g, 2.92 mmol) produced in the above process (3) was added, and the reaction mixture was stirred at room temperature for 2 hours. After reaction, the solvent was distilled off under reduced pressure, and the residue obtained was purified by column chromatography (solid phase; silica gel, mobile phase: chloroform-methanol (10:1 v/v) to give powdery Boc-(isoGln(5'U))$_2$-OBzl (compound 8, n=2) (1.70 g, yield 70%).

νmax (KBr)/cm$^{-1}$: 3420, 1680, 1540, 1380, 1270, 1200

$^1$H-NMR (270 MHz; DMSO-d$_6$): δ1.36(9H,s,t-Bu—H), 1.80(4H,m,β-CH$_2$), 2.15(2H,t,J$_{\gamma,\beta}$=7.1,γ-CH$_2$), 2.35(2H,t,J$_{\gamma,\beta}$=7.8,γ-CH$_2$), 3.83(5H,m,Boc-NHC<u>H</u>,3'-H and 4'-H), 4.03(2H,q,J$_{2',1}$=J$_{2',3}$=4.4,2'-H), 4.26(1H,q,J$_{CH,NH}$=J$_{Ch,\beta}$=7.3,α-CH), 5.06(2H,s,PhCH$_2$), 5.16(2H,s,3'-OH), 5.39(2H,d,J$_{OH,2'}$=4.4,2'-OH), 5.62(1H,d,J$_{5,6}$=8.3,5-H), 5.64(1H,d,J$_{5,6}$=7.8,5-H), 5.73(1H,d,J$_{1',2'}$=5.9,1'-H), 6.85(1 H,d,J$_{NH,CH}$=8.3,Boc-NH), 7.35(5H,m,Ar—H), 7.63(1H,d,J$_{6,5}$=7.8,6-H), 7.64(1H,d,J$_{6,5}$=7.8,6-H), 7.95(2H,m,5'-NH), 8.14(1H,t,J$_{NH,CH}$=10.7,α-NH), 11.33(2H,s,3-NH); MALDI-TOF HRMS (α-CHCA), m/z found 939.339 (M+Na), calculated 939.335

(5) Production of a Dimer (Boc-(isoGln(5'U))$_2$-OH) (Compound 9, n=2), Process (i)

Palladium-on-carbon (10%, about 0.1 g) was added to a solution of the Boc-(isoGln(5'U))$_2$-OBzl (0.850 g, 0.927 mmol) (8) obtained as described above in methanol (50 ml). The mixture was continuously stirred in a hydrogen atmosphere (1 bar) for 4 hours, the reaction mixture was then filtered, and the filtrate was evaporated under reduced pressure to give powdery Boc-(isoGln(5'U))$_2$-OH (compound 9) (0.736 g, yield 96%).

νmax (KBr)/cm$^{-1}$: 3390, 1680, 1540, 1470, 1390, 1280

$^1$H-NMR (270 MHz; DMSO-d$_6$): δ1.37(9H,s,t-Bu—H), 1.67-1.81(4H,m,β-CH$_2$), 2.14(4H,m,γ-CH$_2$), 3.58(4H,m,5'-H), 3.92(4H,m,3'-H and 4'-H), 4.03-4.24(3H,m,2'-H and Boc-NHC<u>H</u>), 4.42(1H,q,J$_{CH,NH}$=J$_{CH,\beta}$=7.1,α-CH), 5.17-5.39(4H,m,2'-OH and 3'-OH), 5.67(2H,d,J$_{5,6}$=8.3,5-H), 5.86(2H,d,J$_{1',2'}$=7.8,1'-H), 6.99(1H,d,J$_{NH,CH}$=8.8,Boc-NH), 7.67(2H,d,J$_{6,5}$=8.8,6-H), 7.88(2H,m,5'-NH), 8.16(1H,m,α-NH), 11.35(2H,s,3-NH); MALDI-TOF HRMS (α-CHCA), m/z found 849.293 (M+Na), calculated 849.288.

(6) Production of a Dimer (TFA.isoGln(5'U)$_2$-OBzl) (Compound 10, n=2), (ii)

The Boc-(isoGln(5'U))$_2$-OBzl (compound 8) (0.85 g, 0.927 mmol) obtained as described above under (4) was dissolved in TFA (5 ml), and the solution was allowed to stand at 0° C. for 30 minutes. The TFA was then distilled off under reduced pressure, and 100 ml of ether was added to give powdery TFA.isoGln(5'U)$_2$-OBzl (compound 10) (0.846 g, yield 98%).

νmax (KBr)/cm$^{-1}$: 3420, 1680, 1540, 1470, 1280, 1200, 1140;

$^1$H-NMR (270 MHz; DMSO-d$_6$): δ1.89(4H,m, β-CH$_2$), 2.25-2.34(4H,m, γ-CH$_2$), 3.59(4H,m,5'-H), 3.86(6H,m,NH$_3^+$CH, α-CH,3'-H, 4'-H), 4.11(2H,m,2'-H), 5.08(2H,s,PhCH$_2$), 5.20(2H,m,3'-OH), 5.70(2H,d,J$_{5,6}$=7.8,5-H), 5.77(2H,d,J$_{1',2'}$=5.9,1'-H), 7.36(5H,m,Ar—H), 7.89(1 H,m,5'-NH), 8.10 (4H,m,α-NH,NH$_3^+$), 8.56(1H,m,5'-NH), 11.32(2H,s,3-NH); MALDI-TOF HRMS (α-CHCA), m/z found 817.296 (M-CF$_3$COO), calculated 817.301.

(7) Production of a Tetramer (Boc-(isoGln(5'U))$_4$-OBzl) (Compound 11), Process (iii)

Diisopropylethylamine (0.29 ml. 1.68 mmol) was added to a DMF solution (30 ml) of the dimer Boc-isoGln(5'U)$_2$-OH (compound 9) (0.662 g, 0.801 mmol) obtained as described above under (5), HOBt (0.108 g, 0.801 mmol) and the BOP reagent (0.354 g, 0.801 mmol). After 30 seconds of stirring at 0° C., the TFA.isoGln(5'U)$_2$-OBzl (compound 10) (0.82 g, 0.881 mmol) produced as described above under (6) was added, and the reaction mixture was stirred at room temperature for 2 hours. After reaction, the solvent was distilled off under reduced pressure, and the residue obtained was purified by column chromatography (solid phase; silica gel, mobile phase: chloroethanol) to give powdery Boc-(isoGln(5'U))$_4$-OBzl (compound 11) (1.22 g, yield 94%).

νmax (KBr)/cm$^{-1}$: 3300, 1680, 1540, 1460, 1390, 1270, 1080;

$^1$H-NMR (270 MHz; DMSO-d$_6$): δ1.37(9H,s,t-Bu—H), 1.71-1.82(8H,m, β-CH$_2$), 2.14(6H,m, γ-CH$_2$), 2.35(2H,t,J$_{\gamma,\beta}$=7.6,γ-CH$_2$), 3.26-3.44(8H,m,5'-H), 3.83(9H,m,Boc-NHC<u>H</u>,3'-H and 4'-H), 4.04(4H,m,2'-H), 4.22(3H,m, α-CH), 5.06 (2H,s,PhCH$_2$), 5.16(4H,d,J$_{OH,3'}$=4.4,3'-OH), 5.39(4H,d,J$_{OH,2'}$=5.4,2'-OH), 5.65(4H,d,J$_{5,6}$=7.3,5-H), 5.73(4H,d,J$_{1',2'}$=3.9,1'-H), 6.87(1H,d,J$_{NH,CH}$=7.8,Boc-NH), 7.35(5H,m,Ar—H), 7.65(4H,d,J$_{6,5}$=8.3,6-H), 7.96(4H,m,5'-NH), 8.12(3H,m,α-NH), 11.34(4H,s,3-NH); MALDI-TOF HRMS (α-CHCA), m/z found: 1647.57 (M+Na), calculated 1647.570.

(8) Production of a Tetramer (Boc-(isoGln(5'U))$_4$-OH) (Compound 12), Process (i)

Palladium-on-carbon (10%, about 0.1 g) was added to a solution of the Boc-(isoGln(5'U))$_4$-OBzl (0.600 g, 0.369 mmol) (11) obtained as described above under (7) in methanol-DMF (1:1 v/v, 30 ml). The mixture was continuously stirred in a hydrogen atmosphere (1 bar) for 4 hours, the reaction mixture was then filtered, and the filtrate was evaporated under reduced pressure to give a powdery tetramer, Boc-(isoGln(5'U))$_4$-OH (compound 12)(0.550 g, yield 97%).

νmax (KBr)/cm$^{-1}$: 3420, 1680, 1540, 1490, 1380, 1210, 1130;

$^1$H-NMR (270 MHz; DMSO-d$_6$): δ1.37(9H,s,t-Bu—H), 1.69-1.82(8H,m, β-CH$_2$), 2.15(8H,m, γ-CH$_2$), 3.85(9H,m, Boc-NHCH,3'-H and 4'-H), 4.04(4H,m,2'-H), 4.20(3H,m, α-CH), 5.21(4H,br,3'-OH), 5.37(4H,br,2'-OH), 5.64(4H,d,J$_{5,6}$=7.8,5-H), 5.73(4H,d,J$_{1',2'}$=5.9,1'-H), 6.87(1H,d,J$_{NH,CH}$=8.3,Boc-NH), 7.65(4H,d,J$_{6,5}$=8.3,6-H), 7.95(4H,m,5'-NH), 8.13(3H,m, α-NH), 11.33(4H,s,3-NH); MALDI-TOF HRMS (α-CHCA), m/z found 1557.52 (M+Na), calculated 1557.523.

(9) Production of a Tetramer (TFA.isoGln(5'U)$_4$-OBzl (Compound 13), Process (ii)

The Boc-(isoGln(5'U))$_4$-OBzl (compound 11) (0.600 g, 0.369 mmol) obtained as described above under (7) was dissolved in TFA (5 ml), and the solution was allowed to stand at 0° C. for 30 minutes. The TFA was then distilled off under reduced pressure, and 100 ml of ether was added to give powdery TFA.isoGln(5'U)$_4$-OBzl (compound 13) (0.593 g, yield 98%).

νmax (KBr)/cm$^{-1}$: 3420, 1680, 1540, 1460, 1390, 1270, 1130

$^1$H-NMR (270 MHz; DMSO-d$_6$): δ1.76-1.89(8H,m, β-CH$_2$), 2.13-2.25(6H,m, γ-CH$_2$), 2.34(2H,t,J$_{γ,β}$=8.3, γ-CH$_2$), 3.83(9H,m,NH$_3^+$CH,3'-H and 4'-H), 4.05-4.22(7H, m, α-CH and 2'-H), 5.06(2H,s,PhCH$_2$), 5.16(3H,m,3'-OH), 5.24(1H,d,J$_{OH,3'}$=4.9,3'-OH), 5.42(3H,m,2'-OH), 5.48(1H,d, J$_{OH,2'}$=5.4,2'-OH), 5.64(4H,m,5-H), 5.73(4H,m,1'-H), 7.35 (5H,m,Ar—H), 7.66(4H,m,6-H), 7.95(3H,m,5'-NH), 8.13(6H,m, α-NH and NH$_3^+$), 8.61(1H,m,5'-NH), 11.35(4H, m,3-NH); MALDI-TOF HRMS (α-CHCA), m/z found 1548.52 (M-CF$_3$COO+Na), calculated 1548.526.

(10) Production of an Octamer (Boc-(isoGln(5'U))$_8$-OBzl) (Compound 14), Process (iii)

Diisopropylethylamine (0.11 ml. 0.641 mmol) was added to a DMF solution (30 ml) of the tetramer Boc-isoGln(5'U)$_4$-OH (compound 12) (0.468 g, 0.305 mmol) obtained as described above under (8), HOBt (0.041 g, 0.305 mmol) and the BOP reagent (0.135 g, 0.305 mmol). After 30 seconds of stirring at 0° C., the TFA.isoGln(5'U)$_4$-OBzl (compound 13) (0.550 g, 0.335 mmol) obtained as described above under (9) was added, and the reaction mixture was stirred at room temperature for 4 hours. After reaction, the solvent was distilled off under reduced pressure, and methanol was added to the residue, whereby a powdery octamer, Boc-(isoGln(5'U))$_8$-OBzl (compound 14) (0.854 g, yield 92%) was obtained.

νmax (KBr)/cm$^{-1}$: 3420, 1680, 1530, 1460, 1400, 1270, 1130;

$^1$H-NMR (270 MHz; DMSO-d$_6$): δ1.37(9H,s,t-Bu—H), 1.71-1.82(16H,m, β-CH$_2$), 2.14(14H,m, γ-CH$_2$), 2.34(2H,t, J$_{γ,β}$=7.8, γ-CH$_2$), 3.25-3.42(16H,m,5'-H), 3.83(17H,m, Boc-NHCH,3'-H and 4'-H), 4.05(8H,m,2'-H), 4.20(7H,m, α-CH), 5.06(2H,s,PhCH$_2$), 5.15(8H,d,J$_{OH,3'}$=3.4,3'-OH), 5.39(8H,d, J$_{OH,2'}$=5.4,2'-OH), 5.64(8H,d,J$_{5,6}$=7.8,5-H), 5.73(8H,d,J$_{1',2'}$=5.4,1'-H), 6.87(1H,d,J$_{NH,CH}$=7.3,Boc-NH), 7.35(5H,m, Ar—H), 7.64(8H,d,J$_{6,5}$=7.8,6-H), 7.95(8H,m,5'-NH), 8.13(7H,m, α-NH), 11.33(8H,s,3-NH); MALDI-TOF HRMS (α-CHCA), m/z found 3064.04 (M+Na), calculated 3064.041.

(11) Production of an Octamer(Boc-(isoGln(5'U))$_8$OH) (Compound 15), Process (i)

Palladium-on-carbon (10%, about 0.1 g) was added to a solution of the octamer (Boc-(isoGln(5'U))$_8$-Obzl) (compound 14) (0.800 g, 0.263 mmol) obtained as described above under (10) in methanol-DMF (1:3 v/v, 50 ml). The mixture was continuously stirred in a hydrogen atmosphere (1 bar) for 6 hours, the reaction mixture was then filtered, and the filtrate was evaporated under reduced pressure to give powdery Boc-(isoGln(5'U))$_8$-OH (compound 15) resulting from elimination of the C-terminal protective group benzyl (0.745 g, yield 96%).

νmax (KBr)/cm$^{-1}$: 3410, 1680, 1540, 1470, 1390, 1260, 1110

$^1$H-NMR (270 MHz; DMSO-d$_6$): δ1.37(9H,s,t-Bu—H), 1.70-1.82(16H,m, β-CH$_2$), 2.15(16H,m, γ-CH$_2$), 3.83(17H, m,Boc-NHCH,3'-H and 4'-H), 4.05(8H,m,2'-H), 4.19(7H,m, α-CH), 5.18(8H,m,3'-OH), 5.29(8H,m,2'-OH), 5.65(8H,d,J$_{5,6}$=7.8,5-H), 5.73(8H,d,J$_{1',2'}$=5.9,1'-H), 6.88(1H,d,J$_{NH,CH}$=8.8,Boc-NH), 7.65(8H,d,J$_{6,5}$=8.3,6-H), 7.95(8H,m,5'-NH), 8.14(8H,m, α-NH), 11.33(8H,s,3-NH); MALDI-TOF HRMS (α-CHCA), m/z found 2973.99 (M+Na), calculated 2973.994.

Production Example 3

A PRNA2 having a free N terminus was prepared according to the following reaction formula:

15

↓i

-continued

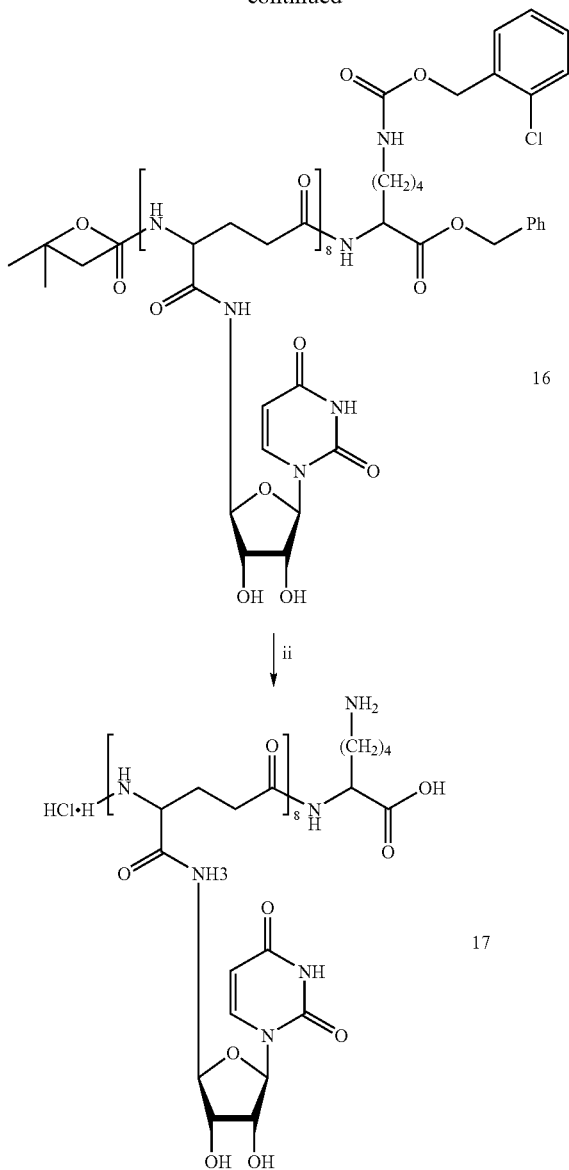

16

17

(1) Production of Boc-(isoGln(5'U)8-Lys(ClZ)-Bzl (Compound 16), Process (i)

Diisopropylethylamine (0.04 ml. 0.237 mmol) was added to a DMF solution (30 ml) of the octamer Boc-(isoGln(5'U))$_8$-OH (compound 15) (0.700 g, 0.237 mmol) obtained in Example 2 (11), HOBt (0.032 g, 0.237 mmol) and the BOP reagent (0.105 g, 0.237 mmol). After 30 seconds of stirring at 0° C., N$^\epsilon$-2-chlorobenzyloxycarbonyl-O-benzyl-L-lysine (0.106 g, 0.261 mmol) was added, and the mixture was stirred at room temperature for 4 hours. After reaction, the solvent was distilled off under reduced pressure, and methanol was added to the residue, whereby powdery Boc-(isoGln(5'U))$_8$-Lys(ClZ)-Bzl (compound 16) (0.712 g, yield 90%) was obtained.

νmax (KBr)/cm$^{-1}$: 3330, 1680, 1540, 1470, 1390, 1270, 1130

$^1$H-NMR (270 MHz; DMSO-d$_6$): δ1.36(13H,m,t-Bu—H, γ-CH$_2$(Lys) and δ-CH$_2$(Lys)), 1.57-1.84(18H,m, β-CH$_2$(Glu) and β-CH$_2$(Lys)), 2.14(16H,m, β-CH$_2$(Glu)), 2.98(2H,m, ε-CH$_2$(Lys)), 3.83(17H,m,Boc-NHC$\underline{H}$,3'-H and 4'-H), 4.05 (8H,m,2'-H), 4.20(8H,m, α-CH), 5.07(2H,s,PhCH$_2$), 5.08 (2H,s,Cl-PhCH$_2$), 5.16(8H,d,J$_{OH,3'}$=3.9,3'-OH), 5.39(8H,d, J$_{OH,2'}$=5.4,2'-OH), 5.65(8H,d,J$_{5,6}$=7.8,5-H), 5.73(8H,d,J$_{1'}$, $_{2'}$=5.9,1'-H), 6.87(1H,d,J$_{NH,CH}$=7.3,Boc-NH), 6.99(1H,m, ε-NH(Lys)), 7.35(5H,m,Ar—H(Bzl)), 7.45(4H,m,Ar—H (Cl-Z)), 7.65(8H,d,J$_{6,5}$=7.8,6-H), 7.96(8H,m,5'-NH), 8.14(8H,m, α-NH), 11.33(8H,s,3-NH); MALDI-TOF HRMS (α-CHCA), m/z found 3360.13 (M+Na), calculated 3360.134

(2) Production of HCl.(isoGln(5'U))$_8$-Lys-OH (compound 17), Process (ii)

The Boc-(isoGln(5'U))$_8$-Lys(ClZ)-Bzl (compound 16) (0.300 g, 0.090 mmol) obtained as described above under (1) was dissolved in TFA (10 ml), and the solution was stored at −10° C. in a nitrogen atmosphere. Thioanisole (1.84 ml, 15.7 mmol), m-cresol (0.97 ml, 9.27 mmol) and trimethylsilyl triflate (3.00 ml, 16.6 mmol) were added in that order, and the mixture was stirred at 0° C. for 1 hour. Ether (200 ml) was added, and the resulting precipitate was filtered off and dissolved in 5% aqueous ammonia. After 30 minutes, the solvent was distilled off under reduced pressure, and the residue was treated with 4 M hydrochloric acid in dioxane for 30 minutes. The solvent was distilled off, and the residue was purified by gel filtration and reversed phase HPLC to give powdery HCl. (isoGln(5'U))$_8$-Lys-OH (compound 17) (0.223 g, yield 82%).

νmax (KBr)/cm$^{-1}$: 3420, 1680, 1540, 1460, 1390, 1270, 1110;

$^1$H-NMR (270 MHz; DMSO-d$_6$): δ1.35(4H,m, γ-CH$_2$ (Lys), δ-CH$_2$(Lys)), 1.70-1.83(16H,m, β-CH$_2$(Glu)), 2.14(16H,m, γ-CH$_2$(Glu)), 2.98(2H,m, ε-CH$_2$(Lys)), 3.84 (17H,m,NH$_3^+$CH,3'-H and 4'-H), 4.06(8H,m,2'-H), 4.20(8H, m, α-CH), 5.17(8H,m,3'-OH), 5.41(8H,m,2'-OH), 5.65(8H, d,J$_{5,6}$=7.8,5-H), 5.73(8H,d,J$_{1',2'}$=5.9,1'-H), 7.24(2H,br, ε-NH$_2$), 7.65(8H,d,J$_{6,5}$=7.8,6-H), 7.95(7H,m,5'-NH), 8.14(11H,m, α-NH and NH$_3^+$), 8.59(1H,m,5'-NH),11.34 (8H,m,3-NH); MALDI-TOF HRMS (α-CHCA), m/z found 2980.86 (M-HCl), calculated 2980.055.

Production Example 4

Production of Boc-AEG(5'U)-OBn Oligomer (PRNA3)

(1) Production of Boc-AEG-OBn

Boc-AEG-OBn was produced according to the following reaction formula:

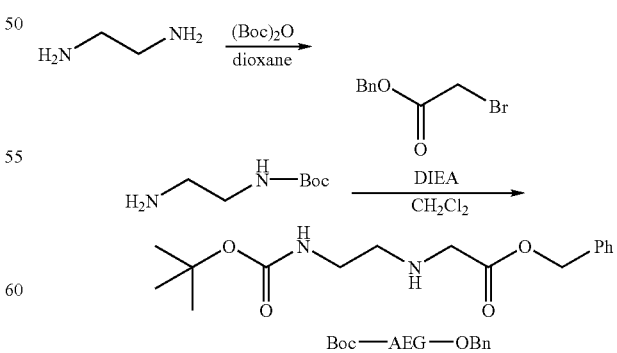

Boc—AEG—OBn

① Synthesis of N-Boc-1,2-aminoethane

To a solution of ethylenediamine (52.5 g, 874 mmol) in dioxane (300 ml) was added dropwise with stirring a di-tertbutyl dicarbonate ((Boc)₂O) in dioxane (300 ml) over 10 hours. After the dropping, stirring was continued for 24 hours. After completion of the reaction, the dioxane was distilled off under reduced pressure, and 400 ml of water was added to the residue. The insoluble matter was removed by filtration, and the aqueous layer was extracted with chloroform (500 ml×4). The organic layers were combined and dried over magnesium sulfate. After drying, the filtrate was concentrated under reduced pressure and purified by column chromatography (silica gel; chloroform-methanol (10:1 v/v) to give N-Boc-1, 2-aminoethane (14.6 g, 91.4 mmol, yield 81% (based on Boc₂O). A white solid.

② Synthesis of Boc-AEG-OBn

The N-Boc-1,2-aminoethane (4.64 g, 29.0 mmol) and diisopropylethylamine (4.50 g, 34.8 mmol) were dissolved in chloroform (40 ml), and a solution of benzyl bromoacetate (6.57 g, 28.7 mmol) in chloroform (30 ml) was added dropwise thereto with stirring over 1 hour. After completion of the dropping, stirring was continued for 24 hours. The solvent was distilled off under reduced pressure, and the residue was purified by column chromatography (silica gel; ethyl acetate alone) to give Boc-AEG-OBn (7.00 g, 22.7 mmol, yield 79%). A colorless liquid.

δH (270 MHz; DMSO-$d_6$): 1.31(9H,s,t-Bu—H), 2.49(2H, t,J6.6,BocNHCH₂-CH₂), 2.92(2H,m,Boc-NH—CH₂), 3.31 (2H,s,CH₂—COOBn), 5.06(2H,s,Ph—CH), 6.67(1H,br, Boc-NH), 7.26-7.31(5H,m,Ar—H)

(2) Production of Boc-AEG(5'U)-OBn

Boc-AEG(5'U)-OBn was produced according to the following reaction formula:

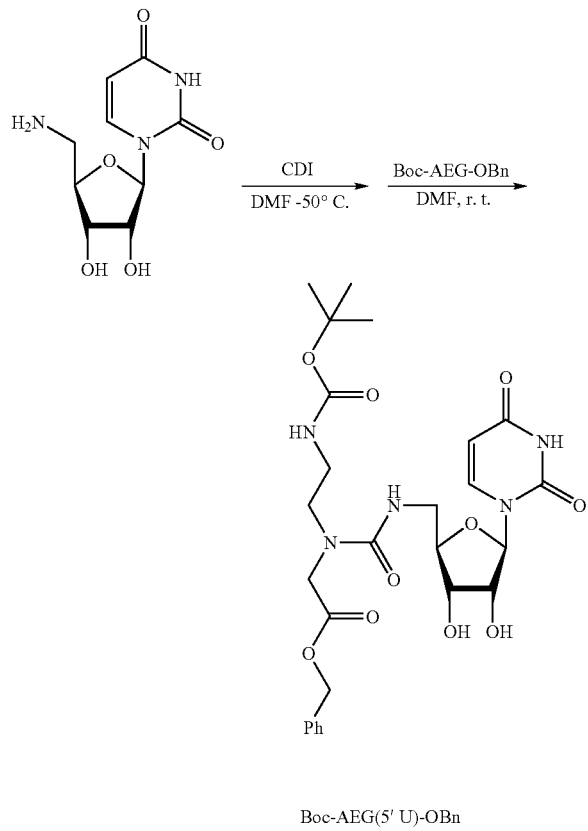

Boc-AEG(5' U)-OBn

The 5'-amino-5'-deoxyuridine (5'-NH₂-Urd) (1.80 g, 7.40 mmol) prepared in Reference Production Example 1 was dissolved in dried DMF (50 ml), and a solution of CDI (1.14 g, 7.04 mmol) in DMF (40 ml) was added dropwise with stirring at −50° C. over 1 hour. The reaction system was stirred at −50° C. for 30 minutes, then the Boc-AEG-OBn (1.72 g, 7.40 mmol) produced as described above was added, and the mixture was stirred at room temperature for 2 days. After completion of the reaction, the DMF was distilled off under reduced pressure at room temperature, and the residue was purified by column chromatography (silica gel; chloroform-methanol (20:1 v/v)) to give Boc-AEG(5'U)-OBn (2.64 g, 4.58 mmol, yield 65%). A white solid.

νmax (KBr)/cm⁻¹: 3380, 1690, 1540, 1460, 1390, 1250, 1170

δH(270 MHz; DMSO-$d_6$): 1.35(9H,s,t-Bu—H), 2.9-3.1 (2H,m,Boc-NHCH), 3.2-3.4(4H,m,BocNHCH₂-CH$_{25}$,'-H), 3.85(1H,q,4'-H), 3.89(1H,q,3'-H), 4.01(1H,q,2'-CH), 4.06 (2H,s,CH₂COOBn), 5.08(1H,d,$J_{3'\text{-}OH,3'\text{-}H}$,4.9,3'-OH), 5.11 (2H,s,Ph—CH₂), 5.35(1H,d,$J_{2'\text{-}OH,2'\text{-}H}$ 5.7,2'-OH), 5.60(1H, d,$J_{5,6}$ 10.5,5-H), 5.70(1H,d,$J_{1',2'\text{-}H}$ 5.4.5,1'-H), 6.65(1H,br,5'-NH), 6.77(1H,br,Boc-NH), 7.31-7.36(5H,m,Ar—H), 7.64 (1H,d,$J_{6,5}$ 7.8,6-H), 11.33(1H,s,3-NH); m/z (FAB) 600 (M+Na)⁺.

(3) Production of Boc-AEG(5'U)-OH

Palladium-on-carbon (Pd/C, 10 wt % Pd, 0.02 g) was added to a methanol solution (30 ml) of the Boc-AEG(5'U)-OBn (0.2 g, 0.35 mmol) obtained as described above, and the reaction was allowed to proceed while bubbling hydrogen with stirring for 1 hour. After completion of the reaction, the Pd/C was filtered off, and the filtrate was concentrated under reduced pressure. The residue was recrystallized from methanol-ethanol to give Boc-AEG(5'U)-OH (0.16 g, 0.33 mmol, yield 95%). A white solid.

νmax (KBr)/cm⁻¹: 3390, 1690, 1540, 1460, 1400, 1250, 1170

δH(270 MHz; DMSO-$d_6$): 1.35(9H,s,t-Bu—H), 3.01(2H, m,Boc-NHCH₂), 3.15-3.33(4H,m,Boc-NHCH₂-CH$_{25}$,'-H₂), 3.78-3.82(2H,m,HN—CH—CO,4'-H), 3.89-3.91(3H,m,3'H, CH₂COOH), 3.98-4.00(1H,m,2'-H), 5.07(1H,br,3'-OH), 5.32(1H,d,$J_{2'\text{-}OH,2'\text{-}H}$ 5.0,2'-OH), 5.62(1H,d,$J_{5,6}$ 8.4,5-H), 5.62 (1H,d,$J_{1',2'\text{-}H}$5.9,1'-H), 6.57(1H,br,5'-NH), 6.77(1H,t,$J_{Boc\text{-}NH,5'}$ 4.7, Boc-NH), 7.63(1H,d,$_{6,5}$ 8.1,6-H), 11.32(1H,s,3-NH); m/z (FAB) 510 (M+Na)⁺.

(4) Process for Producing TFA.AEG(5'U)-OBn

The Boc-AEG(5'U)-OBn obtained as described above under (2) was dissolved in TFA, and the solution was allowed to stand at 0° C. for 30 minutes. The TFA was then distilled off under reduced pressure, and ester was added, whereby TFA.AEG(5'U)-OBn was obtained.

(5) Oligomer Production

A dimer, Boc-(AEG(5'U))₂-OBn is prepared using the Boc-AEG(5'U)-OH and TFA.AEG(5'U)-OBn prepared as described above and following the process of Production Example 2 (4). Further, oligomers can be prepared according to the processes of Production Example 2 (5) to (11).

Production Example 5

(1) Production of a Trimer (Boc-(isoGln(5'U))₃-OBzl)

The Boc-(isoGln(5'U))₄-OH (compound 9) (343 mg, 0.37 mmol) obtained in Example 2 (5), HOBt (56 mg, 1 eq) and the BOP reagent (184 mg, 1 eq) were dissolved in distilled DMF at 0° C., and the solution was stirred for about 1 hour until returning to room temperature. To this solution was added diisopropylethylamine (DIEA) (131 mg, 2 eq), and the TFA.i-soGln(5'U)-OBzl (compound 7) (251 mg, 1 eq) obtained in Example 2 (3) was then added, and the mixture was stirred at room temperature for 2 hours. After reaction, the solvent was evaporated under reduced pressure, and the residue was reprecipitated from ethanol to give the trimer Boc-(isoGln(5'U))$_3$-OBzl. Yield 200 mg, 37.9%.

$^1$H-NMR (270 MHz; DMSO): δ1.36(s,9H), 1.58-1.92(m, 6H),2.14(t,3H), 2.34(t,3H), 3.74-3.94(m,7H), 3.98-4.10(m, 3H), 4.15-4.30(m,2H), 5.06(s,2H), 5.20(m,3H), 5.40(m,3H), 5.63(m,3H), 5.73(d,3H), 6.90(d,1H), 7.35(m,5H), 7.65(d, 3H), 7.98(m,3H), 8.15(m,2H), 11.35(s,3H)

(2) Production of a Trimer (Boc-(isoGln(5'U))$_3$-OH)

The Boc-(isoGln(5'U))$_3$-OBzl (200 mg) obtained as described above was dissolved in methanol, and palladium-on-carbon (10%, about 40 mg) was added. The reaction was allowed to proceed in a hydrogen atmosphere for about 2 hours, followed by reprecipitation with ether to give Boc-(isoGln(5'U))$_3$-OH. Yield 190 mg, 91%.

$^1$H-NMR (270 MHz; DMSO): δ1.36(s,9H), 1.59-1.90(m, 6H), 2.07-2.30(m,6H), 3.73-3.93(m,6H), 3.99-4.09(m,3H), 4.13-4.30(m,2H), 5.05-5.48(m,4H), 5.58-5.77(m,6H), 6.90 (d,1H), 7.61-7.71(m,3H), 7.93-8.22(m,5H), 11.35(s,3H) UV (phosphate buffer) λmax (ε) 262 nm Production Example 6

Purine Base Type (inosine)-nucleoside Derivative (1) Production of N$^4$-t-butoxycarbonyl-N$^5$- (5'-deoxy-5'-inosyl)-L-isoglutamine benzyl ester (Boc-isoGln(5'I)-OBzl)

N-t-Butoxycarbonyl-L-glutamine γ-benzyl ester (Boc-L-Glu(OBzl)) (1.32 g, 3.9 mmol), HOBt (526 mg, 1 eq) and the BOP reagent (1.747 g, 1 eq) were dissolved in distilled DMF at 0° C., and the mixture was stirred for about 1 hour until returning to room temperature. DIEA (613 mg, 1 eq) was added to this solution, the 5'-amino-5'-deoxyinosine (1.04 g, 1 eq) prepared in Reference Example 3 was then added, and the mixture was stirred at room temperature for about 2 hours. The solvent was evaporated under reduced pressure and the residue was purified by silica gel column chromatography (MeOH:CHCl$_3$=1:9) to give Boc-isoGln(5'I)-OBzl. Yield 1.56 g, 68%.

$^1$H-NMR (270 MHz; DMSO): δ1.33(s,9H), 1.82(m,8H), 2.35(t,2H),3.38(m,2H), 3.97(m,3H), 4.54(q,1H), 5.05(s,1H), 5.31(d,1H), 5.48(d,1H), 5.83(d,1H), 6.96(d,1H), 7.34(m, 5H), 8.07(t,1H), 8.12(s,1H), 8.30(s,1H): IR (KBr) n 1610, 1695 cm$^{-1}$: MS (FAB) m/z 587 (M$^+$, 39.4): UV (phosphate buffer) λmax (ε) 258 nm (2) Production of N$^α$-t-butoxycarbonyl-N$^5$-(5'-deoxy-5'-inosyl)-L-isoglutamine (Boc-isoGln(5'I)-OH)

The Boc-isoGln(5'I)-OBzl (1.09 g, 1.86 mmol) obtained as described above under (1) was dissolved in methanol, palladium-on-carbon (about 40 mg) was added, and the reaction was allowed to proceed in a hydrogen atmosphere for about 2 hours to give Boc-isoGln(5'I)-OH. Yield 900 mg, 97.5%.

$^1$H-NMR (270 MHz; DMSO): δ1.33(s,9H), 1.82(m,8H), 2.35(t,2H),3.38(m,2H), 3.97(m,3H), 4.54(q,1H), 5.31(d,1H), 5.48(d,1H), 5.83(d,1H), 6.96(d,1H), 8.07(t,1H), 8.12(s,1H), 8.30(s,1H) UV (phosphate buffer) λmax(ε) 249 nm (3) Production of N$^5$-(5'-deoxy-5'-inosyl)-L-isoglutamine benzyl ester trifluoroacetate (TFA.isoGln(5'I)-OBzl)

The Boc-isoGln(5'I)-OBzl (1.01 g, 1.72 mmol) obtained as described above under (1) was dissolved in TFA, and the reaction was allowed to proceed at 0° C. for 2 hours. The TFA was then distilled off under reduced pressure, and ether was added to the residue to give TFA.isoGln(5'I)-OBzl. Yield 1.03 mg, 99%.

$^1$H-NMR (270 MHz; DMSO): δ1.97(dd,2H), 2.43(t,2H), 3.38(m,2H), 3.81(m,3H), 4.11(q,4H), 4.54(q,1H), 5.08(s, 2H), 5.31(d,1H), 5.48(d,1H), 5.83(d,1H), 6.96(d,1H), 7.36 (m,5H), 8.07(t,1H), 8.12(s,1H), 8.30(s,1H)

(4) Production of a Dimer (Boc-(isoGln(5'I))$_2$-OBzl)

The Boc-isoGln(5'I)-OH (182 mg, 0.37 mmol) obtained as described above under (2), HOBt (50 mg, 1 eq) and the BOP reagent (162 mg, 1 eq) were dissolved in distilled DMF at 0° C., and the mixture was stirred for about 1 hour until returning to room temperature. Diisopropylethylamine (DIEA) (115 mg, 2 eq) was added to this solution, the TFA.isoGln(5'I)-OBzl (220 mg, 1 eq) prepared in (3) was then added, and the mixture was stirred at room temperature for about 2 hours. After reaction, the solvent was distilled off under reduced pressure, and the residue obtained was purified by column chromatography (mobile phase: MeOH:AtOEc=1:2) to give the dimer Boc-(isoGln(5'I))$_2$-OBzl (yield 320 mg, 78%).

$^1$H-NMR (270 MHz; DMSO): δ1.31(s,9H), 1.59-1.97(m, 4H),2.15(t,2H), 2.33(t,2H), 3.82-4.05(m,2H), 4.21-4.32(q, 1H), 4.56(t,2H), 5.03(d,1H), 5.50 (bloaded-s,1H),5.82(d, 2H), 6.93(d,1H), 7.33(m,5H), 7.97-8.23(m,7H) UV (phosphate buffer) λmax (ε) 248 nm (5) Production of a Dimer (Boc-(isoGln(5'I))$_2$-OH)

The Boc-(isoGln(5'I))$_2$-OBzl (320 mg) obtained as described above under (4) was dissolved in methanol, and palladium-on-carbon (10%, about 40 mg) was added. The reaction was allowed to proceed in a hydrogen atmosphere for about 2 hours to give Boc-(isoGln(5'I))$_2$-OH (yield 298 mg, 88%).

$^1$H-NMR (270 MHz; DMSO): δ1.31(s,9H), 1.59-1.97(m, 4H),2.15(t,2H), 2.33(t,2H), 3.82-4.05(m,2H), 4.21-4.32(q, 1H), 4.56(t,2H), 5.50(bloaded-s, 1H), 5.82(d,2H),6.93(d, 1H), 7.97-8.23(m,7H); UV (phosphate buffer) λmax (ε) 248 nm Production Example 7

Pyrimidine-purine Mixed Sequence-containing PRNAs (1)

(1) Production of a Dimer (Boc-isoGln(5'U)-isoGln(5'I)-OBzl)

The Boc-isoGln(5'U)-OH (compound 6) (945 mg, 2.0 mmol) obtained in Example 2 (2), HOBt (270 mg, 1 eq) and the BOP reagent (890 mg, 1 eq) were dissolved in distilled DMF at 0° C., and the mixture was stirred for about 1 hour until returning to room temperature. Diisopropylethylamine (DIEA) (0.74 mg, 2 eq) was added to this solution, the TFA.isoGln(5'I)-OBzl (1.32 g, 1 eq) prepared in Example 6 (3) was then added, and the mixture was stirred at room temperature for about 2 hours. After reaction, the solvent was distilled off under reduced pressure, and the residue obtained was purified by silica gel column chromatography (mobile phase: MeOH: AtOEc=1:9) to give Boc-isoGln(5'U)-isoGln(5'I)-OBzl (yield 1.86 g, 97.2%).

$^1$H-NMR (270 MHz; DMSO): δ1.35(s,9H), 1.79(m,4H), 2.15(m,2H), 2.33(t,2H), 3.76-4.13(m,7H), 4.27(q,1H), 4.55 (q,1H), 5.04(s,2H), 5.17(d,1H), 5.39(d,1H), 5.51(d,1H), 5.61 (d,1H), 5.73(d,1H), 5.83(d,1H), 6.87(d,1H), 73.4(m,5H), 7.64(d,1H), 7.91-8.05(m,2), 8.11(s,1H), 8.31(s,1H); MS(FAB) m/z 941 (M$^+$, 12.1)

(2) Production of a Dimer (Boc-isoGln(5'U)-isoGln(5'I)-OH)

The Boc-isoGln(5'U)-isoGln(5'I)-OBzl (527 mg, 0.56 mmol) prepared as described above under (1) was dissolved in methanol, and palladium-on-carbon (10%, about 40 mg) was added. The reaction was allowed to proceed in a hydrogen atmosphere for about 2 hours to give Boc-isoGln(5'U)-isoGln(5'I)-OH (yield 466 mg, 98%).

$^1$H-NMR (270 MHz; DMSO): δ1.36(s,9H), 1.58-1.91(m, 4H), 2.05-2.27(m,4H), 3.74-4.07(m,6H), 4.24(q,1H), 4.55(t, 1H), 5.08-5.59(m,3H), 5.64(d,1H), 5.73(d,1H), 5.83(d,1H), 6.88(d,1H), 7.65(d,1H), 7.90-8.25(m,4), 8.31(s,1H),11.34(s, 1H); UV (phosphate buffer) λmax (ε) 258 nm (3) Production of a Dimer (TFA.isoGln(5'U)-isoGln(5'I)-OBzl)

The Boc-isoGln(5'U)-isoGln(5'I)-OBzl obtained as described above under (1) was dissolved in TFA, and the reaction was allowed to proceed at 0° C. for 2 hours. The TFA was then distilled off under reduced pressure, and ether was added to the residue to give TFA.isoGln(5'U)-isoGln(5'I)-OBzl. Yield 798 mg, 98%.

$^1$H-NMR (270 MHz; DMSO): δ1.97(m,2H), 2.38-2.48(m, 2H), 3.43-4.55(m,1H), 3.74-3.88(m,3H), 4.11(q,1H), 5.08(s, 2H), 5.27(d,1H), 5.49(d,1H), 5.63(d,1H), 5.75(d,1H), 7.36 (m,5H), 7.66(d,1H), 8.10(bloaded-s,3), 8.64(t,1H), 11.39(s, 1H)

(4) Production of a Tetramer (Boc-isoGln((5'U)-isoGln(5'I))$_2$-OBzl)

The Boc-isoGln(5'U)-isoGln(5'I)-OH (160 mg, 0.19 mmol) prepared as described above under (2), HOBt (25.4 mg, 1 eq) and the BOP reagent (83.3 mg, 1 eq) were dissolved in distilled DMF at 0° C., and the mixture was stirred for about 1 hour until returning to room temperature. DIEA (59.1 mg, 2 eq) was added to this solution, the TFA.isoGln(5'U)-isoGln(5'I)-OBzl (179 mg, 1 eq) prepared as described above under (3) was then added, and the mixture was stirred at room temperature for about 2 hours. After reaction, the solvent was evaporated under reduced pressure, and the residue was dissolved in methanol and reprecipitated with ether to give Boc-isoGln((5'U)-isoGln(5'I))$_2$-OBzl (yield 260 mg, 82.6%).

$^1$H-NMR (270 MHz; DMSO): δ1.35(s,9H), 1.79(m,8H), 2.15(m,4H), 2.33(t,4H), 3.76-4.13(m,14H), 4.27(q,2H), 4.55 (q,2H), 5.04(s,2H), 5.17(m,2H), 5.39(m,2H), 5.51(m,2H), 5.64(m,2H), 5.73(m,2H), 5.83(m,2H), 6.87(m,2H), 7.34(m, 5H), 7.64(d,2H), 7.91-8.05(m,4), 8.11(s,2H), 8.31(s,2H); MS (TOP) m/z 1674 (M$^+$)

(5) Production of a Tetramer (Boc-isoGln((5'U)-isoGln(5'I))$_2$-OH)

The Boc-isoGln((5'U)-isoGln(5'I))$_2$-OBzl (334 mg, 0.2 mmol) prepared as described above under (4) was dissolved in methanol, and palladium-on-carbon (10%, about 40 mg) was added. The reaction was allowed to proceed in a hydrogen atmosphere for about 2 hours to give Boc-isoGln((5'U)-isoGln(5'I))$_2$-OH (yield 288 mg, 91%).

$^1$H-NMR (270 MHz; DMSO): δ1.36(s,9H), 1.58-1.91(m, 8H),2.05-2.27(m,8H), 3.74-4.07(m,12H), 4.24(q,2H), 4.55(t, 2H), 5.08-5.59(m,6H), 5.64(d,2H), 5.73(d,2H), 5.83(d,2H), 6.88(d,2H), 7.65(d,2H), 7.90-8.25(m,8), 8.31(s,2H),11.34(s, 2H); UV (phosphate buffer) λmax(ε) 258 nm (6) Production of a Tetramer (TFA.isoGln((5'U)-isoGln(5'I))$_2$-OBzl The Boc-isoGln((5'U)-isoGln(5'I))$_2$-OBzl (334 mg, 0.2 mmol) prepared as described above under (4) was dissolved in TFA, and the reaction was allowed to proceed at 0° C. for 2 hours. The TFA was then distilled off under reduced pressure, and ether was added to the residue for reprecipitation, whereby TFA.isoGln((5'U)-isoGln(5'I))$_2$-OBzl was obtained. Yield 290 mg, 92%.

$^1$H-NMR (270 MHz; DMSO): δ1.95(m,4H), 2.38-2.50(m, 4H), 3.42-4.45(m,2H), 3.75-3.87(m,6H), 4.11-4.14(q,2H), 5.08(s,4H), 5.27(m,2H), 5.49(m,2H), 5.63(m,2H), 5.75(m, 2H), 7.36(m,5H), 7.66(d,2H), 8.10(bloaded-s,6), 8.64(t,2H), 11.39(s,2H)

(7) Production of an Octamer (Boc-isoGln((5'U)-isoGln(5'I))$_4$-OBzl)

The Boc-isoGln((5'U)-isoGln(5'I))$_2$-OH (65 mg, 4.1×10$^{-5}$ mol) prepared as described above under (5), HOBt (5.5 mg, 1 eq) and the BOP reagent (18.2 mg, 1 eq) were dissolved in distilled DMF at 0° C., and the mixture was stirred for about 1 hour until returning to room temperature. DIEA (12.9 mg, 2 eq) was added to this solution, the TFA.isoGln((5'U)-isoGln (5'I))$_2$-OBzl (69.2 mg, 1 eq) prepared as described above under (6) was then added, and the mixture was stirred at room temperature for about 2 hours. After reaction, the solvent was evaporated under reduced pressure, and the residue was dissolved in DMF, followed by reprecipitation with ethanol to give Boc-isoGln((5'U)-isoGln(5'I))$_4$-OBzl (yield 113 mg, 88.0%).

$^1$H-NMR (270 MHz; DMSO): δ1.35(s,9H), 1.57-1.96(m, 16H), 2.13(m,14H), 2.33(t,4H), 3.74-4.32(m, 28H), 4.56(m, 4H), 5.03(s,2H), 5.17(m,4H), 5.30(m,4H), 5.40(m,4H), 5.53 (m,4H), 5.63(d,2H), 5.66(d,2H), 5.72(m,4H), 5.83(m,4H), 6.89(m,1H), 7.32(m,5H), 7.59-7.70(m,5H), 7.84-8.35(m,4), 11.32(s,4H); MS (TOP) m/z 3139 (M$^+$)

Production Example 8

Pyrimidine-purine Mixed Sequence-containing PRNAs (2)

(1) Production of a Dimer (Boc-isoGln(5'I)-isoGln(5'U)-OBzl)

The Boc-isoGln(5'I)-OH (520 mg, 1.05 mmol) prepared in Example 6 (2), HOBt (142 mg, 1 eq) and the BOP reagent (465 mg, 1 eq) were dissolved in distilled DMF at 0° C., and the mixture was stirred for about 1 hour until returning to room temperature. DIEA (330 mg, 2 eq) was added to this solution, the TFA.isoGln(5'U)-OBzl (605 mg, 1 eq) prepared in Example 2 (3) was then added, and the mixture was stirred at room temperature for about 2 hours. After reaction, the solvent was evaporated under reduced pressure, and the residue obtained was purified by silica gel column chromatography (mobile phase: MeOH:AtOEc=1:9) to give Boc-isoGln (5'I)-isoGln(5'U)-OBzl (yield 652 mg, 66.0%).

$^1$H-NMR (270 MHz; DMSO): δ1.35 (s,9H), 1.79(m,4H), 2.15(m,2H), 2.33(t,2H), 3.76-4.13(m,7H), 4.27(q,1H), 4.55 (q,1H), 5.04(s,2H), 5.17(d,1H), 5.39(d,1H), 5.51(d,1H), 5.64 (d,1H), 5.73(d,1H), 5.83(d,1H), 6.87(d,1H), 7.34(m,5H), 7.64(d,1H), 7.91-8.05(m,2), 8.11(s,1H), 8.31(s,1H); MS (FAB) m/z 941 (M$^+$, 10.9)

(2) Production of a Dimer (Boc-isoGln(5'I)-isoGln(5'U)-OH)

The Boc-isoGln(5'I)-isoGln(5'U)-OBzl (527 mg, 0.56 mmol) prepared as described above was dissolved in methanol, and palladium-on-carbon (10%, about 40 mg) was added. The reaction was allowed to proceed in a hydrogen atmosphere for about 2 hours to give Boc-isoGln(5'I)-isoGln(5'U)-OH (yield 410 mg, 91%).

$^1$H-NMR (270 MHz; DMSO): δ1.36(s,9H), 1.58-1.91(m, 4H), 2.05-2.27(m,4H), 3.74-4.07(m,6H), 4.24(q,1H), 4.55(t, 1H), 5.08-5.59(m,3H), 5.64(d,1H), 5.73(d,1H), 5.83(d,1H), 6.88(d,1H), 7.65(d,1H), 7.90-8.25(m,4), 8.31(s,1H),11.34(s,1H); UV (phosphate buffer) λmax(ε) 259 nm Production Example 9

Production of a Trimer (Boc-isoGln(5'U)-isoGln(5'I)-isoGln(5'U)-OBzl)

The Boc-isoGln(5'U)-isoGln(5'I)-OH (80 mg, 0.094 mmol) prepared in Example 7 (2), HOBt (12.7 mg, 1 eq) and the BOP reagent (41.6 mg, 1 eq) were dissolved in distilled DMF at 0° C., and the mixture was stirred for about 1 hour until returning to room temperature. DIEA (30 mg, 2 eq) was added to this solution, the TFA.isoGln(5'U)-OBzl (54.2 mg, 1 eq) prepared in Example 2 (3) was then added, and the mixture was stirred at room temperature for about 2 hours. After reaction, the solvent was evaporated under reduced pressure, and the residue obtained was dissolved in DMF and reprecipitated with methanol/ether to give the trimer Boc-isoGln(5'U)-isoGln(5'I)-isoGln(5'U)-OBzl (yield 98 mg, 88.0%).

$^1$H-NMR (270 MHz; DMSO): δ1.36(s,9H), 1.60-1.95(m,8H), 2.05-2.20(m,4H), 2.33(t,2H), 3.74-4.08(m,9H), 4.22(m,2H), 4.57(q,1H), 5.05(s,2H), 5.14-5.20(m,2H), 5.29(d,1H), 5.40(m,2H),5.52(d,1H), 5.61(d,1H), 5.65(d,1H), 5.73(d,2H), 5.83(d,2H), 6.90(d,1H), 7.34(m,5H), 7.64(d,2H), 7.92-8.04(m,3H),8.09-8.24(m,3H), 8.32(s,1H), 11.35(s,1H); MS (FAB) m/z 1295 (M$^+$, 2.4)

Production Example 10

Solid Phase Synthesis of Nucleoside Derivatives (PRNA (γ Type) Oligomers)

(1) Production of an Fmoc-PRNA Monomer (γ Type)

(i) N$^α$-9-fluorenylmethoxycarbonyl-N$^5$-5'-deoxy-5'-uridinyl-L-isoglutamine benzyl ester (Fmoc-isoGln(5'U)-OBzl)

The TFA.isoGln(5'U)-OBzl (compound 7) (2.196 g, 3.81 mmol) prepared in Example 2 (3) and Fmoc-Osu (N-(9-fluorenylcarbonyloxy)succinimide) (1.537 g, 1.2 eq) were dissolved in distilled DMF at 0° C., and the solution was stirred. DIEA (1.99 g, 2 eq) was added to this solution, and the mixture was stirred at room temperature for 30 minutes. This solution was concentrated under reduced pressure, methanol was added to cause crystallization of Fmoc-isoGln(5'U)-OBzl, and the crystals were recovered. Yield 2.156 g, 82.8%.

$^1$H-NMR (270 MHz; DMSO): δ1.86(m,2H), 2.37(t,2H), 3.83(m,2H), 4.03(m,3H), 4.16-4.31(m,3H), 5.07(s,2H), 5.22(d,1H), 5.44(d,1H), 5.61(d,1H), 5.74(d,2H), 7.26-7.44(m,9H), 7.55-7.76(d,4H), 7.88(d,2H), 8.14(t,3H), 11.34(s,1H)

(ii) N$^α$-9-Fluorenylmethoxycarbonyl-N$^5$-5'-deoxy-5'-uridinyl-L-isoglutamine (Fmoc-isoGln(5'U)-OH)

The Fmoc-isoGln(5'U)-OBzl (2.156 g, 3.15 mmol) obtained as described above under (i) was dissolved in methanol/DMF (1:1), and palladium-on-carbon (10%, about 40 mg) was added. The reaction was allowed to proceed in a hydrogen atmosphere for about 20 minutes to give Fmoc-isoGln(5'U)-OH. This was further purified by reprecipitation with ether. Yield 2.08 g, 99%.

$^1$H-NMR (270 MHz; DMSO): δ1.86(m,2H), 2.37(t,2H), 3.83(m,2H), 4.03(m,2H), 4.16-4.31(m,2H), 5.22(d,1H), 5.44(d,1H), 5.61(d,1H), 5.74(d,2H), 7.26-7.44(m,4H), 7.54-7.77(d,4H), 7.88(d,2H), 8.15(t,3H), 11.35(s,1H)

(iii) N$^α$-9-Fluorenylmethoxyarbonyl-N$^5$-deoxy-5'-inosinyl-L-isoglutamine benzyl ester (Fmoc-isoGln(5'I)-OBzl)

The TFA.isoGln(5'I)-OBzl (910 mg, 1.51 mmol) prepared in Example 6 (3) and Fmoc-Osu (611 mg, 1.2 eq) were dissolved in distilled DMF at 0° C., and the solution was stirred. DIEA (475 mg, 2 eq) was added to this solution, and the mixture was stirred at room temperature for 2 hours. This solution was concentrated under reduced pressure, and the residue was purified by silica gel column chromatography (MeOH:CHCl$_3$=1:9). Yield 943.8 mg, 87.7%.

$^1$H-NMR (270 MHz; DMSO): δ1.72-2.01(m,2H), 2.15(t,2H), 2.37(t,2H), 3.25-3.52(m,6H), 3.91-4.09(m,3H), 4.55(q,1H), 5.06(s,2H), 5.35(d,1H), 5.53(d,1H), 5.84(d,1H), 7.25-7.44(m,9H), 7.63(d,1H), 7.72(t,2H), 7.88(d,2H), 8.10(s,1H), 8.20(t,1H), 8.33(s,1H)

(iv) N$^α$-9-Fluorenylmethoxycarbonyl-N$^5$-5'-deoxy-5'-inosinyl-L-isoglutamine (Fmoc-isoGln(5'I)-OH)

The Fmoc-isoGln(5'I)-OBzl (943.8 mg, 1.32 mmol) obtained as described above under (iii) was dissolved in methanol/DMF (1:1), and palladium-on-carbon (10%, about 40 mg) was added. The reaction was allowed to proceed in a hydrogen atmosphere for about 2 hours to give Fmoc-isoGln(5'I)-OH. This was further purified by reprecipitation from ether. Yield 880 mg, 93.2%.

$^1$H-NMR (270 MHz; DMSO): δ1.65-1.96(m,2H), 2.23(t,2H), 3.32-3.50(m,3H), 3.90-4.08(m,3H), 4.15-4.30(m,3H), 4.55(t,1H), 5.83(d,1H), 7.26-7.46(m,4H), 7.64(d,1H), 7.68-7.78(m,2H), 7.88(d,2H), 8.10(s,1H), 8.20(t,1H), 8.33(s,1H)

(2) Production of PRNA Oligomers (FIG. 1)

PRNA oligomers were produced according to the scheme shown in FIG. 1. The solid phase support resin used was NovaSyn (registered trademark) TGR-Resin (product of Pharmacia) having a polyethylene glycol chain as a spacer.

① Preparation of the Solid Phase Support Resin

First, the solid phase support resin with the amino group protected with an Fmoc group was thoroughly swelled with N-methylpyrrolidone (NMP) and, then, the protective group Fmoc was eliminated from the solid phase support resin by reacting with 20% piperidine (PPD)/NMP for 15 minutes. The mixture was stirred on a vortex at 5-minute intervals and, after completion of the reaction, the resin was washed with 5 portions of NMP.

② PRNA Extension Reaction

The PRNA extension reaction was carried out by successive condensation of Fmoc-PRNAs having an Fmoc protective group at the N terminus and a free C terminus by repeating the following reaction.

<Condensation Reaction>

An Fmoc-PRNA (3 eq relative to the resin), 2-(1H-benzotriazol-1-yl)-1,1,3,3-tetramethyluronium hexafluorophosphate (HBTU) (3 eq) and 1-hydroxybenzotriazole (HOBt) (3 eq) were dissolved in NMP, the solution was introduced into a column packed with the above resin, diisopropylethylamine (DIEA) (6 eq) was added, and the reaction was allowed to proceed for 20 minutes with stirring on a vortex at 5-minute intervals. After completion of the reaction, the resin was washed with 5 portions of NMP.

<Reaction Confirmation Test>

The coupling or non-coupling of the Fmoc-PRNA monomer was confirmed by the Kayser test (100° C., 2 minutes) using the ninhydrin reagent capable of reacting with a free amino group. When the test was found positive (when the unreacted amino group was found remaining), the above condensation reaction was again carried out and, if necessary, repeated until completion of the reaction.

The above condensation reaction and reaction confirmation test were conducted alternately to thereby cause the desired Fmoc-PRNA monomers to be involved in the chain extension one by one to synthesize the desired PRNA oligomer on the solid phase support resin.

③ Isolation and Purification of the Synthetic PRNA Oligomer from the Resin

After synthesis, the N terminus of the PRNA oligomer was deprotected by treatment with 20% PPD/NMP, and the resin was washed with 5 portions of NMP. After further washing with 5 portions of chloroform, the resin was dried under vacuum. Then, the synthetic PRNA oligomer was excised from the resin using TFA containing 5% of water as a scavenger. The TFA was distilled off using an evaporator. While the TFA solution was passed through a column, cold ether was added to precipitate a white solid. This was separated by centrifugation, the supernatant was removed by decantation, and the residue was dried under vacuum to give the PRNA oligomer in a crude form. The crude product was subjected to analytical HPLC under the conditions specified below for confirmation of its giving a single peak, followed by MALDI-TOF for molecular weight determination. Further, the crude product was applied to a preparative column, the desired fraction was recovered, the thus-obtained fraction solution was lyophilized to give a white solid.

<HPLC Conditions>

Analytical column: Nakalai COSMOSIL 4.6×150 mm Type waters, 1 mL/min Preparative column: Nakalai COSMOSIL 10×250 mm Type waters, 3 mL/min Eluent Solution A: 0.1% TFA/water Eluent Solution B: 0.08% TFA/acetonitrile Mobile phase: Adjusted so that the solutions A:solution B ratio might change from 100:0 to 0:100 in 30 minutes. Detection: UV detection at the wavelength 260 nm (2-1) PRNA Oligomer Production (i) The initial coupling reaction onto the solid phase support resin was carried out using lysine with the N terminus protected by a 9-fluorenylmethoxycarbonyl group and the C terminus protected by a benzyl ester group (Fmoc-Lys(OBzl)-OH) as the above-mentioned Fmoc-PRNA monomer, and the subsequent condensation reactions were carried out using the Fmoc-isoGln(5'U)-OH and Fmoc-isoGln(5'I)-OH prepared in Production Example 10 (1) (ii) and (iv), respectively to synthesize the following octamer PRNA.

① NH$_2$-Lys-isoGln(5'U)-isoGln(5'U)-isoGln(5'U)-isoGln(5'U)-isoGln(5'U)-isoGln(5'I)-isoGln(5'I)-isoGln(5'U)-OH (PRNA Oligomer 1). Yield 88%, TOF-MS m/z =3021.8 (M$^+$)

Figure 35:
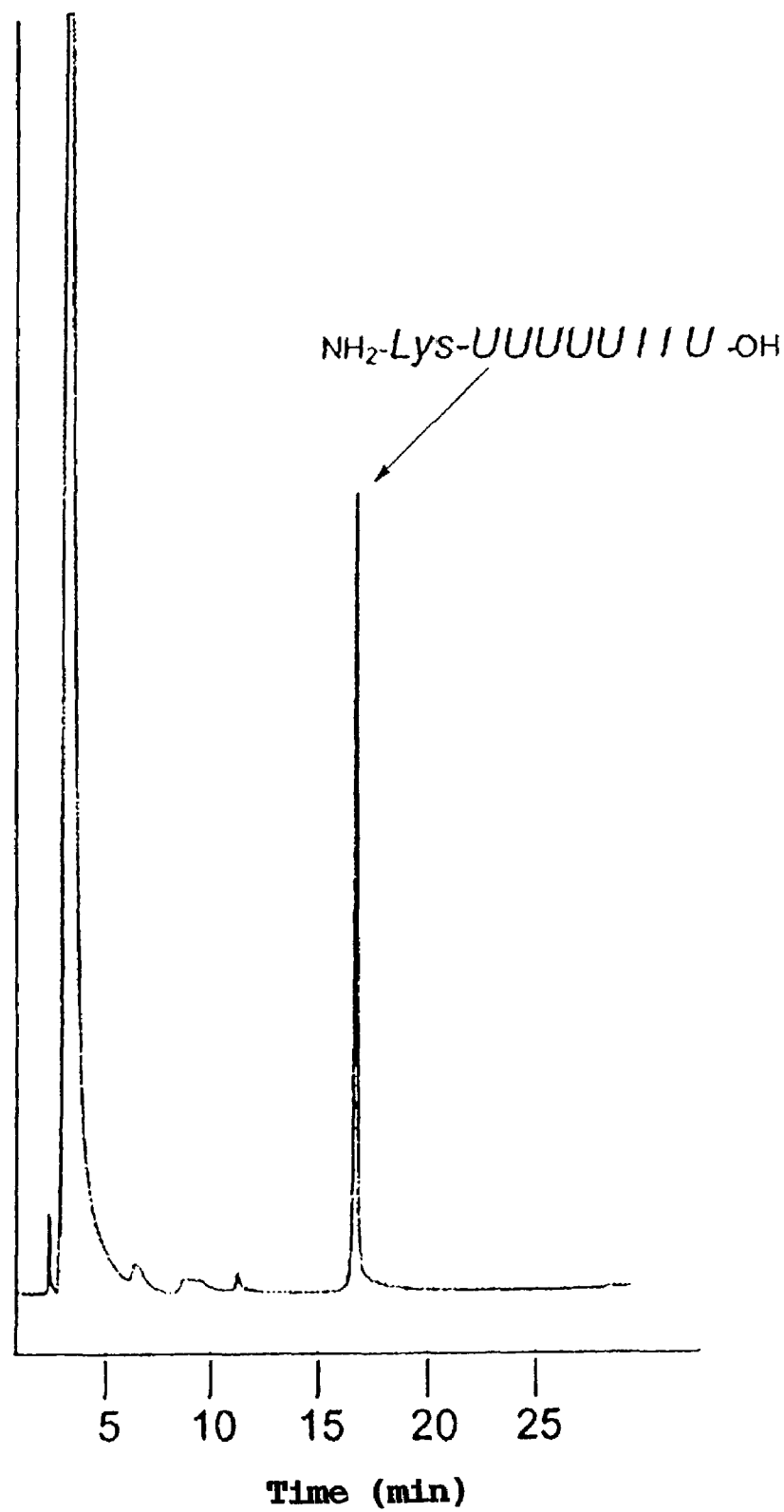
FIG. 35 is a chromatogram showing the results of HPLC analysis of the PRNA oligomer 1 produced (synthesized on a solid phase) in Production Example 10.

The results of HPLC analysis are shown in FIG. 35.

(ii) The condensation/extension reaction was repeated using the above Fmoc-isoGln(5'U)-OH and Fmoc-isoGln(5'I)-OH as the above-mentioned Fmoc-PRNA monomers, and the final condensation reaction was carried out using Fmoc-Lys(OBzl)-OH. The following two octamer PRNAs were thus synthesized.

NH$_2$-isoGln(5'U)-isoGln(5'I)-isoGln(5'I)-isoGln(5'U)-isoGln(5'U)-isoGln(5'U)-isoGln(5'U)-isoGln(5'U)-Lys-OH (PRNA oligomer 2), yield 80%, TOF-MS m/z=3021.8(M$^+$)

NH$_2$-isoGln(5'I)-isoGln(5'I)-isoGln(5'I)-isoGln(5'I)-isoGln(5'I)-isoGln(5'I)-isoGln(5'I)-isoGln(5'I)-Lys-OH (PRNA oligomer 3), yield 85%, TOF-MS m/z=3165.9 (M$^+$)

Production Example 11

Production of a Chimeric Molecule Dimer (PRNA(Urd)-DNA(Thd))

A chimeric nucleic acid (PRNA(Urd)-DNA(Thd) dimer) was synthesized according to the following scheme using a PRNA having uracil as a base and a DNA having thymine as a base.

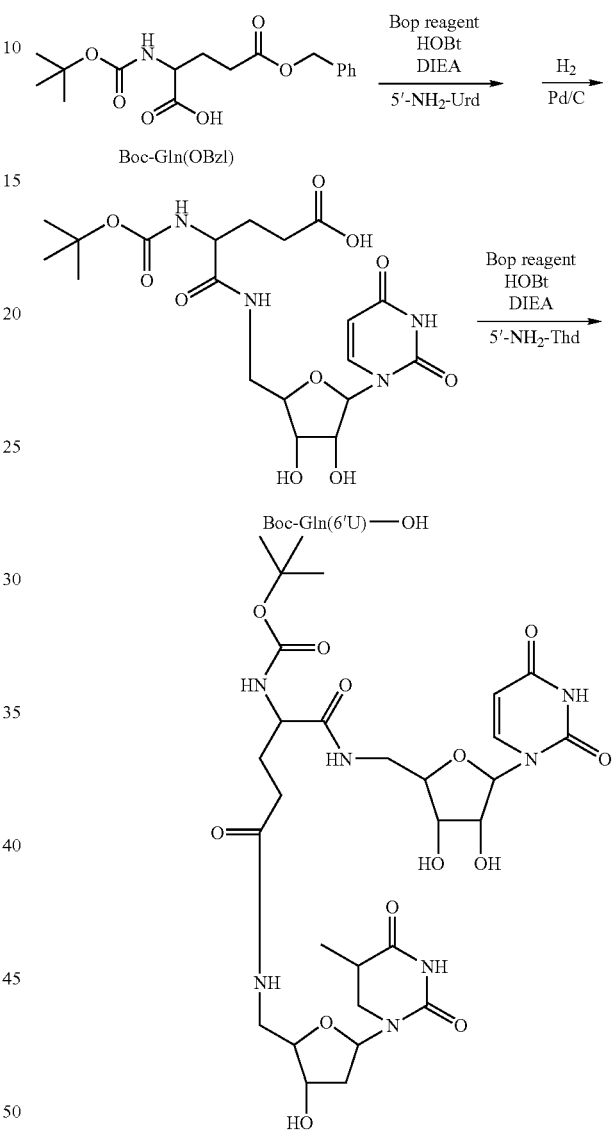

Boc-isoGln(5'U)-OH was synthesized (yield 88%) by introducing 5'-NH$_2$-Urd (Reference Example 1) into the α-carboxyl group of N$^4$-t-butoxycarboyl-N$^5$-(5'-deoxy-5'-uridyl)-L-isoglutamine benzyl ester (Boc-isoGln(OBzl)) with use of BOP reagent and HOBt according to the method of Example 2 (1) and, then, deprotecting the γ-carboxyl group in the manner of catalytic reduction according to Example 2 (2). Then, Boc-isoGln(5'U)-OH (326 mg, 0.5 mmol), HOBt (67.5 mg, 1 eq) and the BOP reagent (222 mg, 1 eq) were dissolved in distilled DMF at 0° C., and the solution was stirred for about 1 hour until returning to room temperature. Diisopropylethylamine (DIEA) (97 mg, 1.5 eq) was added to this solution. The 5'-NH$_2$-Thd (424 mg, 1.05 eq) prepared in Reference Example 4 was added, and the mixture was stirred at room temperature for about 3 hours. After confirmation of completion of the reaction by TLC, the reaction was quenched with methanol. This solution was concentrated under reduced pressure, 5 ml of methanol was added, and ether was added to the solution for causing reprecipitation, whereby the title compound PRNA(Urd)-DNA(Thd) was obtained. Yield 332 mg, 95%.

$^1$H-NMR (270 MHz; DMSO): δ1.59-1.91(m,5H), 1.98-2.21(m,4H), 3.12-3.54(m,4H), 3.65-4.16(m,6H), 5.18(d, J=4.9,1H), 5.29(d,J=3.9,1H), 5.40(d,J=5.4 Hz,1H), 5.64(d, J=8.3 Hz,1H), 5.73(d,J=5.9 Hz,1H), 6.13(t,J=1H), 6.89(d, J=8.3,1H), 7.50(s,1H), 7.64(d,J=7.8 Hz, 1H), 7.90-8.04(m, 2H), 11.30(s,2H) 7.50

Production Example 12

Production of a Chimeric Molecule Dodecamer (PRNA(Urd)$_8$-DNA(Thd)$_4$)

(1) 5'-O-(4,4'-Dimethoxytrityl)thymidine (5'-DMTr-Thd)

Thymidine (1.918 g, 8.0 mmol) was dried under reduced pressure for a while, pyridine was then added in an argon atmosphere, and the mixture was stirred. 4,4'-Dimethoxytrityl chloride (DMTr-Cl) was added at 0° C., and the mixture was allowed to return to room temperature over about 2 hours with stirring. After confirmation of completion of the reaction by TLC, the reaction was quenched with water. This solution was concentrated under reduced pressure, the concentrate was dissolved in dichloromethane, and the solution was washed with a saturated aqueous solution of copper sulfate and with brine. The organic layer was evaporated under reduced pressure, and the residue was purified by silica gel chromatography (MeOH:CH$_2$Cl$_2$=1:9). The eluate fraction was evaporated under reduced pressure, and the residue was dissolved in a small amount of ethyl acetate. Hexane was added to this solution for reprecipitation to give the title compound 5'-DMTr-Thd. Yield 3.67 g, 82.7%.

$^1$H-NMR (270 MHz; DMSO): δ1.44(s,3H), 2.07-2.32(m, 2H), 3.09-3.26(m,2H), 3.73(s,6H), 3.91-3.83(m,1H), 4.25-4.36(m,1H), 5.34(d,J=4.4 Hz,1H), 6.20(t,J=6.84 Hz,1H), 6.89(d,J=8.3 Hz,4H), 7.17-7.42(m,9H), 7.51(s,1H), 11.35(s, 1H)

(2) 5'-O-(4,4'-Dimethoxytrityl)thymidine 3'-(cyanoethyl N,N-diisopropylphosphoramidite) (5'-DMTr-3'-CEDIPA-Thd)

The 5'-DMTr-Thd (136 mg, 0.25 mmol) prepared as described above under (1) was dried under reduced pressure for a while, dichloromethane was added in an argon atmosphere, and the mixture was stirred. DIPA (17 mg, 0.5 eq) and tetrazole (9 mg, 0.5 eq) were added to this solution and, after dissolution, cyanoethyl N,N'-bis(diisopropyl)phosphorodiamidite (83 mg, 1.1 eq) was added, and the mixture was stirred at room temperature for 3 hours. After confirmation of completion of the reaction by TLC, the reaction was quenched with methanol. This solution was evaporated under reduced pressure, the residue was dissolved in dichloromethane, and the solution was washed with a 5% aqueous solution of sodium hydrogen carbonate and with brine. This organic phase was evaporated under reduced pressure, and the residue was purified by silica gel chromatography (MeOH:CH$_2$Cl$_2$=1:20). The eluate fraction was evaporated under reduced pressure, the residue was dissolved in 5 ml of dichloromethane, and hexane was added to the solution for reprecipitation, whereby 5'-DMTr-3'-CEDIPDA-Thd was obtained. The formation of said compound was confirmed by the occurrence of the base moiety 5-position methyl group, of the sugar moiety 1' hydrogen and of the DMTr group and by the agreeing Rf value. Yield 61.2 mg, 32.2%. Rf (ETOH:CH$_2$Cl$_2$:(Et)$_3$N=50:45:5) 0.49, 0.53

(3) 5'-N-(4,4'-Dimethoxytrityl)-5'-amino-5'-deoxythymidine (5'-DMTr-NH-Thd)

The 5'-amino-5'-deoxythymidine (5'-NH$_2$-Thd) (241 mg, 1.0 mmol) prepared in Reference Production Example 4 was dried under reduced pressure for a while and, in an argon atmosphere, pyridine was added, and the mixture was stirred. Thereto was added, at 0° C., 4,4'-dimethoxytrityl chloride (DMTr-Cl) (423.25 mg, 1.25 eq), and the mixture was stirred for about 2 hours while allowing the same to return to room temperature. After confirmation of completion of the reaction by TLC, the reaction was quenched with water. This solution was concentrated under reduced pressure, the residue was dissolved in dichloromethane, and the solution was washed with a saturated aqueous solution of copper sulfate and with brine. This organic phase was evaporated under reduced pressure, and the residue was purified by silica gel chromatography (MeOH;CH$_2$Cl$_2$=1:9). The eluate fraction was evaporated under reduced pressure, and the residue was dissolved in a small amount of ethyl acetate. Hexane was added to this solution for reprecipitation to give the title compound 5'-DMTr-NH-Thd. The formation of said compound was confirmed by the occurrence of the base moiety position 5 methyl group, the sugar moiety position 1' hydrogen and the DMTr group, and through the proton ratio. Yield 203 mg, 37.3%.

(4) 5'-N-(4,4'-Dimethoxytrityl)-5'-amino-5'-deoxythymidine-3'-(cyanoethyl N,N-diisopropylphosphoramidite) (5'-DMTr-NH-3'-CEDIPA-Thd)

The 5'-DMTr-NH-Thd prepared in (3) (393 mg, 0.72 mmol) was dried under reduced pressure for a while and, in an argon atmosphere, dichloromethane was added, and the mixture was stirred. To this solution was added DIEA (187 mg, 2.0 eq) and, after dissolution, cyanoethyl N,N'-diisopropyl chlorophosphorodiamidite (188 mg, 1.1 eq) was added, and the mixture was stirred at room temperature for 3 hours. After confirmation of completion of the reaction by TLC, the reaction was quenched with methanol. This solution was evaporated under reduced pressure, the residue was dissolved in dichloromethane, and the solution was washed with a 5% aqueous solution of sodium hydrogen carbonate and with brine. This organic phase was evaporated under reduced pressure, and the residue was purified by silica gel chromatography (MeOH:CH$_2$Cl$_2$=1:20). The eluate fraction was evaporated under reduced pressure, and the residue was dissolved in 5 ml of dichloromethane. Hexane was added to this solution for reprecipitation to give the title compound 5'-DMTr-NH-3'-CEDIPA-Thd. The formation of said compound was confirmed based on the NMR and Rf data. Yield 293 mg, 54.6%; Rf (EtOH:CH$_2$Cl$_2$:(Et)$_3$N=50:45:5) 0.49, 0.53

(5) Production of a Chimeric Molecule (PRNA(Urd)$_8$-DNA (Thd)$_4$)

A chimeric molecule (PRNA(Urd)$_8$-DNA(Thd)$_4$) was synthesized according to the following scheme.

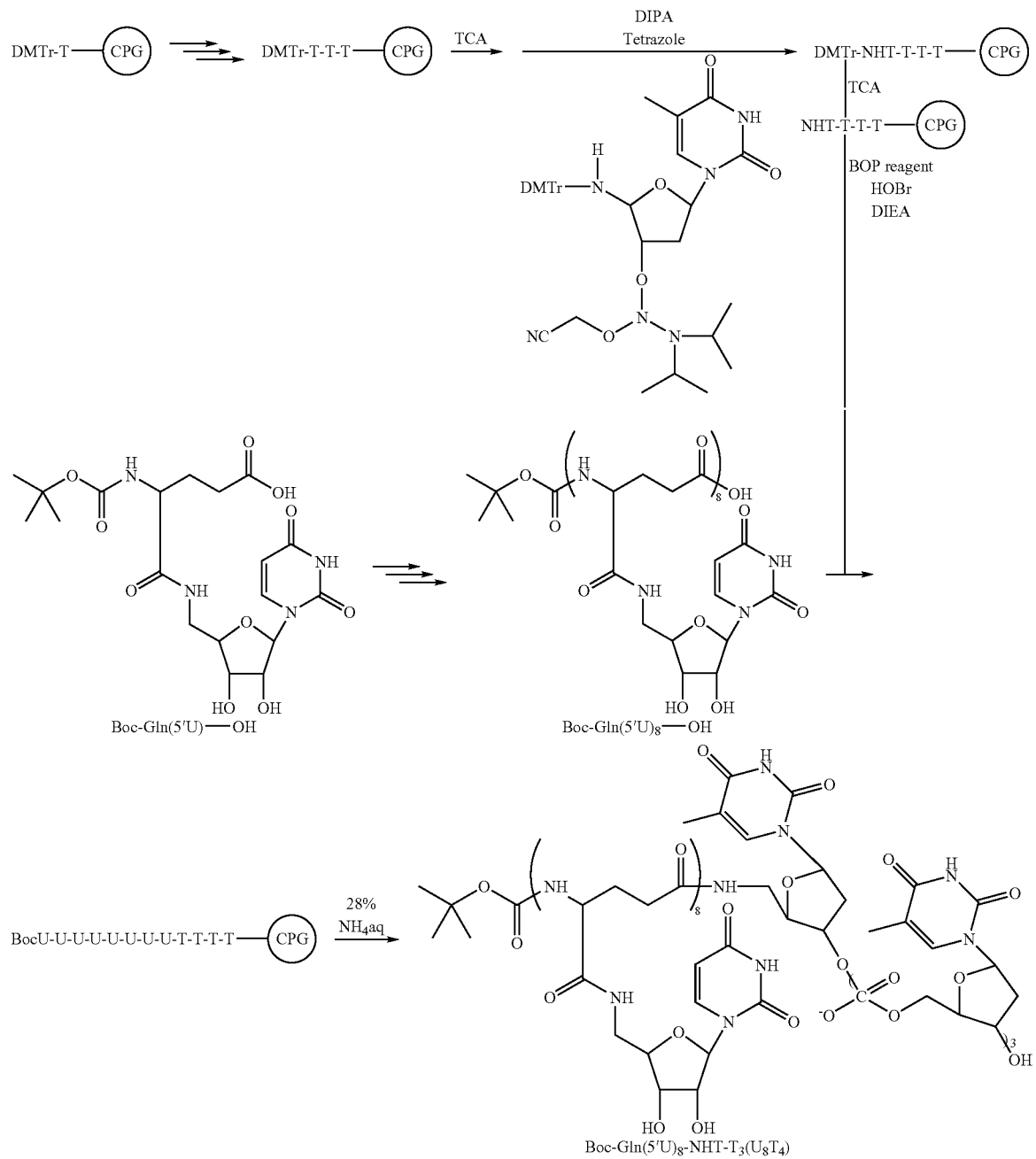

(i) Solid Phase Synthesis of a DNA Oligomer

First, the 5'-hydroxyl group of thymidine was protected with a 4,4'-dimethoxytrityl chloride (DMTr-Cl) group by the method described above under (1) to give 5'-DMTr-Thd, which was then reacted with cyanoethyl N,N'-bis(diisopropyl)chlorophosphorodiamidite (CEDIPA) in the presence of DIPA and tetrazole, as described above under (2), to give an 3'-amidite derivative of thymidine (5'-DMTr-3'-CEDIPA-Thd). Using a CPG (controlled pored glass) as a solid phase support and while activating with DIPA and tetrazole, the above 3'-amidite derivative of thymidine (5'-DMTr-3'-CEDIPA-Thd) was successively introduced onto the solid phase to extend thymidine on the solid phase to give a trimer. Then, the amino-terminal DMTr-Cl group was eliminated using TCA, and the thymidine trimer formed on the solid phase was condensed with the 3'-amidite derivative of 5'-aminothymidine (5'-DMTr-NH-3'-CEDIPA-Thd) synthesized as described above under (3) and (4) by activating with DIPA and tetrazole, followed again by deprotection with TCA. Thus, a thymidine tetramer having an amino group at the 5' terminus was synthesized.

(ii) Liquid Phase Synthesis of a PRNA Oligomer

A PRNA(Urd) octamer (Boc-isoGln(5'U)$_8$-OH) was produced by the method of Example 2 (11) (compound 15).

(iii) DNA Oligomer-PRNA Oligomer Condensation Reaction

The PRNA(Urd) octamer prepared as described above (Boc-isoGln(5'U)$_8$-OH) (73.8 mg, 3 eq), the BOP reagent (11.1 mg, 3 eq) and HOBt (3.4 mg, 3 eq) were dissolved in DMF (1.5 ml), and the solution was applied to the solid phase carrying the thymidine tetramer. DIEA (2.1 mg, 3.3 eq) was added, in 5 divided portions, to the solid phase, and the treated solid phase was allowed to stand for 3 minutes. After 5 repetitions of this procedure, the solid phase was washed with 7 ml of DMF and further with 7 ml of dichloromethane. Then, 0.5 ml of 28% ammonia water was added to the solid phase and the whole was allowed to stand for 15 minutes to excise the condensate from the solid phase. Thus, a chimeric molecule dodecamer ((PRNA(U)$_8$-DNA(T)$_4$) was obtained. Yield about 50%; m/z (TOP) 4131 (M+2Na)$^{2+}$.

INDUSTRIAL APPLICABILITY

The antisense molecule of the invention is characterized in that the orientation of all or a part of the base moieties contained in said molecule can be changed from anti to syn or from syn to anti in an on/off manner (with reversible) by the presence or absence of an external factor, such as "borates", an alkaline earth metal or a transition metal, or under the influence of the concentration thereof, and/or under the influence of a sugar, pH, light or temperature for instance. Therefore, the binding of the antisense molecule of the invention to a desired mRNA/gene (base sequence) can be controlled (binding/dissociation) by regulating the condition(s) of such external factor(s). Thus, the antisense molecule of the invention can be regarded as an antisense molecule based on a novel conception, which can reversibly control the expression of a gene function in an on-off (expression and inhibition) manner in the antisense method.

In the prior art antisense method, the expression of a gene function can be controlled only in the direction of inhibition by off control and, therefore, the prior method can be applied only to the gene therapy intended to cause cells deaths and/or loss of a function(s) of a cancer gene or hereditary disease-related gene.

On the contrary, in accordance with the invention, the antisense function of the antisense molecule can be arbitrarily controlled in both the directions of on and off (with reversible) by the synergic action of the above-mentioned external factor (orientation controlling factor—orientation regulating factor/orientation regulation controlling factor—), so that said molecule can be positively utilized for maintaining an appropriate level of a cell function(s) by striving not only for the conventional inhibitory control (negative control) but for promoting control (positive control). Thus, the method of reversible controlling the gene expression according to the invention is a very useful and promising method in the gene therapy as a more diversified method of gene control as compared with the prior art inhibitory control.

The invention claimed is:

1. An antisense molecule comprising:
a nucleic acid selected from the group consisting of DNA, RNA, and derivatives thereof; and
a molecule coupled to said nucleic acid and selected from the group consisting of monomeric or polymeric mono-, oligo-, or polyamino acids-nucleosides represented by the general formula (3):

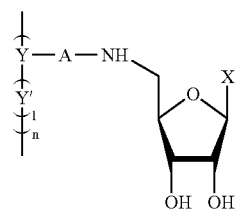

wherein each X is the same or different and represents a pyrimidine or purine base or a derivative thereof; each Y and Y' is the same or different and represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylomithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond or a carbonyl or thiocarbonyl group, l is an integer of 0 to 5, and n is an integer of 1 to 100.

2. An antisense composition which comprises an antisense molecule as defined in claim 1 and an orientation regulating factor.

3. The antisense composition according to claim 2, wherein the orientation regulating factor comprises at least one member selected from the group consisting of borates, alkaline earth metals and transition metals.

4. The antisense molecule according to claim 1, wherein said amino acid or amino acid derivative can be represented by the formula (ii):

wherein m is an integer of 1 to 3, $R^5$ is an oxygen or sulfur atom and * indicates the site of bonding to A in general formula (3).

5. The antisense molecule according to claim 1, wherein, in general formula (3), Y is represented by the formula (iii):

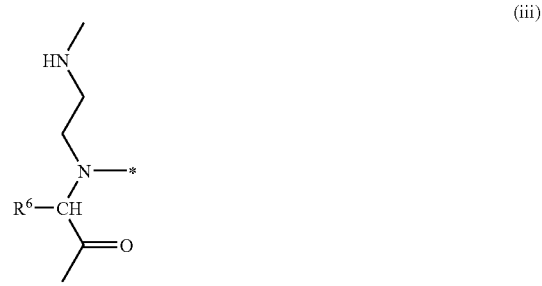

wherein $R^6$ is a hydrogen atom or a carboxymethyl, carboxyethyl, hydroxymethyl, aminobutyl, aminopropyl or 4-amino-3-hydroxypropyl group and * indicates the site of bonding to A in general formula (3).

6. An antisense molecule represented by the general formula (3):

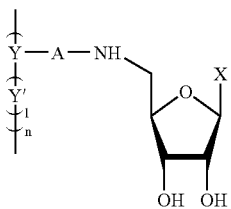

(3)

wherein X is (are) the same or different and each represents a pyrimidine or purine base or a derivative thereof, Y' represents at least one amino acid or amino acid derivative selected from the group consisting of serine, threonine, ornithine, aspartic acid, glutamic acid, lysine, arginine, cysteine, methionine, δ-hydroxylysine, N-aminoethylglycine, N-aminoethylserine, N-aminoethyllysine, N-aminoethylornithine, N-aminoethylaspartic acid, N-aminoethylglutamic acid, homoglutamic acid, β-thiocarbonylaspartic acid, γ-thiocarbonylglutamic acid, and δ-thiocarbonylhomoglutamic acid, A represents a single bond, l is an integer of 0 to 5, n is an integer of 1 to 100, and Y is a group represented by the formula (i):

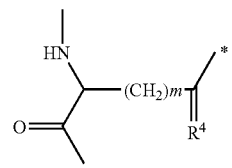

(i)

(in which m is an integer of 1 to 3, $R^4$ is an oxygen or sulfur atom and * indicates the site of bonding to A in general formula (3))

and intended for use in its binding to a mRNA/gene and/or departure from the mRNA/gene by controlling the orientation of the pyrimidine or purine base relative to the sugar in said molecule by an orientation controlling factor.

7. The antisense molecule of claim 1, wherein the molecule coupled to said nucleic acid is monomeric and n is 1.

8. The antisense molecule of claim 1, wherein the molecule coupled to said nucleic acid is polymeric and n is an integer of 2 to 100.

* * * * *

UNITED STATES PATENT AND TRADEMARK OFFICE
CERTIFICATE OF CORRECTION

PATENT NO. : 7,442,788 B2  Page 1 of 3
APPLICATION NO. : 10/311386
DATED : October 28, 2008
INVENTOR(S) : Wada et al.

It is certified that error appears in the above-identified patent and that said Letters Patent is hereby corrected as shown below:

At column 3, line 62, after "glutamic" please delete "acid." and insert therefore, --acid,--.

At column 5, line 62, please delete "4." and insert therefore, --4,--.

At column 6, line 43, please delete "acid," and insert therefore, --acid.--.

At column 7, line 50, please delete "aster" and insert therefore, --ester--.

At column 7, line 60, please delete "proton-irritated" and insert therefore, --proton-irradiatated--.

At column 11, line 36, please delete "or" and insert therefore, --of--.

At column 15, line 20,

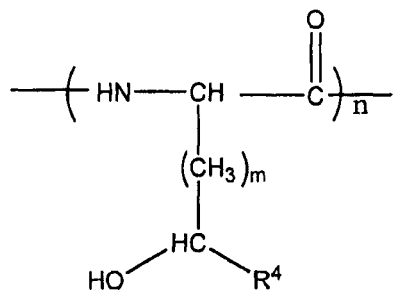

please delete " "

Signed and Sealed this

Eighth Day of June, 2010

David J. Kappos
*Director of the United States Patent and Trademark Office* and insert therefore, -- 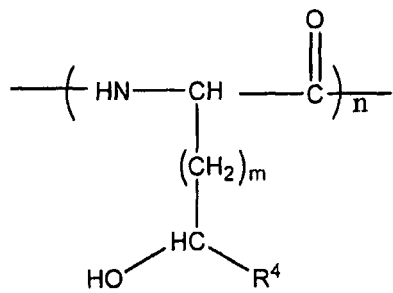 --.

At column 15, line 20, please delete " 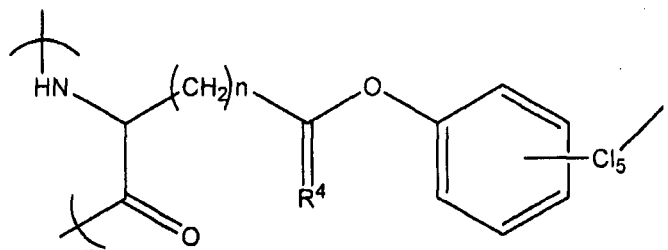 "

and insert therefore, -- 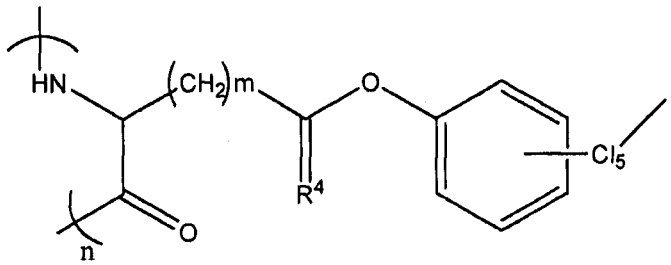 --.

At column 15, line 32, please delete "(1-I)" and insert therefore, --(1-i)--.

At column 29, line 51, after "Table 2," please add --(1 – 2) Investigations using NMR--.

At column 30, line 60, please delete "Ractor" and insert therefore, --Factor--.

At column 36, line 42, before "3'" please delete "and".

At column 39, line 27, after "PRNA = 1.0 x $10^{-4}$M" please add --,--.

At column 39, line 44, before "Examples" please delete ",".

At column 43, line 29, please delete "4'-H,)" and insert therefore, --4'-H),--.

At column 47-48, line 35, please delete " 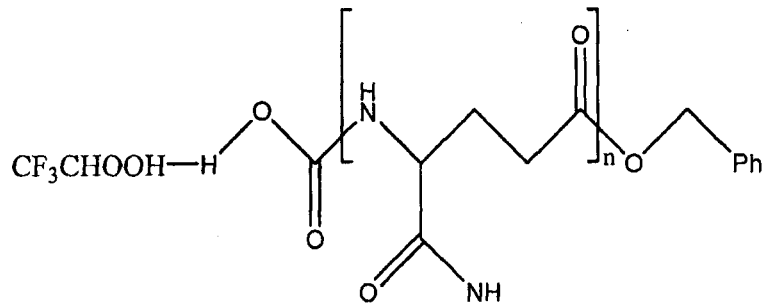 "

and insert therefore, -- 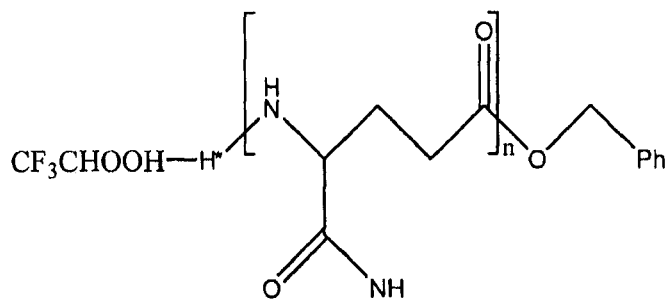 --.

At column 49, line 62, please change "$J_{Ch, \beta}$" to --$J_{CH, \beta}$--.

At column 56, line 15, please delete "-CH$_{25}$,'" and insert therefore, -- -CH$_2$5'--.

At column 56, line 36, please delete "-CH$_{25}$,'" and insert therefore, -- -CH$_2$5'--.

At column 61, line 66, please delete "Fluorenylmethoxyarbonyl-N$^5$" and insert therefore, --Fluorenylmethoxycarbonyl-N$^5$-5'--.

At column 65, line 57, please delete "dichioromethane," and insert therefore, --dichloromethane,--.

At column 69, line 65, in Claim 1, after "consisting of" please delete "monomeric or polymeric".

At column 70, line 14, in Claim 1, please delete "thereof;" and insert therefore, --thereof,--.

At column 70, lines 20-21, in Claim 1, please delete "N-aminoethylomithine," and insert therefore, --N-aminoethylornithine,--.

At column 71, line 26, in Claim 6, please delete "N-aminoethyiglycine," and insert therefore, --N-aminoethylglycine,--.

At column 72, line 1, in Claim 6, please delete "δ-thicarbonyihomoglutamic acid," and insert therefore, --δ-thicarbonylhomoglutamic acid,--.

UNITED STATES PATENT AND TRADEMARK OFFICE
CERTIFICATE OF CORRECTION

| | | |
|---|---|---|
| PATENT NO. | : 7,442,788 B2 | Page 1 of 1 |
| APPLICATION NO. | : 10/311386 | |
| DATED | : October 28, 2008 | |
| INVENTOR(S) | : Wada et al. | |

It is certified that error appears in the above-identified patent and that said Letters Patent is hereby corrected as shown below:

On the Title Page, left column, after item (65), please add:

(30) Foreign Application Priority Data

June 13, 2000 (JP) ........................ 2000-177525

Signed and Sealed this

Thirty-first Day of July, 2012

David J. Kappos
*Director of the United States Patent and Trademark Office*